(12) United States Patent
Steffensen et al.

(10) Patent No.: US 11,813,307 B2
(45) Date of Patent: Nov. 14, 2023

(54) POLYPEPTIDES BINDING ADAMTS5, MMP13 AND AGGRECAN

(71) Applicants: Merck Patent GmbH, Darmstadt (DE); ABLYNX NV, Zwijnaarde (BE)

(72) Inventors: Soren Steffensen, Etterbeek (BE); Gerald Beste, Ghent (BE); Hans Guehring, Geissenheim (DE); Lars Toleikis, Kleinniedesheim (DE); Christoph Ladel, Darmstadt (DE); Sven Lindemann, Darmstadt (DE); Roland Kellner, Heppenheim (DE); Ralf Guenther, Griesheim (DE)

(73) Assignees: MERCK PATENT GMBH, Darmstadt (DE); ABLYNX NV, Zwijnaarde (BE)

( * ) Notice: Subject to any disclaimer, the term of this patent is extended or adjusted under 35 U.S.C. 154(b) by 277 days.

(21) Appl. No.: 16/617,846

(22) PCT Filed: Jun. 4, 2018

(86) PCT No.: PCT/EP2018/064668
§ 371 (c)(1),
(2) Date: Nov. 27, 2019

(87) PCT Pub. No.: WO2018/220236
PCT Pub. Date: Dec. 6, 2018

(65) Prior Publication Data
US 2021/0008160 A1    Jan. 14, 2021

(30) Foreign Application Priority Data
Jun. 2, 2017 (EP) ..................... 17174404

(51) Int. Cl.
| C07K 16/40 | (2006.01) |
| A61K 38/17 | (2006.01) |
| C07K 1/14  | (2006.01) |

(52) U.S. Cl.
CPC ............. *A61K 38/177* (2013.01); *C07K 1/14* (2013.01); *C07K 2317/31* (2013.01); *C07K 2317/565* (2013.01); *C07K 2317/569* (2013.01)

(58) Field of Classification Search
None
See application file for complete search history.

(56) References Cited

U.S. PATENT DOCUMENTS

| 9,156,914 B2 | 10/2015 | Blanchetot et al. | |
| 2008/0311113 A1 | 12/2008 | Morris et al. | |
| 2012/0095193 A1* | 4/2012 | Burden | A61P 25/00 |
| | | | 530/387.3 |
| 2015/0050266 A9 | 2/2015 | Baumeister et al. | |

FOREIGN PATENT DOCUMENTS

| EP | 2 186 894 A1 | 5/2010 |
| EP | 2 258 392 A1 | 12/2010 |
| JP | 2012-531902 A | 12/2012 |
| JP | 2014-533329 A | 12/2014 |
| JP | 2015-532417 A | 11/2015 |
| RU | 2455312 C2 | 7/2012 |
| WO | WO-98/29560 A1 | 7/1998 |
| WO | WO-2008/074840 A2 | 6/2008 |
| WO | WO-2008/074840 A3 | 6/2008 |
| WO | WO-2009/008414 A1 | 1/2009 |
| WO | WO-2011/002968 A2 | 1/2011 |
| WO | WO-2011/002968 A3 | 1/2011 |
| WO | WO-2013/109829 A1 | 7/2013 |
| WO | WO-2015/056808 A1 | 4/2015 |
| WO | WO-2017/080850 A1 | 5/2017 |
| WO | WO-2018/073216 A1 | 4/2018 |

OTHER PUBLICATIONS

Janeway et al., Immunobiology, 3rd edition, 1997, Garland Publishing Inc., pp. 3:1-3:11.*
Rudikoff et al., Proc Natl Acad Sci USA. Mar. 1982;79(6):1979-83.*
Edwards et al.,J Mol Biol. Nov. 14, 2003;334(1): 103-18.*
Llyod et al., Protein Eng Des Sel. Mar. 2009;22(3):159-68. doi: 10.1093/protein/gzn058. Epub Oct. 29, 2008.*
Goel et al., J Immunol. Dec. 15, 2004; 173(12):7358-67.*
Kanyavuz et al., Nat Rev Immunol. Jun. 2019;19(6):355-368. doi: 10.1038/S41577-019-0126-7.*
Ghahroudi et al., FEBS Letters Sep. 15, 1997; 414(3): 521-526.*
Stryer, L., Biochemistry, 4th edition, W. H. Freeman and Company, 1995, pp. 18-23.*

(Continued)

*Primary Examiner* — Michael Szperka
(74) *Attorney, Agent, or Firm* — Foley & Lardner LLP

(57) ABSTRACT

The present invention relates to polypeptides binding Aggrecan as well as ADAMTS5 and/or MMP13, more in particular to polypeptides that comprise or essentially consist of immunoglobulins binding Aggrecan as well as immunoglobulins binding ADAMTS5 and/or immunoglobulins binding MMP13 (also referred to herein as "polypeptides of the invention", and "immunoglobulin(s) of the invention", respectively). The invention also relates to constructs comprising such immunoglobulins, such as immunoglobulin single variable domains (ISVDs) or polypeptides as well as nucleic acids encoding such immunoglobulins or polypeptides (also referred to herein as "nucleic acid(s) of the invention"; to methods for preparing such immunoglobulins, polypeptides and constructs; to host cells expressing or capable of expressing such immunoglobulins or polypeptides; to compositions, and in particular to pharmaceutical compositions, that comprise such immunoglobulins, polypeptides, constructs, nucleic acids and/or host cells; and to uses of immunoglobulins, polypeptides, constructs, nucleic acids, host cells and/or compositions, in particular for prophylactic and/or therapeutic purposes, such as the prophylactic and/or therapeutic purposes mentioned herein. Other aspects, embodiments, advantages and applications of the invention will become clear from the further description herein.

13 Claims, 7 Drawing Sheets

Figure 1:
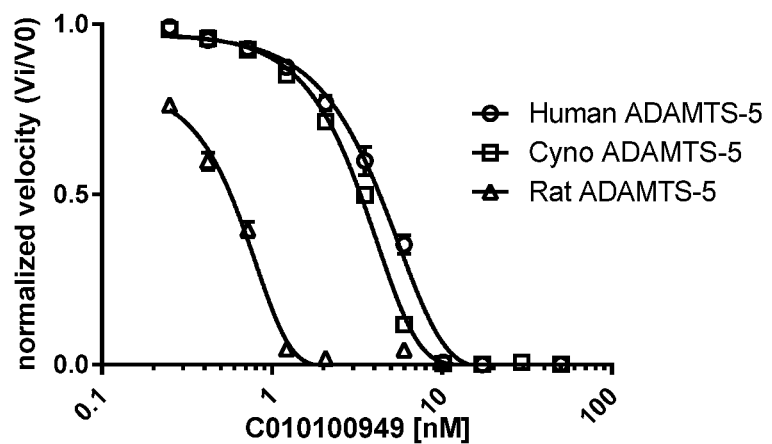

Specification includes a Sequence Listing.

(56) References Cited

OTHER PUBLICATIONS

Chiusaroli et al., "Targeting of ADAMTS5's Ancillary Domain with the Recombinant mAb CRB0017 Ameliorates Disease Progression in a Spontaneous Murine Model of Osteoarthritis", Osteoarthritis and Cartilage, 2013, pp. 1807-1810, vol. 21, No. 11, 2013 Osteoarthritis Research Society International, Elsevier Ltd.
International Search Report and Written Opinion issued in corresponding International Application No. PCT/EP2018/064668 dated Oct. 1, 2018, eighteen (18) pages.
Larkin et al., "Translational Development of an ADAMTS-5 Antibody for Osteoarthritis Disease Modification", Osteoarthritis and Cartilage, 2015, pp. 1254-1266, vol. 23, No. 8, 2015 The Authors, Elsevier ltd and Osteoarthritis Research Society International.
Naito et al., "Development of a Neutralizing Antibody Specific for the Active Form of Matrix Metalloproteinase-13", Biochemistry, 2012, pp. 8877-8884, vol. 51, No. 44, 2012 American Chemical Society, ACS Publications.
Troeberg et al., "Proteases Involved in Cartilage Matrix Degradation in Osteoarthritis", Biochimica et Biophysica Acta, 2012, pp. 133-145, vol. 1824, 2011 Elsevier B.V.
Siebuhr et al.: " The Anti-ADAMTS-5 Nanobody, M6495, Protects Against Cartilage Breakdown in Cartilage and Synovial Joint Tissue Explant Models", Apr. 1, 2018, p. S187, XP055493294, Retrieved from the Internet: URL: https://www.oarsijournal.com/article/S1063-4584(18)30502-8/pdf [retrieved on Jul. 17, 2018].
Office Action issued in European Patent Application No. 18730689.9 dated Feb. 9, 2021, six (6) pages.
Kontermann, "Strategies for extended serum half-life of protein therapeutics", Current Opinion in Biotechnology, 2011, pp. 868-876, vol. 22, No. 6, Elsevier Ltd.
Santamaria et al.: "Antibody-based exosite inhibitors of ADAMTS-5 (aggrecanase-2)", Biochemical Journal, Nov. 2015, pp. 391-401, vol. 471, No. 3, Portland Press Limited.
Hoshi, Hiroko et al: "Effect of inhibiting MMP13 and ADAMTS5 by intra-articular injection of small interfering RNA in a surgically induced osteoarthritis model of mice", Cell and Tissue Research, Springer, DE, vol. 368, No. 2, Jan. 24, 2017 (Jan. 24, 2017), pp. 379-387, XP036216068.
Appleby et al., "Biochemical Characterization and structure determination of a Potent, Selective Antibody Inhibitor of Human MMP9", Journal of Biological Chemistry, 2017, pp. 6810-6820, vol. 292, No. 16, 2017 The American Society for Biochemistry and Molecular Biology, Inc.
Demeestere et al., "Development and Validation of a Small Single-Domain Antibody That Effectively Inhibits Matrix Metalloproteinase 8", The American Society of Gene & Cell Therapy, May 2016, pp. 890-902, vol. 24, No. 5.
Harmsen et al., "Properties, Production, and Applications of Camelid Single-Domain Antibody Fragments", Applied Microbiology and Biotechnology, 2007, pp. 13-22, vol. 77, No. 1, Springer-Verlag 2007.
International Search Report and Written Opinion Issued in Corresponding International Application No. PCT/EP2018/064667 dated Oct. 2, 2018, thirty-two (32) pages total.
Mohan et al., "Matrix Metalloproteinase Protein Inhibitors: Highlighting a new Beginning for Metalloproteinases in Medicine", Metalloproteinases in Medicine, 2016, pp. 1-16, vol. 3.
Nam et al., "Active-Site MMP-Selective Antibody Inhibitors Discovered from Convex Paratope Synthetic Libraries", PNAS, Dec. 27, 2016, pp. 14970-14975, vol. 113, No. 52.
Non-Final Office Action on U.S. Appl. No. 16/617,869 dated Jun. 16, 2021.
Pivetta et al., "MMP-13 Stimulates Osteoclast Differentiation and Activation in Tumour Breast Bone Metastases", Breast Cancer Research, 2011, pp. R105 (1-15), vol. 13, No. 5.
U.S. Office Action on U.S. Appl. No. 16/617,869 dated Nov. 17, 2021.

Bever et al., "VHH antibodies: Emerging reagents for the analysis of environmental chemicals", Anal Bioanal Chem, Author Manuscript, Sep. 1, 2017, pp. 1-34, vol. 408, No. 22.
Kishimoto et al., "Therapeutic applications of antigen binding domain VHH derived from heavy chain antibodies of Camelidae", Medchem News, Feb. 1, 2017, pp. 35-41, vol. 27, No. 1, English Abstract.
Caljon et al: "Affinity Is an Important Determinant of the Anti-Trypanosome Activity of Nanobodies", PLoS Neglected Tropical Diseases, Nov. 15, 2012, pp. 1-8, e1902, vol. 6, Issue 11, XP055085029, ISSN: 193-2727, DOI: 10.1371/journal.pntd.0001902.
Dennis, "Welfare Issues of Genetically Modified Animals", ILAR Journal, Apr. 1, 2002, pp. 100-109, vol. 43, No. 2.
Mitchell et al., "Comparative analysis of nanobody sequence and structure data", Proteins: Structure, Function, and Bioinformatics, Apr. 15, 2018 (Apr. 15, 2018), pp. 697-706, vol. 86, No. 7, XP055788282, US, ISSN: 0887-3585, DOI: 10.1002/prot.25497, Retrieved from the Internet: URL: https://api.wiley.com/onlinelibrary/tdm/v1/articles/10.1002%2Fprot.25497.
Roitt I. et al., "Immunology" Fifth Edition, Moscow, Mir, 2000, pp. 110-111 (English Translation).
Zhou et al., "Developing tTA Transgenic Rats for Inducible and Reversible Gene Expression", International Journal of Biological Sciences, Jan. 29, 2009, pp. 171-181, vol. 5, No. 2, Ivyspring International Publisher.
Chen et al., "Fusion protein linkers: Property, Design and Functionality", Author Manuscript of Advanced Drug Delivery Reviews, Oct. 15, 2013, pp. 1-35, vol. 64, No. 10, 2012 Elsevier B.V.
Colman P.M., "Effects of amino acid sequence changes on antibody-antigen interactions", Research in Immunology, 1994, pp. 33-36, vol. 145, Issue 1.
Dashivets T. et al., "Oxidation in the complementarity-determining regions differentially influences the properties of therapeutic antibodies", Mabs, 2016, pp. 1525-1535, vol. 8, No. 8, Taylor & Francis Group, LLC.
De Pascalis et al., "Grafting of "Abbreviated" Complementarity-Determining Regions Containing Specificity-Determining Residues Essential for Ligand Contact to Engineer a Less Immunogenic Humanized Monoclonal Antibody", The Journal of Immunology, 2002, pp. 3076-3084, vol. 169, The American Association of Immunologists, Inc.
Kuznetsova E., "Brackets in the text of the legal document as a Linguistic and Cognitive Phenomenon", 2015, N3, pp. 37-43, Vestnik MGOU. Series, Russian Philology, English Abstract.
Maeda et al., "Engineering of Functional Chimeric Protein G-Vargula Luciferase", Analytical Biochemistry, 1997, pp. 147-152, vol. 249, Article No. AB972181, Academic Press.
Muller et al., "Spliceosomal Peptide P140 for Immunotherapy of Systemic Lupus Erythematosus", Arthritis & Rheumatism, Dec. 2008, pp. 3873-3883, vol. 58, No. 12, 2008, American College of Rheumatology.
Safdari Y. et al., "Antibody humanization methods—a review and update", Biotechnology and Genetic Engineering Reviews, 2013, pp. 175-186, vol. 29, No. 2, 2013 Taylor & Francis.
Torres M. et al., "The immunoglobulin constant region contributes to affinity and specificity", Trends in Immunology, 2008, pp. 91-97, vol. 29, No. 2, 2007 Elsevier Ltd.
Vajdos et al., "Comprehensive Functional Maps of the Antigen-binding Site of an Anti-ErbB2 Antibody Obtained with Shotgun Scanning Mutagenesis", Journal of Molecular Biology, 2002, pp. 415-428, vol. 320, 2002 Elsevier Science Ltd.
Banerjee et al., "Poly(ethylene glycol)-Prodrug Conjugates: Concept, Design, and Applications", Journal of Drug Delivery, May 7, 2012, pp. 1-17, vol. 2012, Article ID 103973, Hindawi Publishing Corporation.
Isin et al., "Use of Radiolabeled Compounds in Drug Metabolism and Pharmocokinetic Studies", Chemical Research in Toxicology, Feb. 28, 2012, pp. 532-542, vol. 25, 2012 American Chemical Society.
Kratz et al., "Clinical impact of serum proteins on drug delivery", Journal of Controlled Release, Jul. 20, 2012, pp. 429-445, vol. 161, 2011 Elsevier B.V.

(56) References Cited

OTHER PUBLICATIONS

Final Office Action on U.S. Appl. No. 16/617,869 dated Feb. 1, 2023.

* cited by examiner $IC_{50} = 0{,}03724 \ \mu M$

SEQUENCE LISTING

<160> NUMBER OF SEQ ID NOS: 68

<210> SEQ ID NO 1
<211> LENGTH: 593
<212> TYPE: PRT
<213> ORGANISM: Artificial Sequence
<220> FEATURE:
<223> OTHER INFORMATION: Description of Artificial Sequence: Synthetic polypeptide comprising first ISVD binding MMP13, second ISVD binding ADAMTS5, third ISVD binding Aggrecan and fourth ISVD binding Aggrecan

<400> SEQUENCE: 1

```
Glu Val Gln Leu Val Glu Ser Gly Gly Gly Val Val Gln Pro Gly Gly
1               5                   10                  15

Ser Leu Arg Leu Ser Cys Ala Ala Ser Gly Phe Ala Phe Ser Ala Ala
            20                  25                  30

Tyr Met Ser Trp Val Arg Gln Ala Pro Gly Lys Gly Leu Glu Trp Val
        35                  40                  45

Ser Ser Ile Ser Asp Asp Gly Ser Lys Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Asn Thr Gly Tyr Gly Ala Thr Thr Thr Arg Pro Gly Arg Tyr Trp Gly
            100                 105                 110

Gln Gly Thr Leu Val Thr Val Ser Ser Gly Gly Gly Ser Gly Gly
        115                 120                 125

Gly Gly Ser Gly Gly Gly Ser Gly Gly Gly Ser Gly Gly Gly
    130                 135                 140

Gly Ser Gly Gly Gly Ser Gly Gly Gly Ser Glu Val Gln Leu
145                 150                 155                 160

Val Glu Ser Gly Gly Gly Val Val Gln Pro Gly Gly Ser Leu Arg Leu
                165                 170                 175

Ser Cys Ala Ala Ser Gly Arg Thr Val Ser Ser Tyr Ala Met Gly Trp
            180                 185                 190

Phe Arg Gln Ala Pro Gly Lys Glu Arg Glu Phe Val Ala Gly Ile Ser
        195                 200                 205

Arg Ser Ala Glu Arg Thr Tyr Tyr Val Asp Ser Leu Lys Gly Arg Phe
    210                 215                 220

Thr Ile Ser Arg Asp Asn Ser Lys Asn Thr Val Tyr Leu Gln Met Asn
225                 230                 235                 240

Ser Leu Arg Pro Glu Asp Thr Ala Leu Tyr Tyr Cys Ala Ala Asp Leu
                245                 250                 255
```

```
Asp Pro Asn Arg Ile Phe Ser Arg Glu Glu Tyr Ala Tyr Trp Gly Gln
                260                 265                 270

Gly Thr Leu Val Thr Val Ser Ser Gly Gly Gly Gly Ser Gly Gly Gly
            275                 280                 285

Gly Ser Gly Gly Gly Ser Gly Gly Gly Ser Gly Gly Gly Gly Ser Gly
        290                 295                 300

Gly Gly Gly Ser Gly Gly Gly Gly Ser Glu Val Gln Leu Val
305                 310                 315                 320

Glu Ser Gly Gly Gly Val Val Gln Pro Gly Gly Ser Leu Arg Leu Ser
                325                 330                 335

Cys Ala Ala Ser Gly Ser Thr Phe Ile Ile Asn Val Val Arg Trp Tyr
            340                 345                 350

Arg Arg Ala Pro Gly Lys Gln Arg Glu Leu Val Ala Thr Ile Ser Ser
        355                 360                 365

Gly Gly Asn Ala Asn Tyr Val Asp Ser Val Arg Gly Arg Phe Thr Ile
    370                 375                 380

Ser Arg Asp Asn Ser Lys Asn Thr Val Tyr Leu Gln Met Asn Ser Leu
385                 390                 395                 400

Arg Pro Glu Asp Thr Ala Leu Tyr Tyr Cys Asn Val Pro Thr Thr His
                405                 410                 415

Tyr Gly Gly Val Tyr Tyr Gly Pro Tyr Trp Gly Gln Gly Thr Leu Val
            420                 425                 430

Thr Val Ser Ser Gly Gly Gly Gly Ser Gly Gly Gly Gly Ser Gly Gly
        435                 440                 445

Gly Gly Ser Gly Gly Gly Gly Ser Gly Gly Gly Gly Ser Gly Gly Gly
    450                 455                 460

Gly Ser Gly Gly Gly Gly Ser Glu Val Gln Leu Val Glu Ser Gly Gly
465                 470                 475                 480

Gly Val Val Gln Pro Gly Gly Ser Leu Arg Leu Ser Cys Ala Ala Ser
                485                 490                 495

Gly Ser Thr Phe Ile Ile Asn Val Val Arg Trp Tyr Arg Arg Ala Pro
            500                 505                 510

Gly Lys Gln Arg Glu Leu Val Ala Thr Ile Ser Ser Gly Gly Asn Ala
        515                 520                 525

Asn Tyr Val Asp Ser Val Arg Gly Arg Phe Thr Ile Ser Arg Asp Asn
    530                 535                 540

Ser Lys Asn Thr Val Tyr Leu Gln Met Asn Ser Leu Arg Pro Glu Asp
545                 550                 555                 560

Thr Ala Leu Tyr Tyr Cys Asn Val Pro Thr Thr His Tyr Gly Gly Val
                565                 570                 575

Tyr Tyr Gly Pro Tyr Trp Gly Gln Gly Thr Leu Val Thr Val Ser Ser
            580                 585                 590

Ala

<210> SEQ ID NO 2
<211> LENGTH: 121
<212> TYPE: PRT
<213> ORGANISM: Artificial Sequence
<220> FEATURE:
<223> OTHER INFORMATION: Description of Artificial Sequence: Synthetic
      anti-MMP13 immunoglobulin single variable domain (ISVD)

<400> SEQUENCE: 2

Glu Val Gln Leu Val Glu Ser Gly Gly Gly Val Val Gln Pro Gly Gly
1               5                   10                  15
```

```
Ser Leu Arg Leu Ser Cys Ala Ala Ser Gly Phe Ala Phe Ser Ala Ala
            20                  25                  30

Tyr Met Ser Trp Val Arg Gln Ala Pro Gly Lys Gly Leu Glu Trp Val
        35                  40                  45

Ser Ser Ile Ser Asp Asp Gly Ser Lys Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Asn Thr Gly Tyr Gly Ala Thr Thr Thr Arg Pro Gly Tyr Trp Gly
            100                 105                 110

Gln Gly Thr Leu Val Thr Val Ser Ser
        115                 120

<210> SEQ ID NO 3
<211> LENGTH: 124
<212> TYPE: PRT
<213> ORGANISM: Artificial Sequence
<220> FEATURE:
<223> OTHER INFORMATION: Description of Artificial Sequence: Synthetic
      anti-ADAMTS5 immunoglobulin single variable domain (ISVD)

<400> SEQUENCE: 3

Glu Val Gln Leu Val Glu Ser Gly Gly Gly Val Val Gln Pro Gly Gly
1               5                   10                  15

Ser Leu Arg Leu Ser Cys Ala Ala Ser Gly Arg Thr Val Ser Ser Tyr
            20                  25                  30

Ala Met Gly Trp Phe Arg Gln Ala Pro Gly Lys Glu Arg Glu Phe Val
        35                  40                  45

Ala Gly Ile Ser Arg Ser Ala Glu Arg Thr Tyr Tyr Val Asp Ser Leu
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Ala Asp Leu Asp Pro Asn Arg Ile Phe Ser Arg Glu Glu Tyr Ala
            100                 105                 110

Tyr Trp Gly Gln Gly Thr Leu Val Thr Val Ser Ser
        115                 120

<210> SEQ ID NO 4
<211> LENGTH: 121
<212> TYPE: PRT
<213> ORGANISM: Artificial Sequence
<220> FEATURE:
<223> OTHER INFORMATION: Description of Artificial Sequence: Synthetic
      anti-Aggrecan immunoglobulin single variable domain (ISVD)

<400> SEQUENCE: 4

Glu Val Gln Leu Val Glu Ser Gly Gly Gly Val Val Gln Pro Gly Gly
1               5                   10                  15

Ser Leu Arg Leu Ser Cys Ala Ala Ser Gly Ser Thr Phe Ile Ile Asn
            20                  25                  30

Val Val Arg Trp Tyr Arg Arg Ala Pro Gly Lys Gln Arg Glu Leu Val
        35                  40                  45

Ala Thr Ile Ser Ser Gly Gly Asn Ala Asn Tyr Val Asp Ser Val Arg
    50                  55                  60
```

```
Gly Arg Phe Thr Ile Ser Arg Asp Asn Ser Lys Asn Thr Val Tyr Leu
 65                  70                  75                  80

Gln Met Asn Ser Leu Arg Pro Glu Asp Thr Ala Leu Tyr Tyr Cys Asn
                 85                  90                  95

Val Pro Thr Thr His Tyr Gly Gly Val Tyr Tyr Gly Pro Tyr Trp Gly
            100                 105                 110

Gln Gly Thr Leu Val Thr Val Ser Ser
            115                 120

<210> SEQ ID NO 5
<211> LENGTH: 434
<212> TYPE: PRT
<213> ORGANISM: Artificial Sequence
<220> FEATURE:
<223> OTHER INFORMATION: Description of Artificial Sequence: Synthetic
      polypeptide comprising first ISVD binding MMP13, second ISVD
      binding Aggrecan and third ISVD binding Aggrecan

<400> SEQUENCE: 5

Glu Val Gln Leu Val Glu Ser Gly Gly Gly Val Val Gln Pro Gly Gly
 1               5                  10                  15

Ser Leu Arg Leu Ser Cys Ala Ala Ser Gly Phe Ala Phe Ser Ala Ala
            20                  25                  30

Tyr Met Ser Trp Val Arg Gln Ala Pro Gly Lys Gly Leu Glu Trp Val
        35                  40                  45

Ser Ser Ile Ser Asp Asp Gly Ser Lys Thr Tyr Tyr Ala Asp Ser Val
    50                  55                  60

Lys Gly Arg Phe Thr Ile Ser Arg Asp Asn Ser Lys Asn Thr Val Tyr
 65                  70                  75                  80

Leu Gln Met Asn Ser Leu Arg Pro Glu Asp Thr Ala Leu Tyr Tyr Cys
                 85                  90                  95

Asn Thr Gly Tyr Gly Ala Thr Thr Thr Arg Pro Gly Arg Tyr Trp Gly
            100                 105                 110

Gln Gly Thr Leu Val Thr Val Ser Ser Gly Gly Gly Ser Gly Gly Gly
            115                 120                 125

Gly Gly Ser Gly Gly Gly Gly Ser Gly Gly Gly Ser Gly Gly Gly
        130                 135                 140

Gly Ser Gly Gly Gly Gly Ser Gly Gly Gly Ser Glu Val Gln Leu
145                 150                 155                 160

Val Glu Ser Gly Gly Gly Val Val Gln Pro Gly Gly Ser Leu Arg Leu
                165                 170                 175

Ser Cys Ala Ala Ser Gly Ser Thr Phe Ile Ile Asn Val Val Arg Trp
            180                 185                 190

Tyr Arg Arg Ala Pro Gly Lys Gln Arg Glu Leu Val Ala Thr Ile Ser
        195                 200                 205

Ser Gly Gly Asn Ala Asn Tyr Val Asp Ser Val Arg Gly Arg Phe Thr
    210                 215                 220

Ile Ser Arg Asp Asn Ser Lys Asn Thr Val Tyr Leu Gln Met Asn Ser
225                 230                 235                 240

Leu Arg Pro Glu Asp Thr Ala Leu Tyr Tyr Cys Asn Val Pro Thr Thr
                245                 250                 255

His Tyr Gly Gly Val Tyr Tyr Gly Pro Tyr Trp Gly Gln Gly Thr Leu
            260                 265                 270

Val Thr Val Ser Ser Gly Gly Gly Gly Ser Gly Gly Gly Gly Ser Gly
        275                 280                 285

Gly Gly Ser Gly Gly Gly Gly Ser Gly Gly Gly Gly Ser Gly Gly
```

```
                290                 295                 300
Gly Gly Ser Gly Gly Gly Ser Glu Val Gln Leu Val Glu Ser Gly
305                 310                 315                 320

Gly Gly Val Val Gln Pro Gly Gly Ser Leu Arg Leu Ser Cys Ala Ala
            325                 330                 335

Ser Gly Ser Thr Phe Ile Ile Asn Val Val Arg Trp Tyr Arg Arg Ala
            340                 345                 350

Pro Gly Lys Gln Arg Glu Leu Val Ala Thr Ile Ser Ser Gly Gly Asn
            355                 360                 365

Ala Asn Tyr Val Asp Ser Val Arg Gly Arg Phe Thr Ile Ser Arg Asp
370                 375                 380

Asn Ser Lys Asn Thr Val Tyr Leu Gln Met Asn Ser Leu Arg Pro Glu
385                 390                 395                 400

Asp Thr Ala Leu Tyr Tyr Cys Asn Val Pro Thr Thr His Tyr Gly Gly
                405                 410                 415

Val Tyr Tyr Gly Pro Tyr Trp Gly Gln Gly Thr Leu Val Thr Val Ser
            420                 425                 430

Ser Ala

<210> SEQ ID NO 6
<211> LENGTH: 437
<212> TYPE: PRT
<213> ORGANISM: Artificial Sequence
<220> FEATURE:
<223> OTHER INFORMATION: Description of Artificial Sequence: Synthetic
      polypeptide comprising first ISVD binding ADAMTS5, second ISVD
      binding Aggrecan and third ISVD binding Aggrecan

<400> SEQUENCE: 6

Glu Val Gln Leu Val Glu Ser Gly Gly Gly Val Val Gln Pro Gly Gly
1               5                   10                  15

Ser Leu Arg Leu Ser Cys Ala Ala Ser Gly Arg Thr Val Ser Ser Tyr
            20                  25                  30

Ala Met Gly Trp Phe Arg Gln Ala Pro Gly Lys Glu Arg Glu Phe Val
        35                  40                  45

Ala Gly Ile Ser Arg Ser Ala Glu Arg Thr Tyr Tyr Val Asp Ser Leu
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Ala Asp Leu Asp Pro Asn Arg Ile Phe Ser Arg Glu Glu Tyr Ala
            100                 105                 110

Tyr Trp Gly Gln Gly Thr Leu Val Thr Val Ser Ser Gly Gly Gly Gly
        115                 120                 125

Ser Gly Gly Gly Gly Ser Gly Gly Gly Ser Gly Gly Gly Gly Ser
    130                 135                 140

Gly Gly Gly Gly Ser Gly Gly Gly Ser Gly Gly Gly Gly Ser Glu
145                 150                 155                 160

Val Gln Leu Val Glu Ser Gly Gly Gly Val Val Gln Pro Gly Gly Ser
                165                 170                 175

Leu Arg Leu Ser Cys Ala Ala Ser Gly Ser Thr Phe Ile Ile Asn Val
            180                 185                 190

Val Arg Trp Tyr Arg Arg Ala Pro Gly Lys Gln Arg Glu Leu Val Ala
        195                 200                 205
```

```
Thr Ile Ser Ser Gly Gly Asn Ala Asn Tyr Val Asp Ser Val Arg Gly
            210                 215                 220
Arg Phe Thr Ile Ser Arg Asp Asn Ser Lys Asn Thr Val Tyr Leu Gln
225                 230                 235                 240
Met Asn Ser Leu Arg Pro Glu Asp Thr Ala Leu Tyr Tyr Cys Asn Val
                245                 250                 255
Pro Thr Thr His Tyr Gly Gly Val Tyr Tyr Gly Pro Tyr Trp Gly Gln
                260                 265                 270
Gly Thr Leu Val Thr Val Ser Gly Gly Gly Gly Ser Gly Gly Gly
            275                 280                 285
Gly Ser Gly Gly Gly Gly Ser Gly Gly Gly Ser Gly Gly Gly Gly
            290                 295                 300
Ser Gly Gly Gly Gly Ser Gly Gly Gly Ser Glu Val Gln Leu Val
305                 310                 315                 320
Glu Ser Gly Gly Gly Val Val Gln Pro Gly Gly Ser Leu Arg Leu Ser
                325                 330                 335
Cys Ala Ala Ser Gly Ser Thr Phe Ile Ile Asn Val Val Arg Trp Tyr
                340                 345                 350
Arg Arg Ala Pro Gly Lys Gln Arg Glu Leu Val Ala Thr Ile Ser Ser
                355                 360                 365
Gly Gly Asn Ala Asn Tyr Val Asp Ser Val Arg Gly Arg Phe Thr Ile
            370                 375                 380
Ser Arg Asp Asn Ser Lys Asn Thr Val Tyr Leu Gln Met Asn Ser Leu
385                 390                 395                 400
Arg Pro Glu Asp Thr Ala Leu Tyr Tyr Cys Asn Val Pro Thr Thr His
                405                 410                 415
Tyr Gly Gly Val Tyr Tyr Gly Pro Tyr Trp Gly Gln Gly Thr Leu Val
                420                 425                 430
Thr Val Ser Ser Ala
            435
```

```
<210> SEQ ID NO 7
<211> LENGTH: 25
<212> TYPE: PRT
<213> ORGANISM: Artificial Sequence
<220> FEATURE:
<223> OTHER INFORMATION: Description of Artificial Sequence: Synthetic
      framework 1 sequence

<400> SEQUENCE: 7

Glu Val Gln Leu Val Glu Ser Gly Gly Gly Val Val Gln Pro Gly Gly
1               5                   10                  15
Ser Leu Arg Leu Ser Cys Ala Ala Ser
            20                  25

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic
      CDR1 of anti-MMP13 immunoglobulin single variable domain (ISVD)

<400> SEQUENCE: 8

Gly Phe Ala Phe Ser Ala Ala Tyr Met Ser
1               5                   10

<210> SEQ ID NO 9
<211> LENGTH: 14
```

```
<212> TYPE: PRT
<213> ORGANISM: Artificial Sequence
<220> FEATURE:
<223> OTHER INFORMATION: Description of Artificial Sequence: Synthetic
      framework 2 sequence

<400> SEQUENCE: 9

Trp Val Arg Gln Ala Pro Gly Lys Gly Leu Glu Trp Val Ser
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
      CDR2 of anti-MMP13 immunoglobulin single variable domain (ISVD)

<400> SEQUENCE: 10

Ser Ile Ser Asp Asp Gly Ser Lys Thr Tyr
1               5                   10

<210> SEQ ID NO 11
<211> LENGTH: 39
<212> TYPE: PRT
<213> ORGANISM: Artificial Sequence
<220> FEATURE:
<223> OTHER INFORMATION: Description of Artificial Sequence: Synthetic
      framework 3 sequence

<400> SEQUENCE: 11

Tyr Ala Asp Ser Val Lys Gly Arg Phe Thr Ile Ser Arg Asp Asn Ser
1               5                   10                  15

Lys Asn Thr Val Tyr Leu Gln Met Asn Ser Leu Arg Pro Glu Asp Thr
            20                  25                  30

Ala Leu Tyr Tyr Cys Asn Thr
        35

<210> SEQ ID NO 12
<211> LENGTH: 12
<212> TYPE: PRT
<213> ORGANISM: Artificial Sequence
<220> FEATURE:
<223> OTHER INFORMATION: Description of Artificial Sequence: Synthetic
      CDR3 of anti-MMP13 immunoglobulin single variable domain (ISVD)

<400> SEQUENCE: 12

Gly Tyr Gly Ala Thr Thr Thr Arg Pro Gly Arg Tyr
1               5                   10

<210> SEQ ID NO 13
<211> LENGTH: 11
<212> TYPE: PRT
<213> ORGANISM: Artificial Sequence
<220> FEATURE:
<223> OTHER INFORMATION: Description of Artificial Sequence: Synthetic
      framework 4 sequence

<400> SEQUENCE: 13

Trp Gly Gln Gly Thr Leu Val Thr Val Ser Ser
1               5                   10

<210> SEQ ID NO 14
<211> LENGTH: 10
<212> TYPE: PRT
<213> ORGANISM: Artificial Sequence
<220> FEATURE:
```

<223> OTHER INFORMATION: Description of Artificial Sequence: Synthetic
      CDR1 of anti-ADAMTS5 immunoglobulin single variable domain (ISVD)

<400> SEQUENCE: 14

Gly Arg Thr Val Ser Ser Tyr Ala Met Gly
1               5                  10

<210> SEQ ID NO 15
<211> LENGTH: 14
<212> TYPE: PRT
<213> ORGANISM: Artificial Sequence
<220> FEATURE:
<223> OTHER INFORMATION: Description of Artificial Sequence: Synthetic
      framework 2 sequence

<400> SEQUENCE: 15

Trp Phe Arg Gln Ala Pro Gly Lys Glu Arg Glu Phe Val Ala
1               5                  10

<210> SEQ ID NO 16
<211> LENGTH: 10
<212> TYPE: PRT
<213> ORGANISM: Artificial Sequence
<220> FEATURE:
<223> OTHER INFORMATION: Description of Artificial Sequence: Synthetic
      CDR2 of anti-ADAMTS5 immunoglobulin single variable domain (ISVD)

<400> SEQUENCE: 16

Gly Ile Ser Arg Ser Ala Glu Arg Thr Tyr
1               5                  10

<210> SEQ ID NO 17
<211> LENGTH: 39
<212> TYPE: PRT
<213> ORGANISM: Artificial Sequence
<220> FEATURE:
<223> OTHER INFORMATION: Description of Artificial Sequence: Synthetic
      framework 3 sequence

<400> SEQUENCE: 17

Tyr Val Asp Ser Leu Lys Gly Arg Phe Thr Ile Ser Arg Asp Asn Ser
1               5                  10                  15

Lys Asn Thr Val Tyr Leu Gln Met Asn Ser Leu Arg Pro Glu Asp Thr
            20                  25                  30

Ala Leu Tyr Tyr Cys Ala Ala
        35

<210> SEQ ID NO 18
<211> LENGTH: 15
<212> TYPE: PRT
<213> ORGANISM: Artificial Sequence
<220> FEATURE:
<223> OTHER INFORMATION: Description of Artificial Sequence: Synthetic
      CDR3 of anti-ADAMTS5 immunoglobulin single variable domain (ISVD)

<400> SEQUENCE: 18

Asp Leu Asp Pro Asn Arg Ile Phe Ser Arg Glu Glu Tyr Ala Tyr
1               5                  10                  15

<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence: Synthetic
      CDR1 of anti-Aggrecan immunoglobulin single variable domain (ISVD)

```
<400> SEQUENCE: 19

Gly Ser Thr Phe Ile Ile Asn Val Val Arg
1               5                   10

<210> SEQ ID NO 20
<211> LENGTH: 14
<212> TYPE: PRT
<213> ORGANISM: Artificial Sequence
<220> FEATURE:
<223> OTHER INFORMATION: Description of Artificial Sequence: Synthetic
      framework 2 sequence

<400> SEQUENCE: 20

Trp Tyr Arg Arg Ala Pro Gly Lys Gln Arg Glu Leu Val Ala
1               5                   10

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      CDR2 of anti-Aggrecan immunoglobulin single variable domain (ISVD)

<400> SEQUENCE: 21

Thr Ile Ser Ser Gly Gly Asn Ala Asn
1               5

<210> SEQ ID NO 22
<211> LENGTH: 39
<212> TYPE: PRT
<213> ORGANISM: Artificial Sequence
<220> FEATURE:
<223> OTHER INFORMATION: Description of Artificial Sequence: Synthetic
      framework 3 sequence

<400> SEQUENCE: 22

Tyr Val Asp Ser Val Arg Gly Arg Phe Thr Ile Ser Arg Asp Asn Ser
1               5                   10                  15

Lys Asn Thr Val Tyr Leu Gln Met Asn Ser Leu Arg Pro Glu Asp Thr
            20                  25                  30

Ala Leu Tyr Tyr Cys Asn Val
        35

<210> SEQ ID NO 23
<211> LENGTH: 13
<212> TYPE: PRT
<213> ORGANISM: Artificial Sequence
<220> FEATURE:
<223> OTHER INFORMATION: Description of Artificial Sequence: Synthetic
      CDR3 of anti-Aggrecan immunoglobulin single variable domain (ISVD)

<400> SEQUENCE: 23

Pro Thr Thr His Tyr Gly Gly Val Tyr Tyr Gly Pro Tyr
1               5                   10

<210> SEQ ID NO 24
<211> LENGTH: 3
<212> TYPE: PRT
<213> ORGANISM: Artificial Sequence
<220> FEATURE:
<223> OTHER INFORMATION: Linker Sequence

<400> SEQUENCE: 24

Ala Ala Ala
1
```

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: Synthetic
      Linker sequence

<400> SEQUENCE: 25

Gly Gly Gly Gly Ser
1               5

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      Linker sequence

<400> SEQUENCE: 26

Ser Gly Gly Ser Gly Gly Ser
1               5

<210> SEQ ID NO 27
<211> LENGTH: 8
<212> TYPE: PRT
<213> ORGANISM: Artificial Sequence
<220> FEATURE:
<223> OTHER INFORMATION: Description of Artificial Sequence: Synthetic
      Linker sequence

<400> SEQUENCE: 27

Gly Gly Gly Gly Gly Gly Gly Ser
1               5

<210> SEQ ID NO 28
<211> LENGTH: 9
<212> TYPE: PRT
<213> ORGANISM: Artificial Sequence
<220> FEATURE:
<223> OTHER INFORMATION: Description of Artificial Sequence: Synthetic
      Linker sequence

<400> SEQUENCE: 28

Gly Gly Gly Gly Ser Gly Gly Gly Ser
1               5

<210> SEQ ID NO 29
<211> LENGTH: 10
<212> TYPE: PRT
<213> ORGANISM: Artificial Sequence
<220> FEATURE:
<223> OTHER INFORMATION: Description of Artificial Sequence: Synthetic
      Linker sequence

<400> SEQUENCE: 29

Gly Gly Gly Gly Ser Gly Gly Gly Gly Ser
1               5                   10

<210> SEQ ID NO 30
<211> LENGTH: 15
<212> TYPE: PRT
<213> ORGANISM: Artificial Sequence
<220> FEATURE:
<223> OTHER INFORMATION: Description of Artificial Sequence: Synthetic
      Linker sequence

<400> SEQUENCE: 30

Gly Gly Gly Gly Ser Gly Gly Gly Gly Ser Gly Gly Gly Gly Ser
1               5                   10                  15

<210> SEQ ID NO 31
<211> LENGTH: 18
<212> TYPE: PRT
<213> ORGANISM: Artificial Sequence
<220> FEATURE:
<223> OTHER INFORMATION: Description of Artificial Sequence: Synthetic
      Linker sequence

<400> SEQUENCE: 31

Gly Gly Gly Gly Ser Gly Gly Gly Gly Ser Gly Gly Gly Gly Gly
1               5                   10                  15

Gly Ser

<210> SEQ ID NO 32
<211> LENGTH: 20
<212> TYPE: PRT
<213> ORGANISM: Artificial Sequence
<220> FEATURE:
<223> OTHER INFORMATION: Description of Artificial Sequence: Synthetic
      Linker sequence

<400> SEQUENCE: 32

Gly Gly Gly Gly Ser Gly Gly Gly Gly Ser Gly Gly Gly Gly Ser Gly
1               5                   10                  15

Gly Gly Gly Ser
            20

<210> SEQ ID NO 33
<211> LENGTH: 25
<212> TYPE: PRT
<213> ORGANISM: Artificial Sequence
<220> FEATURE:
<223> OTHER INFORMATION: Description of Artificial Sequence: Synthetic
      Linker sequence

<400> SEQUENCE: 33

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 34
<211> LENGTH: 30
<212> TYPE: PRT
<213> ORGANISM: Artificial Sequence
<220> FEATURE:
<223> OTHER INFORMATION: Description of Artificial Sequence: Synthetic
      Linker sequence

<400> SEQUENCE: 34

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 35
<211> LENGTH: 35
<212> TYPE: PRT
<213> ORGANISM: Artificial Sequence
<220> FEATURE:

<223> OTHER INFORMATION: Description of Artificial Sequence: Synthetic
      Linker sequence

<400> SEQUENCE: 35

Gly Gly Gly Gly Ser Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser
        35

<210> SEQ ID NO 36
<211> LENGTH: 40
<212> TYPE: PRT
<213> ORGANISM: Artificial Sequence
<220> FEATURE:
<223> OTHER INFORMATION: Description of Artificial Sequence: Synthetic
      Linker sequence

<400> SEQUENCE: 36

Gly Gly Gly Gly Ser Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser
        35                  40

<210> SEQ ID NO 37
<211> LENGTH: 15
<212> TYPE: PRT
<213> ORGANISM: Artificial Sequence
<220> FEATURE:
<223> OTHER INFORMATION: Description of Artificial Sequence: Synthetic
      Linker sequence

<400> SEQUENCE: 37

Glu Pro Lys Ser Cys Asp Lys Thr His Thr Cys Pro Pro Cys Pro
1               5                   10                  15

<210> SEQ ID NO 38
<211> LENGTH: 24
<212> TYPE: PRT
<213> ORGANISM: Artificial Sequence
<220> FEATURE:
<223> OTHER INFORMATION: Description of Artificial Sequence: Synthetic
      Linker sequence

<400> SEQUENCE: 38

Gly Gly Gly Gly Ser Gly Gly Gly Ser Glu Pro Lys Ser Cys Asp Lys
1               5                   10                  15

Thr His Thr Cys Pro Pro Cys Pro
            20

<210> SEQ ID NO 39
<211> LENGTH: 12
<212> TYPE: PRT
<213> ORGANISM: Artificial Sequence
<220> FEATURE:
<223> OTHER INFORMATION: Description of Artificial Sequence: Synthetic
      Linker sequence

<400> SEQUENCE: 39

Glu Pro Lys Thr Pro Lys Pro Gln Pro Ala Ala Ala
1               5                   10

<210> SEQ ID NO 40
<211> LENGTH: 62
<212> TYPE: PRT
<213> ORGANISM: Artificial Sequence
<220> FEATURE:
<223> OTHER INFORMATION: Description of Artificial Sequence: Synthetic
      Linker sequence

<400> SEQUENCE: 40

Glu Leu Lys Thr Pro Leu Gly Asp Thr Thr His Thr Cys Pro Arg Cys
1               5                   10                  15

Pro Glu Pro Lys Ser Cys Asp Thr Pro Pro Cys Pro Arg Cys Pro
            20                  25                  30

Glu Pro Lys Ser Cys Asp Thr Pro Pro Cys Pro Arg Cys Pro Glu
        35                  40                  45

Pro Lys Ser Cys Asp Thr Pro Pro Cys Pro Arg Cys Pro
    50                  55                  60

<210> SEQ ID NO 41
<211> LENGTH: 271
<212> TYPE: PRT
<213> ORGANISM: Artificial Sequence
<220> FEATURE:
<223> OTHER INFORMATION: Description of Artificial Sequence: Synthetic
      Polypeptide comprising an anti-Aggrecan ISVD and an anti-albumin
      ISVD

<400> SEQUENCE: 41

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Thr Phe Ile Ile Asn
            20                  25                  30

Val Val Arg Trp Tyr Arg Arg Thr Pro Gly Lys Gln Arg Glu Leu Val
        35                  40                  45

Ala Thr Ile Ser Ser Gly Gly Asn Ala Asn Tyr Val Asp Ser Val Arg
    50                  55                  60

Gly Arg Phe Ser Ile Ser Arg Asp Gly Ala Lys Asn Ala Val Asp Leu
65                  70                  75                  80

Gln Met Asn Gly Leu Lys Pro Glu Asp Thr Ala Val Tyr Tyr Cys Asn
                85                  90                  95

Val Pro Thr Thr His Tyr Gly Gly Val Tyr Tyr Gly Pro Tyr Trp Gly
            100                 105                 110

Gln Gly Thr Leu Val Thr Val Ser Ser Gly Gly Gly Ser Gly Gly
        115                 120                 125

Gly Gly Ser Gly Gly Gly Ser Gly Gly Gly Ser Gly Gly Gly
    130                 135                 140

Gly Ser Gly Gly Gly Ser Gly Gly Gly Ser Glu Val Gln Leu
145                 150                 155                 160

Val Glu Ser Gly Gly Gly Leu Val Gln Pro Gly Asn Ser Leu Arg Leu
                165                 170                 175

Ser Cys Ala Ala Ser Gly Phe Thr Phe Ser Ser Ala Val Met Ser Trp
            180                 185                 190

Val Arg Gln Ala Pro Gly Lys Gly Leu Glu Trp Val Ser Ser Ile Ser
        195                 200                 205

Gly Ser Gly Ser Asp Thr Leu Tyr Ala Asp Ser Val Lys Gly Arg Phe
    210                 215                 220

Thr Ile Ser Arg Asp Asn Ala Lys Thr Thr Leu Tyr Leu Gln Met Asn
225                 230                 235                 240

```
Ser Leu Arg Pro Glu Asp Thr Ala Val Tyr Tyr Cys Thr Ile Gly Gly
            245                 250                 255

Ser Leu Ser Arg Ser Ser Gln Gly Thr Leu Val Thr Val Ser Ser
        260                 265                 270

<210> SEQ ID NO 42
<211> LENGTH: 427
<212> TYPE: PRT
<213> ORGANISM: Artificial Sequence
<220> FEATURE:
<223> OTHER INFORMATION: Description of Artificial Sequence: Synthetic
      Polypeptide comprising an anti-albumin ISVD and two anti-Aggrecan
      ISVDs

<400> SEQUENCE: 42

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Ala
            20                  25                  30

Val Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser Gly Gly Gly Gly Ser Gly Gly Gly Gly Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser Glu Val Gln Leu Val Glu Ser Gly Gly Gly
145                 150                 155                 160

Leu Val Gln Ala Gly Gly Ser Leu Arg Leu Ser Cys Ala Ala Ser Gly
                165                 170                 175

Ser Thr Phe Ile Ile Asn Val Val Arg Trp Tyr Arg Arg Thr Pro Gly
            180                 185                 190

Lys Gln Arg Glu Leu Val Ala Thr Ile Ser Ser Gly Gly Asn Ala Asn
        195                 200                 205

Tyr Val Asp Ser Val Arg Gly Arg Phe Ser Ile Ser Arg Asp Gly Ala
    210                 215                 220

Lys Asn Ala Val Asp Leu Gln Met Asn Gly Leu Lys Pro Glu Asp Thr
225                 230                 235                 240

Ala Val Tyr Tyr Cys Asn Val Pro Thr Thr His Tyr Gly Gly Val Tyr
                245                 250                 255

Tyr Gly Pro Tyr Trp Gly Gln Gly Thr Leu Val Thr Val Ser Ser Gly
            260                 265                 270

Gly Gly Ser Gly Gly Gly Gly Ser Gly Gly Gly Gly Ser Gly Gly Gly
        275                 280                 285

Gly Ser Gly Gly Gly Gly Ser Gly Gly Gly Gly Ser Gly Gly Gly Gly
    290                 295                 300

Gly Ser Glu Val Gln Leu Val Glu Ser Gly Gly Gly Leu Val Gln Ala
305                 310                 315                 320
```

```
Gly Gly Ser Leu Arg Leu Ser Cys Ala Ala Ser Gly Ser Thr Phe Ile
            325                 330                 335

Ile Asn Val Val Arg Trp Tyr Arg Thr Pro Gly Lys Gln Arg Glu
        340                 345                 350

Leu Val Ala Thr Ile Ser Ser Gly Gly Asn Ala Asn Tyr Val Asp Ser
            355                 360                 365

Val Arg Gly Arg Phe Ser Ile Ser Arg Asp Gly Ala Lys Asn Ala Val
        370                 375                 380

Asp Leu Gln Met Asn Gly Leu Lys Pro Glu Asp Thr Ala Val Tyr Tyr
385                 390                 395                 400

Cys Asn Val Pro Thr Thr His Tyr Gly Gly Val Tyr Tyr Gly Pro Tyr
                405                 410                 415

Trp Gly Gln Gly Thr Leu Val Thr Val Ser Ser
            420                 425
```

<210> SEQ ID NO 43
<211> LENGTH: 265
<212> TYPE: PRT
<213> ORGANISM: Artificial Sequence
<220> FEATURE:
<223> OTHER INFORMATION: Description of Artificial Sequence: Synthetic
      Polypeptide comprising two anti-albumin ISVDs

<400> SEQUENCE: 43

```
Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Ala
            20                  25                  30

Val Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser Gly Gly Gly Ser Gly Gly Gly Ser Gly Gly Gly Gly
        115                 120                 125

Gly Ser Gly Gly Gly Ser Gly Gly Gly Ser Gly Gly Gly Gly
    130                 135                 140

Ser Gly Gly Gly Ser Glu Val Gln Leu Val Glu Ser Gly Gly Gly
145                 150                 155                 160

Leu Val Gln Pro Gly Asn Ser Leu Arg Leu Ser Cys Ala Ala Ser Gly
                165                 170                 175

Phe Thr Phe Ser Ser Ala Val Met Ser Trp Val Arg Gln Ala Pro Gly
            180                 185                 190

Lys Gly Leu Glu Trp Val Ser Ser Ile Ser Gly Ser Gly Ser Asp Thr
        195                 200                 205

Leu Tyr Ala Asp Ser Val Lys Gly Arg Phe Thr Ile Ser Arg Asp Asn
    210                 215                 220

Ala Lys Thr Thr Leu Tyr Leu Gln Met Asn Ser Leu Arg Pro Glu Asp
225                 230                 235                 240

Thr Ala Val Tyr Tyr Cys Thr Ile Gly Gly Ser Leu Ser Arg Ser Ser
                245                 250                 255
```

Gln Gly Thr Leu Val Thr Val Ser Ser
        260                 265

<210> SEQ ID NO 44
<211> LENGTH: 115
<212> TYPE: PRT
<213> ORGANISM: Artificial Sequence
<220> FEATURE:
<223> OTHER INFORMATION: Description of Artificial Sequence: Synthetic
      Serum albumin binding ISVD

<400> SEQUENCE: 44

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 45
<211> LENGTH: 115
<212> TYPE: PRT
<213> ORGANISM: Artificial Sequence
<220> FEATURE:
<223> OTHER INFORMATION: Description of Artificial Sequence: Synthetic
      Serum albumin binding ISVD

<400> SEQUENCE: 45

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 46
<211> LENGTH: 116
<212> TYPE: PRT
<213> ORGANISM: Artificial Sequence
<220> FEATURE:
<223> OTHER INFORMATION: Description of Artificial Sequence: Synthetic
      Serum albumin binding ISVD

<400> SEQUENCE: 46

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Thr Tyr Tyr Cys
                85                  90                  95

Thr Ile Gly Gly Ser Leu Ser Arg Ser Ser Gln Gly Thr Leu Val Thr
            100                 105                 110

Val Ser Ser Ala
        115

<210> SEQ ID NO 47
<211> LENGTH: 116
<212> TYPE: PRT
<213> ORGANISM: Artificial Sequence
<220> FEATURE:
<223> OTHER INFORMATION: Description of Artificial Sequence: Synthetic
      Serum albumin binding ISVD

<400> SEQUENCE: 47

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Thr Tyr Tyr Cys
                85                  90                  95

Thr Ile Gly Gly Ser Leu Ser Arg Ser Ser Gln Gly Thr Leu Val Thr
            100                 105                 110

Val Ser Ser Ala
        115

<210> SEQ ID NO 48
<211> LENGTH: 115
<212> TYPE: PRT
<213> ORGANISM: Artificial Sequence
<220> FEATURE:
<223> OTHER INFORMATION: Description of Artificial Sequence: Synthetic
      Serum albumin binding ISVD

<400> SEQUENCE: 48

Glu Val Gln Leu Val Glu Ser Gly Gly Gly Leu Val Gln Pro Gly Asn
1               5                   10                  15

```
Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 49
<211> LENGTH: 116
<212> TYPE: PRT
<213> ORGANISM: Artificial Sequence
<220> FEATURE:
<223> OTHER INFORMATION: Description of Artificial Sequence: Synthetic
      Serum albumin binding ISVD

<400> SEQUENCE: 49

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Lys
            100                 105                 110

Val Ser Ser Ala
        115

<210> SEQ ID NO 50
<211> LENGTH: 115
<212> TYPE: PRT
<213> ORGANISM: Artificial Sequence
<220> FEATURE:
<223> OTHER INFORMATION: Description of Artificial Sequence: Synthetic
      Serum albumin binding ISVD

<400> SEQUENCE: 50

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60
```

```
Lys Gly Arg Phe Thr Ile Ser Arg Asp Asn Ala Lys Thr Thr Leu Tyr
 65                  70                  75                  80

Leu Gln Met Asn Ser Leu Arg Pro Glu Asp Thr Ala Leu Tyr Tyr Cys
                 85                  90                  95

Thr Ile Gly Gly Ser Leu Ser Arg Ser Ser Gln Gly Thr Leu Val Thr
            100                 105                 110

Val Ser Ser
        115

<210> SEQ ID NO 51
<211> LENGTH: 116
<212> TYPE: PRT
<213> ORGANISM: Artificial Sequence
<220> FEATURE:
<223> OTHER INFORMATION: Description of Artificial Sequence: Synthetic
      Serum albumin binding ISVD

<400> SEQUENCE: 51

Glu Val Gln Leu Val Glu Ser Gly Gly Gly Val Val Gln Pro Gly Asn
  1               5                  10                  15

Ser Leu Arg Leu Ser Cys Ala Ala Ser Gly Phe Thr Phe Ser Ser Phe
                 20                  25                  30

Gly Met Ser Trp Val Arg Gln Ala Pro Gly Lys Gly Leu Glu Trp Val
             35                  40                  45

Ser Ser Ile Ser Gly Ser Gly Ser Asp Thr Leu Tyr Ala Asp Ser Val
 50                  55                  60

Lys Gly Arg Phe Thr Ile Ser Arg Asp Asn Ala Lys Thr Thr Leu Tyr
 65                  70                  75                  80

Leu Gln Met Asn Ser Leu Arg Pro Glu Asp Thr Ala Leu Tyr Tyr Cys
                 85                  90                  95

Thr Ile Gly Gly Ser Leu Ser Arg Ser Ser Gln Gly Thr Leu Val Thr
            100                 105                 110

Val Ser Ser Ala
        115

<210> SEQ ID NO 52
<211> LENGTH: 117
<212> TYPE: PRT
<213> ORGANISM: Artificial Sequence
<220> FEATURE:
<223> OTHER INFORMATION: Description of Artificial Sequence: Synthetic
      Serum albumin binding ISVD

<400> SEQUENCE: 52

Glu Val Gln Leu Val Glu Ser Gly Gly Gly Val Val Gln Pro Gly Asn
  1               5                  10                  15

Ser Leu Arg Leu Ser Cys Ala Ala Ser Gly Phe Thr Phe Ser Ser Phe
                 20                  25                  30

Gly Met Ser Trp Val Arg Gln Ala Pro Gly Lys Gly Leu Glu Trp Val
             35                  40                  45

Ser Ser Ile Ser Gly Ser Gly Ser Asp Thr Leu Tyr Ala Asp Ser Val
 50                  55                  60

Lys Gly Arg Phe Thr Ile Ser Arg Asp Asn Ala Lys Thr Thr Leu Tyr
 65                  70                  75                  80

Leu Gln Met Asn Ser Leu Arg Pro Glu Asp Thr Ala Leu Tyr Tyr Cys
                 85                  90                  95

Thr Ile Gly Gly Ser Leu Ser Arg Ser Ser Gln Gly Thr Leu Val Thr
            100                 105                 110
```

```
Val Ser Ser Ala Ala
        115

<210> SEQ ID NO 53
<211> LENGTH: 118
<212> TYPE: PRT
<213> ORGANISM: Artificial Sequence
<220> FEATURE:
<223> OTHER INFORMATION: Description of Artificial Sequence: Synthetic
      Serum albumin binding ISVD

<400> SEQUENCE: 53

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser Ala Ala Ala
        115

<210> SEQ ID NO 54
<211> LENGTH: 116
<212> TYPE: PRT
<213> ORGANISM: Artificial Sequence
<220> FEATURE:
<223> OTHER INFORMATION: Description of Artificial Sequence: Synthetic
      Serum albumin binding ISVD

<400> SEQUENCE: 54

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser Gly
        115

<210> SEQ ID NO 55
<211> LENGTH: 117
<212> TYPE: PRT
<213> ORGANISM: Artificial Sequence
<220> FEATURE:
```

<223> OTHER INFORMATION: Description of Artificial Sequence: Synthetic
      Serum albumin binding ISVD

<400> SEQUENCE: 55

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser Gly Gly
        115

<210> SEQ ID NO 56
<211> LENGTH: 118
<212> TYPE: PRT
<213> ORGANISM: Artificial Sequence
<220> FEATURE:
<223> OTHER INFORMATION: Description of Artificial Sequence: Synthetic
      Serum albumin binding ISVD

<400> SEQUENCE: 56

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser Gly Gly Gly
        115

<210> SEQ ID NO 57
<211> LENGTH: 115
<212> TYPE: PRT
<213> ORGANISM: Artificial Sequence
<220> FEATURE:
<223> OTHER INFORMATION: Description of Artificial Sequence: Synthetic
      Serum albumin binding ISVD

<400> SEQUENCE: 57

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Ser Phe

```
                    20                  25                  30

Gly Met Ser Trp Val Arg Gln Ala Pro Gly Lys Gly Pro Glu Trp Val
            35                  40                  45

Ser Ser Ile Ser Gly Ser Gly Ser Asp Thr Leu Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 58
<211> LENGTH: 116
<212> TYPE: PRT
<213> ORGANISM: Artificial Sequence
<220> FEATURE:
<223> OTHER INFORMATION: Description of Artificial Sequence: Synthetic
      Serum albumin binding ISVD

<400> SEQUENCE: 58

Glu Val Gln Leu Val Glu Ser Gly Gly Gly Val Val Gln Pro Gly Gly
 1               5                  10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
            35                  40                  45

Ser Ser Ile Ser Gly Ser Gly Ser Asp Thr Leu Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser Ala
        115

<210> SEQ ID NO 59
<211> LENGTH: 5
<212> TYPE: PRT
<213> ORGANISM: Artificial Sequence
<220> FEATURE:
<223> OTHER INFORMATION: Description of Artificial Sequence: Synthetic
      Preferred CDR1 of Serum albumin binding ISVD

<400> SEQUENCE: 59

Ser Phe Gly Met Ser
 1               5

<210> SEQ ID NO 60
<211> LENGTH: 17
<212> TYPE: PRT
<213> ORGANISM: Artificial Sequence
<220> FEATURE:
<223> OTHER INFORMATION: Description of Artificial Sequence: Synthetic
      Preferred CDR2 of Serum albumin binding ISVD

<400> SEQUENCE: 60
```

```
Ser Ile Ser Gly Ser Gly Ser Asp Thr Leu Tyr Ala Asp Ser Val Lys
1               5                   10                  15

Gly

<210> SEQ ID NO 61
<211> LENGTH: 6
<212> TYPE: PRT
<213> ORGANISM: Artificial Sequence
<220> FEATURE:
<223> OTHER INFORMATION: Description of Artificial Sequence: Synthetic
      Preferred CDR3 of Serum albumin binding ISVD

<400> SEQUENCE: 61

Gly Gly Ser Leu Ser Arg
1               5

<210> SEQ ID NO 62
<211> LENGTH: 515
<212> TYPE: PRT
<213> ORGANISM: Artificial Sequence
<220> FEATURE:
<223> OTHER INFORMATION: Description of Artificial Sequence: Synthetic
      polypeptide comprising first ISVD binding MMP13, second ISVD
      binding ADAMTS5, third ISVD binding Aggrecan and fourth ISVD
      binding Aggrecan

<400> SEQUENCE: 62

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Ala Phe Ser Ala Ala
            20                  25                  30

Tyr Met Ser Trp Val Arg Gln Ala Pro Gly Lys Gly Leu Glu Trp Val
        35                  40                  45

Ser Ser Ile Ser Asp Asp Gly Ser Lys Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Asn Thr Gly Tyr Gly Ala Thr Thr Arg Pro Gly Arg Tyr Trp Gly
            100                 105                 110

Gln Gly Thr Leu Val Thr Val Ser Ser Gly Gly Gly Ser Gly Gly
        115                 120                 125

Gly Ser Glu Val Gln Leu Val Glu Ser Gly Gly Gly Val Val Gln Pro
    130                 135                 140

Gly Gly Ser Leu Arg Leu Ser Cys Ala Ala Ser Gly Arg Thr Val Ser
145                 150                 155                 160

Ser Tyr Ala Met Gly Trp Phe Arg Gln Ala Pro Gly Lys Glu Arg Glu
                165                 170                 175

Phe Val Ala Gly Ile Ser Arg Ser Ala Glu Arg Thr Tyr Tyr Val Asp
            180                 185                 190

Ser Leu Lys Gly Arg Phe Thr Ile Ser Arg Asp Asn Ser Lys Asn Thr
        195                 200                 205

Val Tyr Leu Gln Met Asn Ser Leu Arg Pro Glu Asp Thr Ala Leu Tyr
    210                 215                 220

Tyr Cys Ala Ala Asp Leu Asp Pro Asn Arg Ile Phe Ser Arg Glu Glu
225                 230                 235                 240

Tyr Ala Tyr Trp Gly Gln Gly Thr Leu Val Thr Val Ser Ser Gly Gly
```

```
            245                 250                 255
Gly Gly Ser Gly Gly Ser Glu Val Gln Leu Val Glu Ser Gly Gly
            260                 265                 270

Gly Val Val Gln Pro Gly Gly Ser Leu Arg Leu Ser Cys Ala Ala Ser
        275                 280                 285

Gly Ser Thr Phe Ile Ile Asn Val Val Arg Trp Tyr Arg Arg Ala Pro
    290                 295                 300

Gly Lys Gln Arg Glu Leu Val Ala Thr Ile Ser Ser Gly Gly Asn Ala
305                 310                 315                 320

Asn Tyr Val Asp Ser Val Arg Gly Arg Phe Thr Ile Ser Arg Asp Asn
                325                 330                 335

Ser Lys Asn Thr Val Tyr Leu Gln Met Asn Ser Leu Arg Pro Glu Asp
            340                 345                 350

Thr Ala Leu Tyr Tyr Cys Asn Val Pro Thr Thr His Tyr Gly Gly Val
        355                 360                 365

Tyr Tyr Gly Pro Tyr Trp Gly Gln Gly Thr Leu Val Thr Val Ser Ser
    370                 375                 380

Gly Gly Gly Gly Ser Gly Gly Ser Glu Val Gln Leu Val Glu Ser
385                 390                 395                 400

Gly Gly Gly Val Val Gln Pro Gly Gly Ser Leu Arg Leu Ser Cys Ala
                405                 410                 415

Ala Ser Gly Ser Thr Phe Ile Ile Asn Val Val Arg Trp Tyr Arg Arg
            420                 425                 430

Ala Pro Gly Lys Gln Arg Glu Leu Val Ala Thr Ile Ser Ser Gly Gly
        435                 440                 445

Asn Ala Asn Tyr Val Asp Ser Val Arg Gly Arg Phe Thr Ile Ser Arg
    450                 455                 460

Asp Asn Ser Lys Asn Thr Val Tyr Leu Gln Met Asn Ser Leu Arg Pro
465                 470                 475                 480

Glu Asp Thr Ala Leu Tyr Tyr Cys Asn Val Pro Thr Thr His Tyr Gly
                485                 490                 495

Gly Val Tyr Tyr Gly Pro Tyr Trp Gly Gln Gly Thr Leu Val Thr Val
            500                 505                 510

Ser Ser Ala
    515

<210> SEQ ID NO 63
<211> LENGTH: 382
<212> TYPE: PRT
<213> ORGANISM: Artificial Sequence
<220> FEATURE:
<223> OTHER INFORMATION: Description of Artificial Sequence: Synthetic
      polypeptide comprising first ISVD binding MMP13, second ISVD
      binding Aggrecan and third ISVD binding Aggrecan

<400> SEQUENCE: 63

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Ala Phe Ser Ala Ala
            20                  25                  30

Tyr Met Ser Trp Val Arg Gln Ala Pro Gly Lys Gly Leu Glu Trp Val
        35                  40                  45

Ser Ser Ile Ser Asp Asp Gly Ser Lys Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80
```

```
Leu Gln Met Asn Ser Leu Arg Pro Glu Asp Thr Ala Leu Tyr Tyr Cys
                85                  90                  95

Asn Thr Gly Tyr Gly Ala Thr Thr Thr Arg Pro Gly Arg Tyr Trp Gly
            100                 105                 110

Gln Gly Thr Leu Val Thr Val Ser Ser Gly Gly Gly Gly Ser Gly Gly
        115                 120                 125

Gly Ser Glu Val Gln Leu Val Glu Ser Gly Gly Gly Val Val Gln Pro
    130                 135                 140

Gly Gly Ser Leu Arg Leu Ser Cys Ala Ala Ser Gly Ser Thr Phe Ile
145                 150                 155                 160

Ile Asn Val Val Arg Trp Tyr Arg Arg Ala Pro Gly Lys Gln Arg Glu
                165                 170                 175

Leu Val Ala Thr Ile Ser Ser Gly Gly Asn Ala Asn Tyr Val Asp Ser
            180                 185                 190

Val Arg Gly Arg Phe Thr Ile Ser Arg Asp Asn Ser Lys Asn Thr Val
        195                 200                 205

Tyr Leu Gln Met As

```
Ala Gly Ile Ser Arg Ser Ala Glu Arg Thr Tyr Tyr Val Asp Ser Leu
    50                  55                  60
Lys Gly Arg Phe Thr Ile Ser Arg Asp Asn Ser Lys Asn Thr Val Tyr
65                  70                  75                  80
Leu Gln Met Asn Ser Leu Arg Pro Glu Asp Thr Ala Leu Tyr Tyr Cys
                85                  90                  95
Ala Ala Asp Leu Asp Pro Asn Arg Ile Phe Ser Arg Glu Glu Tyr Ala
            100                 105                 110
Tyr Trp Gly Gln Gly Thr Leu Val Thr Val Ser Ser Gly Gly Gly Gly
        115                 120                 125
Ser Gly Gly Gly Ser Glu Val Gln Leu Val Glu Ser Gly Gly Gly Val
    130                 135                 140
Val Gln Pro Gly Gly Ser Leu Arg Leu Ser Cys Ala Ala Ser Gly Ser
145                 150                 155                 160
Thr Phe Ile Ile Asn Val Val Arg Trp Tyr Arg Arg Ala Pro Gly Lys
                165                 170                 175
Gln Arg Glu Leu Val Ala Thr Ile Ser Ser Gly Gly Asn Ala Asn Tyr
            180                 185                 190
Val Asp Ser Val Arg Gly Arg Phe Thr Ile Ser Arg Asp Asn Ser Lys
        195                 200                 205
Asn Thr Val Tyr Leu Gln Met Asn Ser Leu Arg Pro Glu Asp Thr Ala
    210                 215                 220
Leu Tyr Tyr Cys Asn Val Pro Thr Thr His Tyr Gly Gly Val Tyr Tyr
225                 230                 235                 240
Gly Pro Tyr Trp Gly Gln Gly Thr Leu Val Thr Val Ser Ser Gly Gly
                245                 250                 255
Gly Gly Ser Gly Gly Gly Ser Glu Val Gln Leu Val Glu Ser Gly Gly
            260                 265                 270
Gly Val Val Gln Pro Gly Gly Ser Leu Arg Leu Ser Cys Ala Ala Ser
        275                 280                 285
Gly Ser Thr Phe Ile Ile Asn Val Val Arg Trp Tyr Arg Arg Ala Pro
    290                 295                 300
Gly Lys Gln Arg Glu Leu Val Ala Thr Ile Ser Ser Gly Gly Asn Ala
305                 310                 315                 320
Asn Tyr Val Asp Ser Val Arg Gly Arg Phe Thr Ile Ser Arg Asp Asn
                325                 330                 335
Ser Lys Asn Thr Val Tyr Leu Gln Met Asn Ser Leu Arg Pro Glu Asp
            340                 345                 350
Thr Ala Leu Tyr Tyr Cys Asn Val Pro Thr Thr His Tyr Gly Gly Val
        355                 360                 365
Tyr Tyr Gly Pro Tyr Trp Gly Gln Gly Thr Leu Val Thr Val Ser Ser
    370                 375                 380
Ala
385

<210> SEQ ID NO 65
<211> LENGTH: 275
<212> TYPE: PRT
<213> ORGANISM: Artificial Sequence
<220> FEATURE:
<223> OTHER INFORMATION: Description of Artificial Sequence: Synthetic
      ADAMTS5 inhibiting polypeptide which does not contain a
      CAP-binding moiety

<400> SEQUENCE: 65

Asp Val Gln Leu Val Glu Ser Gly Gly Gly Val Val Gln Pro Gly Gly
```

-continued

```
            1               5                  10                 15
           Ser Leu Arg Leu Ser Cys Ala Ala Ser Gly Arg Thr Val Ser Ser Tyr
                           20                 25                 30

Ala Met Gly Trp Phe Arg Gln Ala Pro Gly Lys Glu Arg Glu Phe Val
                           35                 40                 45

Ala Gly Ile Ser Arg Ser Ala Glu Arg Thr Tyr Tyr Val Asp Ser Leu
                           50                 55                 60

Lys Gly Arg Phe Thr Ile Ser Arg Asp Asn Ser Lys Asn Thr Val Tyr
            65                 70                 75                 80

Leu Gln Met Asn Ser Leu Arg Pro Glu Asp Thr Ala Leu Tyr Tyr Cys
                           85                 90                 95

Ala Ala Asp Leu Asp Pro Asn Arg Ile Phe Ser Arg Glu Glu Tyr Ala
                          100                105                110

Tyr Trp Gly Gln Gly Thr Leu Val Thr Val Ser Gly Gly Gly Gly
                          115                120                125

Ser Gly Gly Gly Gly Ser Gly Gly Gly Ser Gly Gly Gly Gly Ser
                          130                135                140

Gly Gly Gly Gly Ser Gly Gly Gly Ser Gly Gly Gly Gly Ser Glu
           145                150                155                160

Val Gln Leu Val Glu Ser Gly Gly Val Val Gln Pro Gly Asn Ser
                          165                170                175

Leu Arg Leu Ser Cys Ala Ala Ser Gly Phe Thr Phe Ser Ser Phe Gly
                          180                185                190

Met Ser Trp Val Arg Gln Ala Pro Gly Lys Gly Leu Glu Trp Val Ser
                          195                200                205

Ser Ile Ser Gly Ser Gly Ser Asp Thr Leu Tyr Ala Asp Ser Val Lys
                          210                215                220

Gly Arg Phe Thr Ile Ser Arg Asp Asn Ala Lys Thr Thr Leu Tyr Leu
           225                230                235                240

Gln Met Asn Ser Leu Arg Pro Glu Asp Thr Ala Leu Tyr Tyr Cys Thr
                          245                250                255

Ile Gly Gly Ser Leu Ser Arg Ser Ser Gln Gly Thr Leu Val Thr Val
                          260                265                270

Ser Ser Ala
                          275

<210> SEQ ID NO 66
<211> LENGTH: 471
<212> TYPE: PRT
<213> ORGANISM: Homo sapiens
<220> FEATURE:
<221> NAME/KEY: MISC_FEATURE
<222> LOCATION: (1)..(471)
<223> OTHER INFORMATION: Human MMP13

<400> SEQUENCE: 66

Met His Pro Gly Val Leu Ala Ala Phe Leu Phe Leu Ser Trp Thr His
 1               5                 10                 15

Cys Arg Ala Leu Pro Leu Pro Ser Gly Gly Asp Glu Asp Asp Leu Ser
                20                 25                 30

Glu Glu Asp Leu Gln Phe Ala Glu Arg Tyr Leu Arg Ser Tyr Tyr His
                35                 40                 45

Pro Thr Asn Leu Ala Gly Ile Leu Lys Glu Asn Ala Ala Ser Ser Met
           50                 55                 60

Thr Glu Arg Leu Arg Glu Met Gln Ser Phe Phe Gly Leu Glu Val Thr
 65                 70                 75                 80
```

Gly Lys Leu Asp Asp Asn Thr Leu Asp Val Met Lys Pro Arg Cys
            85                  90                  95

Gly Val Pro Asp Val Gly Glu Tyr Asn Val Phe Pro Arg Thr Leu Lys
                100                 105                 110

Trp Ser Lys Met Asn Leu Thr Tyr Arg Ile Val Asn Tyr Thr Pro Asp
            115                 120                 125

Met Thr His Ser Glu Val Glu Lys Ala Phe Lys Ala Phe Lys Val
130                 135                 140

Trp Ser Asp Val Thr Pro Leu Asn Phe Thr Arg Leu His Asp Gly Ile
145                 150                 155                 160

Ala Asp Ile Met Ile Ser Phe Gly Ile Lys Glu His Gly Asp Phe Tyr
                165                 170                 175

Pro Phe Asp Gly Pro Ser Gly Leu Leu Ala His Ala Phe Pro Pro Gly
            180                 185                 190

Pro Asn Tyr Gly Gly Asp Ala His Phe Asp Asp Glu Thr Trp Thr
            195                 200                 205

Ser Ser Ser Lys Gly Tyr Asn Leu Phe Leu Val Ala Ala His Glu Phe
    210                 215                 220

Gly His Ser Leu Gly Leu Asp His Ser Lys Asp Pro Gly Ala Leu Met
225                 230                 235                 240

Phe Pro Ile Tyr Thr Tyr Thr Gly Lys Ser His Phe Met Leu Pro Asp
                245                 250                 255

Asp Asp Val Gln Gly Ile Gln Ser Leu Tyr Gly Pro Gly Asp Glu Asp
            260                 265                 270

Pro Asn Pro Lys His Pro Lys Thr Pro Asp Lys Cys Asp Pro Ser Leu
            275                 280                 285

Ser Leu Asp Ala Ile Thr Ser Leu Arg Gly Glu Thr Met Ile Phe Lys
    290                 295                 300

Asp Arg Phe Phe Trp Arg Leu His Pro Gln Gln Val Asp Ala Glu Leu
305                 310                 315                 320

Phe Leu Thr Lys Ser Phe Trp Pro Glu Leu Pro Asn Arg Ile Asp Ala
                325                 330                 335

Ala Tyr Glu His Pro Ser His Asp Leu Ile Phe Ile Phe Arg Gly Arg
            340                 345                 350

Lys Phe Trp Ala Leu Asn Gly Tyr Asp Ile Leu Glu Gly Tyr Pro Lys
            355                 360                 365

Lys Ile Ser Glu Leu Gly Leu Pro Lys Glu Val Lys Lys Ile Ser Ala
    370                 375                 380

Ala Val His Phe Glu Asp Thr Gly Lys Thr Leu Leu Phe Ser Gly Asn
385                 390                 395                 400

Gln Val Trp Arg Tyr Asp Asp Thr Asn His Ile Met Asp Lys Asp Tyr
                405                 410                 415

Pro Arg Leu Ile Glu Glu Asp Phe Pro Gly Ile Gly Asp Lys Val Asp
            420                 425                 430

Ala Val Tyr Glu Lys Asn Gly Tyr Ile Tyr Phe Phe Asn Gly Pro Ile
            435                 440                 445

Gln Phe Glu Tyr Ser Ile Trp Ser Asn Arg Ile Val Arg Val Met Pro
    450                 455                 460

Ala Asn Ser Ile Leu Trp Cys
465                 470

<210> SEQ ID NO 67
<211> LENGTH: 930

```
<212> TYPE: PRT
<213> ORGANISM: Homo sapiens
<220> FEATURE:
<221> NAME/KEY: MISC_FEATURE
<222> LOCATION: (1)..(930)
<223> OTHER INFORMATION: Human ADAMTS5

<400> SEQUENCE: 67
```

Met Leu Leu Gly Trp Ala Ser Leu Leu Leu Cys Ala Phe Arg Leu Pro
1               5                   10                  15

Leu Ala Ala Val Gly Pro Ala Ala Thr Pro Ala Gln Asp Lys Ala Gly
            20                  25                  30

Gln Pro Pro Thr Ala Ala Ala Ala Gln Pro Arg Arg Arg Gln Gly
        35                  40                  45

Glu Glu Val Gln Glu Arg Ala Glu Pro Pro Gly His Pro His Pro Leu
50                  55                  60

Ala Gln Arg Arg Arg Ser Lys Gly Leu Val Gln Asn Ile Asp Gln Leu
65                  70                  75                  80

Tyr Ser Gly Gly Lys Val Gly Tyr Leu Val Tyr Ala Gly Gly Arg
                85                  90                  95

Arg Phe Leu Leu Asp Leu Glu Arg Asp Gly Ser Val Gly Ile Ala Gly
            100                 105                 110

Phe Val Pro Ala Gly Gly Gly Thr Ser Ala Pro Trp Arg His Arg Ser
        115                 120                 125

His Cys Phe Tyr Arg Gly Thr Val Asp Gly Ser Pro Arg Ser Leu Ala
130                 135                 140

Val Phe Asp Leu Cys Gly Gly Leu Asp Gly Phe Phe Ala Val Lys His
145                 150                 155                 160

Ala Arg Tyr Thr Leu Lys Pro Leu Leu Arg Gly Pro Trp Ala Glu Glu
                165                 170                 175

Glu Lys Gly Arg Val Tyr Gly Asp Gly Ser Ala Arg Ile Leu His Val
            180                 185                 190

Tyr Thr Arg Glu Gly Phe Ser Phe Glu Ala Leu Pro Pro Arg Ala Ser
        195                 200                 205

Cys Glu Thr Pro Ala Ser Thr Pro Glu Ala His Glu His Ala Pro Ala
210                 215                 220

His Ser Asn Pro Ser Gly Arg Ala Ala Leu Ala Ser Gln Leu Leu Asp
225                 230                 235                 240

Gln Ser Ala Leu Ser Pro Ala Gly Gly Ser Gly Pro Gln Thr Trp Trp
                245                 250                 255

Arg Arg Arg Arg Arg Ser Ile Ser Arg Ala Arg Gln Val Glu Leu Leu
            260                 265                 270

Leu Val Ala Asp Ala Ser Met Ala Arg Leu Tyr Gly Arg Gly Leu Gln
        275                 280                 285

His Tyr Leu Leu Thr Leu Ala Ser Ile Ala Asn Arg Leu Tyr Ser His
290                 295                 300

Ala Ser Ile Glu Asn His Ile Arg Leu Ala Val Val Lys Val Val
305                 310                 315                 320

Leu Gly Asp Lys Asp Lys Ser Leu Glu Val Ser Lys Asn Ala Ala Thr
                325                 330                 335

Thr Leu Lys Asn Phe Cys Lys Trp Gln His Gln His Asn Gln Leu Gly
            340                 345                 350

Asp Asp His Glu Glu His Tyr Asp Ala Ala Ile Leu Phe Thr Arg Glu
        355                 360                 365

Asp Leu Cys Gly His His Ser Cys Asp Thr Leu Gly Met Ala Asp Val

```
                370             375             380
Gly Thr Ile Cys Ser Pro Glu Arg Ser Cys Ala Val Ile Glu Asp Asp
385             390             395             400

Gly Leu His Ala Ala Phe Thr Val Ala His Glu Ile Gly His Leu Leu
                405             410             415

Gly Leu Ser His Asp Asp Ser Lys Phe Cys Glu Glu Thr Phe Gly Ser
                420             425             430

Thr Glu Asp Lys Arg Leu Met Ser Ser Ile Leu Thr Ser Ile Asp Ala
            435             440             445

Ser Lys Pro Trp Ser Lys Cys Thr Ser Ala Thr Ile Thr Glu Phe Leu
            450             455             460

Asp Asp Gly His Gly Asn Cys Leu Leu Asp Leu Pro Arg Lys Gln Ile
465             470             475             480

Leu Gly Pro Glu Glu Leu Pro Gly Gln Thr Tyr Asp Ala Thr Gln Gln
                485             490             495

Cys Asn Leu Thr Phe Gly Pro Glu Tyr Ser Val Cys Pro Gly Met Asp
                500             505             510

Val Cys Ala Arg Leu Trp Cys Ala Val Val Arg Gln Gly Gln Met Val
            515             520             525

Cys Leu Thr Lys Lys Leu Pro Ala Val Glu Gly Thr Pro Cys Gly Lys
            530             535             540

Gly Arg Ile Cys Leu Gln Gly Lys Cys Val Asp Lys Thr Lys Lys Lys
545             550             555             560

Tyr Tyr Ser Thr Ser Ser His Gly Asn Trp Gly Ser Trp Gly Ser Trp
                565             570             575

Gly Gln Cys Ser Arg Ser Cys Gly Gly Val Gln Phe Ala Tyr Arg
                580             585             590

His Cys Asn Asn Pro Ala Pro Arg Asn Asn Gly Arg Tyr Cys Thr Gly
            595             600             605

Lys Arg Ala Ile Tyr Arg Ser Cys Ser Leu Met Pro Cys Pro Pro Asn
            610             615             620

Gly Lys Ser Phe Arg His Glu Gln Cys Glu Ala Lys Asn Gly Tyr Gln
625             630             635             640

Ser Asp Ala Lys Gly Val Lys Thr Phe Val Glu Trp Val Pro Lys Tyr
                645             650             655

Ala Gly Val Leu Pro Ala Asp Val Cys Lys Leu Thr Cys Arg Ala Lys
                660             665             670

Gly Thr Gly Tyr Tyr Val Val Phe Ser Pro Lys Val Thr Asp Gly Thr
                675             680             685

Glu Cys Arg Leu Tyr Ser Asn Ser Val Cys Val Arg Gly Lys Cys Val
            690             695             700

Arg Thr Gly Cys Asp Gly Ile Ile Gly Ser Lys Leu Gln Tyr Asp Lys
705             710             715             720

Cys Gly Val Cys Gly Gly Asp Asn Ser Ser Cys Thr Lys Ile Val Gly
                725             730             735

Thr Phe Asn Lys Lys Ser Lys Gly Tyr Thr Asp Val Val Arg Ile Pro
                740             745             750

Glu Gly Ala Thr His Ile Lys Val Arg Gln Phe Lys Ala Lys Asp Gln
            755             760             765

Thr Arg Phe Thr Ala Tyr Leu Ala Leu Lys Lys Lys Asn Gly Glu Tyr
            770             775             780

Leu Ile Asn Gly Lys Tyr Met Ile Ser Thr Ser Glu Thr Ile Ile Asp
785             790             795             800
```

-continued

```
Ile Asn Gly Thr Val Met Asn Tyr Ser Gly Trp Ser His Arg Asp Asp
                805                 810                 815

Phe Leu His Gly Met Gly Tyr Ser Ala Thr Lys Glu Ile Leu Ile Val
            820                 825                 830

Gln Ile Leu Ala Thr Asp Pro Thr Lys Pro Leu Asp Val Arg Tyr Ser
            835                 840                 845

Phe Phe Val Pro Lys Lys Ser Thr Pro Lys Val Asn Ser Val Thr Ser
850                 855                 860

His Gly Ser Asn Lys Val Gly Ser His Thr Ser Gln Pro Gln Trp Val
865                 870                 875                 880

Thr Gly Pro Trp Leu Ala Cys Ser Arg Thr Cys Asp Thr Gly Trp His
            885                 890                 895

Thr Arg Thr Val Gln Cys Gln Asp Gly Asn Arg Lys Leu Ala Lys Gly
            900                 905                 910

Cys Pro Leu Ser Gln Arg Pro Ser Ala Phe Lys Gln Cys Leu Leu Lys
            915                 920                 925

Lys Cys
    930

<210> SEQ ID NO 68
<211> LENGTH: 2415
<212> TYPE: PRT
<213> ORGANISM: Homo sapiens
<220> FEATURE:
<221> NAME/KEY: MISC_FEATURE
<222> LOCATION: (1)..(2415)
<223> OTHER INFORMATION: Human Aggrecan

<400> SEQUENCE: 68

Met Thr Thr Leu Leu Trp Val Phe Val Thr Leu Arg Val Ile Thr Ala
1               5                   10                  15

Ala Val Thr Val Glu Thr Ser Asp His Asp Asn Ser Leu Ser Val Ser
            20                  25                  30

Ile Pro Gln Pro Ser Pro Leu Arg Val Leu Leu Gly Thr Ser Leu Thr
            35                  40                  45

Ile Pro Cys Tyr Phe Ile Asp Pro Met His Pro Val Thr Thr Ala Pro
    50                  55                  60

Ser Thr Ala Pro Leu Ala Pro Arg Ile Lys Trp Ser Arg Val Ser Lys
65                  70                  75                  80

Glu Lys Glu Val Val Leu Leu Val Ala Thr Glu Gly Arg Val Arg Val
                85                  90                  95

Asn Ser Ala Tyr Gln Asp Lys Val Ser Leu Pro Asn Tyr Pro Ala Ile
            100                 105                 110

Pro Ser Asp Ala Thr Leu Glu Val Gln Ser Leu Arg Ser Asn Asp Ser
            115                 120                 125

Gly Val Tyr Arg Cys Glu Val Met His Gly Ile Glu Asp Ser Glu Ala
    130                 135                 140

Thr Leu Glu Val Val Val Lys Gly Ile Val Phe His Tyr Arg Ala Ile
145                 150                 155                 160

Ser Thr Arg Tyr Thr Leu Asp Phe Asp Arg Ala Gln Arg Ala Cys Leu
                165                 170                 175

Gln Asn Ser Ala Ile Ile Ala Thr Pro Glu Gln Leu Gln Ala Ala Tyr
            180                 185                 190

Glu Asp Gly Phe His Gln Cys Asp Ala Gly Trp Leu Ala Asp Gln Thr
            195                 200                 205
```

```
Val Arg Tyr Pro Ile His Thr Pro Arg Glu Gly Cys Tyr Gly Asp Lys
210                 215                 220

Asp Glu Phe Pro Gly Val Arg Thr Tyr Gly Ile Arg Asp Thr Asn Glu
225                 230                 235                 240

Thr Tyr Asp Val Tyr Cys Phe Ala Glu Glu Met Glu Gly Glu Val Phe
                245                 250                 255

Tyr Ala Thr Ser Pro Glu Lys Phe Thr Phe Gln Glu Ala Ala Asn Glu
                260                 265                 270

Cys Arg Arg Leu Gly Ala Arg Leu Ala Thr Thr Gly His Val Tyr Leu
                275                 280                 285

Ala Trp Gln Ala Gly Met Asp Met Cys Ser Ala Gly Trp Leu Ala Asp
290                 295                 300

Arg Ser Val Arg Tyr Pro Ile Ser Lys Ala Arg Pro Asn Cys Gly Gly
305                 310                 315                 320

Asn Leu Leu Gly Val Arg Thr Val Tyr Val His Ala Asn Gln Thr Gly
                325                 330                 335

Tyr Pro Asp Pro Ser Ser Arg Tyr Asp Ala Ile Cys Tyr Thr Gly Glu
                340                 345                 350

Asp Phe Val Asp Ile Pro Glu Asn Phe Phe Gly Val Gly Gly Glu Glu
                355                 360                 365

Asp Ile Thr Val Gln Thr Val Thr Trp Pro Asp Met Glu Leu Pro Leu
                370                 375                 380

Pro Arg Asn Ile Thr Glu Gly Glu Ala Arg Gly Ser Val Ile Leu Thr
385                 390                 395                 400

Val Lys Pro Ile Phe Glu Val Ser Pro Ser Pro Leu Glu Pro Glu Glu
                405                 410                 415

Pro Phe Thr Phe Ala Pro Glu Ile Gly Ala Thr Ala Phe Ala Glu Val
                420                 425                 430

Glu Asn Glu Thr Gly Glu Ala Thr Arg Pro Trp Gly Phe Pro Thr Pro
                435                 440                 445

Gly Leu Gly Pro Ala Thr Ala Phe Thr Ser Glu Asp Leu Val Val Gln
                450                 455                 460

Val Thr Ala Val Pro Gly Gln Pro His Leu Pro Gly Gly Val Val Phe
465                 470                 475                 480

His Tyr Arg Pro Gly Pro Thr Arg Tyr Ser Leu Thr Phe Glu Glu Ala
                485                 490                 495

Gln Gln Ala Cys Pro Gly Thr Gly Ala Val Ile Ala Ser Pro Glu Gln
                500                 505                 510

Leu Gln Ala Ala Tyr Glu Ala Gly Tyr Glu Gln Cys Asp Ala Gly Trp
                515                 520                 525

Leu Arg Asp Gln Thr Val Arg Tyr Pro Ile Val Ser Pro Arg Thr Pro
530                 535                 540

Cys Val Gly Asp Lys Asp Ser Ser Pro Gly Val Arg Thr Tyr Gly Val
545                 550                 555                 560

Arg Pro Ser Thr Glu Thr Tyr Asp Val Tyr Cys Phe Val Asp Arg Leu
                565                 570                 575

Glu Gly Glu Val Phe Phe Ala Thr Arg Leu Glu Gln Phe Thr Phe Gln
                580                 585                 590

Glu Ala Leu Glu Phe Cys Glu Ser His Asn Ala Thr Ala Thr Thr Gly
                595                 600                 605

Gln Leu Tyr Ala Ala Trp Ser Arg Gly Leu Asp Lys Cys Tyr Ala Gly
                610                 615                 620

Trp Leu Ala Asp Gly Ser Leu Arg Tyr Pro Ile Val Thr Pro Arg Pro
```

```
                625                 630                 635                 640
Ala Cys Gly Gly Asp Lys Pro Gly Val Arg Thr Val Tyr Leu Tyr Pro
                    645                 650                 655

Asn Gln Thr Gly Leu Pro Asp Pro Leu Ser Arg His His Ala Phe Cys
                660                 665                 670

Phe Arg Gly Ile Ser Ala Val Pro Ser Pro Gly Glu Glu Gly Gly
            675                 680                 685

Thr Pro Thr Ser Pro Ser Gly Val Glu Glu Trp Ile Val Thr Gln Val
        690                 695                 700

Val Pro Gly Val Ala Ala Val Pro Val Glu Glu Thr Thr Ala Val
705                 710                 715                 720

Pro Ser Gly Glu Thr Thr Ala Ile Leu Glu Phe Thr Thr Glu Pro Glu
                725                 730                 735

Asn Gln Thr Glu Trp Glu Pro Ala Tyr Thr Pro Val Gly Thr Ser Pro
                740                 745                 750

Leu Pro Gly Ile Leu Pro Thr Trp Pro Pro Thr Gly Ala Glu Thr Glu
            755                 760                 765

Glu Ser Thr Glu Gly Pro Ser Ala Thr Glu Val Pro Ser Ala Ser Glu
        770                 775                 780

Glu Pro Ser Pro Ser Glu Val Pro Phe Pro Ser Glu Pro Ser Pro
785                 790                 795                 800

Ser Glu Glu Pro Phe Pro Ser Val Arg Pro Phe Pro Ser Val Glu Leu
                805                 810                 815

Phe Pro Ser Glu Glu Pro Phe Pro Ser Lys Glu Pro Ser Pro Ser Glu
            820                 825                 830

Glu Pro Ser Ala Ser Glu Glu Pro Tyr Thr Pro Ser Pro Pro Glu Pro
        835                 840                 845

Ser Trp Thr Glu Leu Pro Ser Ser Gly Glu Glu Ser Gly Ala Pro Asp
    850                 855                 860

Val Ser Gly Asp Phe Thr Gly Ser Gly Asp Val Ser Gly His Leu Asp
865                 870                 875                 880

Phe Ser Gly Gln Leu Ser Gly Asp Arg Ala Ser Gly Leu Pro Ser Gly
                885                 890                 895

Asp Leu Asp Ser Ser Gly Leu Thr Ser Thr Val Gly Ser Gly Leu Thr
            900                 905                 910

Val Glu Ser Gly Leu Pro Ser Gly Asp Glu Glu Arg Ile Glu Trp Pro
        915                 920                 925

Ser Thr Pro Thr Val Gly Glu Leu Pro Ser Gly Ala Glu Ile Leu Glu
    930                 935                 940

Gly Ser Ala Ser Gly Val Gly Asp Leu Ser Gly Leu Pro Ser Gly Glu
945                 950                 955                 960

Val Leu Glu Thr Ser Ala Ser Gly Val Gly Asp Leu Ser Gly Leu Pro
                965                 970                 975

Ser Gly Glu Val Leu Glu Thr Thr Ala Pro Gly Val Glu Asp Ile Ser
            980                 985                 990

Gly Leu Pro Ser Gly Glu Val Leu  Glu Thr Thr Ala Pro  Gly Val Glu
        995                 1000                1005

Asp Ile  Ser Gly Leu Pro Ser  Gly Glu Val Leu Glu  Thr Thr Ala
    1010                1015                1020

Pro Gly  Val Glu Asp Ile Ser  Gly Leu Pro Ser Gly  Glu Val Leu
    1025                1030                1035

Glu Thr  Thr Ala Pro Gly Val  Glu Asp Ile Ser Gly  Leu Pro Ser
    1040                1045                1050
```

```
Gly Glu Val Leu Glu Thr Thr Ala Pro Gly Val Glu Asp Ile Ser
    1055                1060                1065

Gly Leu Pro Ser Gly Glu Val Leu Glu Thr Ala Ala Pro Gly Val
    1070                1075                1080

Glu Asp Ile Ser Gly Leu Pro Ser Gly Glu Val Leu Glu Thr Ala
    1085                1090                1095

Ala Pro Gly Val Glu Asp Ile Ser Gly Leu Pro Ser Gly Glu Val
    1100                1105                1110

Leu Glu Thr Ala Ala Pro Gly Val Glu Asp Ile Ser Gly Leu Pro
    1115                1120                1125

Ser Gly Glu Val Leu Glu Thr Ala Ala Pro Gly Val Glu Asp Ile
    1130                1135                1140

Ser Gly Leu Pro Ser Gly Glu Val Leu Glu Thr Ala Ala Pro Gly
    1145                1150                1155

Val Glu Asp Ile Ser Gly Leu Pro Ser Gly Glu Val Leu Glu Thr
    1160                1165                1170

Ala Ala Pro Gly Val Glu Asp Ile Ser Gly Leu Pro Ser Gly Glu
    1175                1180                1185

Val Leu Glu Thr Ala Ala Pro Gly Val Glu Asp Ile Ser Gly Leu
    1190                1195                1200

Pro Ser Gly Glu Val Leu Glu Thr Ala Ala Pro Gly Val Glu Asp
    1205                1210                1215

Ile Ser Gly Leu Pro Ser Gly Glu Val Leu Glu Thr Ala Ala Pro
    1220                1225                1230

Gly Val Glu Asp Ile Ser Gly Leu Pro Ser Gly Glu Val Leu Glu
    1235                1240                1245

Thr Ala Ala Pro Gly Val Glu Asp Ile Ser Gly Leu Pro Ser Gly
    1250                1255                1260

Glu Val Leu Glu Thr Ala Ala Pro Gly Val Glu Asp Ile Ser Gly
    1265                1270                1275

Leu Pro Ser Gly Glu Val Leu Glu Thr Thr Ala Pro Gly Val Glu
    1280                1285                1290

Glu Ile Ser Gly Leu Pro Ser Gly Glu Val Leu Glu Thr Thr Ala
    1295                1300                1305

Pro Gly Val Asp Glu Ile Ser Gly Leu Pro Ser Gly Glu Val Leu
    1310                1315                1320

Glu Thr Thr Ala Pro Gly Val Glu Glu Ile Ser Gly Leu Pro Ser
    1325                1330                1335

Gly Glu Val Leu Glu Thr Ser Thr Ser Ala Val Gly Asp Leu Ser
    1340                1345                1350

Gly Leu Pro Ser Gly Gly Glu Val Leu Glu Ile Ser Val Ser Gly
    1355                1360                1365

Val Glu Asp Ile Ser Gly Leu Pro Ser Gly Glu Val Val Glu Thr
    1370                1375                1380

Ser Ala Ser Gly Ile Glu Asp Val Ser Glu Leu Pro Ser Gly Glu
    1385                1390                1395

Gly Leu Glu Thr Ser Ala Ser Gly Val Glu Asp Leu Ser Arg Leu
    1400                1405                1410

Pro Ser Gly Glu Glu Val Leu Glu Ile Ser Ala Ser Gly Phe Gly
    1415                1420                1425

Asp Leu Ser Gly Val Pro Ser Gly Gly Glu Gly Leu Glu Thr Ser
    1430                1435                1440
```

```
Ala Ser Glu Val Gly Thr Asp Leu Ser Gly Leu Pro Ser Gly Arg
1445                1450                1455
Glu Gly Leu Glu Thr Ser Ala Ser Gly Ala Glu Asp Leu Ser Gly
1460                1465                1470
Leu Pro Ser Gly Lys Glu Asp Leu Val Gly Ser Ala Ser Gly Asp
1475                1480                1485
Leu Asp Leu Gly Lys Leu Pro Ser Gly Thr Leu Gly Ser Gly Gln
1490                1495                1500
Ala Pro Glu Thr Ser Gly Leu Pro Ser Gly Phe Ser Gly Glu Tyr
1505                1510                1515
Ser Gly Val Asp Leu Gly Ser Gly Pro Pro Ser Gly Leu Pro Asp
1520                1525                1530
Phe Ser Gly Leu Pro Ser Gly Phe Pro Thr Val Ser Leu Val Asp
1535                1540                1545
Ser Thr Leu Val Glu Val Val Thr Ala Ser Thr Ala Ser Glu Leu
1550                1555                1560
Glu Gly Arg Gly Thr Ile Gly Ile Ser Gly Ala Gly Glu Ile Ser
1565                1570                1575
Gly Leu Pro Ser Ser Glu Leu Asp Ile Ser Gly Arg Ala Ser Gly
1580                1585                1590
Leu Pro Ser Gly Thr Glu Leu Ser Gly Gln Ala Ser Gly Ser Pro
1595                1600                1605
Asp Val Ser Gly Glu Ile Pro Gly Leu Phe Gly Val Ser Gly Gln
1610                1615                1620
Pro Ser Gly Phe Pro Asp Thr Ser Gly Glu Thr Ser Gly Val Thr
1625                1630                1635
Glu Leu Ser Gly Leu Ser Ser Gly Gln Pro Gly Val Ser Gly Glu
1640                1645                1650
Ala Ser Gly Val Leu Tyr Gly Thr Ser Gln Pro Phe Gly Ile Thr
1655                1660                1665
Asp Leu Ser Gly Glu Thr Ser Gly Val Pro Asp Leu Ser Gly Gln
1670                1675                1680
Pro Ser Gly Leu Pro Gly Phe Ser Gly Ala Thr Ser Gly Val Pro
1685                1690                1695
Asp Leu Val Ser Gly Thr Thr Ser Gly Ser Gly Glu Ser Ser Gly
1700                1705                1710
Ile Thr Phe Val Asp Thr Ser Leu Val Glu Val Ala Pro Thr Thr
1715                1720                1725
Phe Lys Glu Glu Glu Gly Leu Gly Ser Val Glu Leu Ser Gly Leu
1730                1735                1740
Pro Ser Gly Glu Ala Asp Leu Ser Gly Lys Ser Gly Met Val Asp
1745                1750                1755
Val Ser Gly Gln Phe Ser Gly Thr Val Asp Ser Ser Gly Phe Thr
1760                1765                1770
Ser Gln Thr Pro Glu Phe Ser Gly Leu Pro Ser Gly Ile Ala Glu
1775                1780                1785
Val Ser Gly Glu Ser Ser Arg Ala Glu Ile Gly Ser Ser Leu Pro
1790                1795                1800
Ser Gly Ala Tyr Tyr Gly Ser Gly Thr Pro Ser Ser Phe Pro Thr
1805                1810                1815
Val Ser Leu Val Asp Arg Thr Leu Val Glu Ser Val Thr Gln Ala
1820                1825                1830
Pro Thr Ala Gln Glu Ala Gly Glu Gly Pro Ser Gly Ile Leu Glu
```

```
                1835                1840                1845
Leu Ser Gly Ala His Ser Gly Ala Pro Asp Met Ser Gly Glu His
    1850                1855                1860
Ser Gly Phe Leu Asp Leu Ser Gly Leu Gln Ser Gly Leu Ile Glu
    1865                1870                1875
Pro Ser Gly Glu Pro Pro Gly Thr Pro Tyr Phe Ser Gly Asp Phe
    1880                1885                1890
Ala Ser Thr Thr Asn Val Ser Gly Glu Ser Ser Val Ala Met Gly
    1895                1900                1905
Thr Ser Gly Glu Ala Ser Gly Leu Pro Glu Val Thr Leu Ile Thr
    1910                1915                1920
Ser Glu Phe Val Glu Gly Val Thr Glu Pro Thr Ile Ser Gln Glu
    1925                1930                1935
Leu Gly Gln Arg Pro Pro Val Thr His Thr Pro Gln Leu Phe Glu
    1940                1945                1950
Ser Ser Gly Lys Val Ser Thr Ala Gly Asp Ile Ser Gly Ala Thr
    1955                1960                1965
Pro Val Leu Pro Gly Ser Gly Val Glu Val Ser Ser Val Pro Glu
    1970                1975                1980
Ser Ser Ser Glu Thr Ser Ala Tyr Pro Glu Ala Gly Phe Gly Ala
    1985                1990                1995
Ser Ala Ala Pro Glu Ala Ser Arg Glu Asp Ser Gly Ser Pro Asp
    2000                2005                2010
Leu Ser Glu Thr Thr Ser Ala Phe His Glu Ala Asn Leu Glu Arg
    2015                2020                2025
Ser Ser Gly Leu Gly Val Ser Gly Ser Thr Leu Thr Phe Gln Glu
    2030                2035                2040
Gly Glu Ala Ser Ala Ala Pro Glu Val Ser Gly Glu Ser Thr Thr
    2045                2050                2055
Thr Ser Asp Val Gly Thr Glu Ala Pro Gly Leu Pro Ser Ala Thr
    2060                2065                2070
Pro Thr Ala Ser Gly Asp Arg Thr Glu Ile Ser Gly Asp Leu Ser
    2075                2080                2085
Gly His Thr Ser Gln Leu Gly Val Val Ile Ser Thr Ser Ile Pro
    2090                2095                2100
Glu Ser Glu Trp Thr Gln Gln Thr Gln Arg Pro Ala Glu Thr His
    2105                2110                2115
Leu Glu Ile Glu Ser Ser Ser Leu Leu Tyr Ser Gly Glu Glu Thr
    2120                2125                2130
His Thr Val Glu Thr Ala Thr Ser Pro Thr Asp Ala Ser Ile Pro
    2135                2140                2145
Ala Ser Pro Glu Trp Lys Arg Glu Ser Glu Ser Thr Ala Ala Ala
    2150                2155                2160
Pro Ala Arg Ser Cys Ala Glu Glu Pro Cys Gly Ala Gly Thr Cys
    2165                2170                2175
Lys Glu Thr Glu Gly His Val Ile Cys Leu Cys Pro Pro Gly Tyr
    2180                2185                2190
Thr Gly Glu His Cys Asn Ile Asp Gln Glu Val Cys Glu Glu Gly
    2195                2200                2205
Trp Asn Lys Tyr Gln Gly His Cys Tyr Arg His Phe Pro Asp Arg
    2210                2215                2220
Glu Thr Trp Val Asp Ala Glu Arg Arg Cys Arg Glu Gln Gln Ser
    2225                2230                2235
```

```
His Leu Ser Ser Ile Val Thr Pro Glu Glu Gln Glu     Phe Val Asn
    2240            2245            2250

Asn Asn Ala Gln Asp Tyr Gln Trp Ile Gly Leu Asn     Asp Arg Thr
    2255            2260            2265

Ile Glu Gly Asp Phe Arg Trp Ser Asp Gly His Pro     Met Gln Phe
    2270            2275            2280

Glu Asn Trp Arg Pro Asn Gln Pro Asp Asn Phe Phe     Ala Ala Gly
    2285            2290            2295

Glu Asp Cys Val Val Met Ile Trp His Glu Lys Gly     Glu Trp Asn
    2300            2305            2310

Asp Val Pro Cys Asn Tyr His Leu Pro Phe Thr Cys     Lys Lys Gly
    2315            2320            2325

Thr Val Ala Cys Gly Glu Pro Pro Val Val Glu His     Ala Arg Thr
    2330            2335            2340

Phe Gly Gln Lys Lys Asp Arg Tyr Glu Ile Asn Ser     Leu Val Arg
    2345            2350            2355

Tyr Gln Cys Thr Glu Gly Phe Val Gln Arg His Met     Pro Thr Ile
    2360            2365            2370

Arg Cys Gln Pro Ser Gly His Trp Glu Glu Pro Arg     Ile Thr Cys
    2375            2380            2385

Thr Asp Ala Thr Thr Tyr Lys Arg Arg Leu Gln Lys     Arg Ser Ser
    2390            2395            2400

Arg His Pro Arg Arg Ser Arg Pro Ser Thr Ala His
    2405            2410            2415
```

POLYPEPTIDES BINDING ADAMTS5, MMP13 AND AGGRECAN

RELATED APPLICATIONS

The present application claims priority under 37 U.S.C. § 371 to International Patent Application No. PCT/EP2018/064668, filed Jun. 4, 2018, which claims priority to and the benefit of European Patent Application No. 17174404.8, filed on Jun. 2, 2017. The contents of these applications are hereby incorporated by reference in their entireties.

SEQUENCE LISTING

The instant application contains a Sequence Listing which has been submitted in ASCII format via EFS-Web and is hereby incorporated by reference in its entirety. Said ASCII copy, is named 134067-0400_ST25, was created on 8 Jun. 2023 and is 103,773 bytes in size.

1 FIELD OF THE INVENTION

The present invention relates to polypeptides binding Aggrecan as well as ADAMTS5 and/or MMP13, more in particular to polypeptides that comprise or essentially consist of immunoglobulins binding Aggrecan as well as immunoglobulins binding ADAMTS5 and/or immunoglobulins binding MMP13 (also referred to herein as "polypeptides of the invention", and "immunoglobulin(s) of the invention", respectively). The invention also relates to constructs comprising such immunoglobulins, such as immunoglobulin single variable domains (ISVDs) or polypeptides as well as nucleic acids encoding such immunoglobulins or polypeptides (also referred to herein as "nucleic acid(s) of the invention"; to methods for preparing such immunoglobulins, polypeptides and constructs; to host cells expressing or capable of expressing such immunoglobulins or polypeptides; to compositions, and in particular to pharmaceutical compositions, that comprise such immunoglobulins, polypeptides, constructs, nucleic acids and/or host cells; and to uses of immunoglobulins, polypeptides, constructs, nucleic acids, host cells and/or compositions, in particular for prophylactic and/or therapeutic purposes, such as the prophylactic and/or therapeutic purposes mentioned herein. Other aspects, embodiments, advantages and applications of the invention will become clear from the further description herein.

2 BACKGROUND OF THE INVENTION

Osteoarthritis (OA) is one of the most common causes of disability worldwide. It affects 30 million Americans and is the most common joint disorder. It is projected to affect more than 20 percent of the U.S. population by 2025. The disease is non-systemic and is usually restricted to a few joints. However, the disease can occur in all joints, most often the knees, hips, hands and spine. OA is characterized by progressive erosion of articular cartilage (cartilage that covers the bones) resulting in chronic pain and disability. Eventually, the disease leads to the total destruction of the articular cartilage, sclerosis of underlying bone, osteophyte formation etc., all leading to loss of movement and pain. Osteoarthritis can be defined as a diverse group of conditions characterised by a combination of joint symptoms, signs stemming from defects in the articular cartilage and changes in adjacent tissues including bone, tendons and muscle. The most prominent symptom of OA is pain and this most often the reason patients seek medical help. There is no cure for OA, i.e. current treatments do not inhibit structural deterioration of the OA joint. Disease management is limited to treatments that are palliative at best and do little to address the underlying cause of disease progression.

Disease modifying anti-osteoarthritic drugs (DMOADs), which can be defined as drugs that inhibit structural disease progression and ideally also improve symptoms and/or function are intensely sought after. DMOADs are likely to be prescribed for long periods in this chronic illness of an aging population, therefore demanding excellent safety data in a target population with multiple comorbidities and the potential for drug-drug interactions.

Although disease initiation may be multi-factorial, the cartilage destruction appears to be a result of uncontrolled proteolytic destruction of the extracellular matrix (ECM). The most abundant ECM components of articular cartilage are Collagen (foremost Collagen II) and the proteoglycans, mainly Aggrecan (Kiani et al. 2002 Cell Research 12:19-32).

Aggrecan is important in the proper functioning of the articular cartilage because it provides a hydrated gel structure that endows the cartilage with load-bearing properties. Aggrecan is a large, multinodular molecule (2317 amino acids) expressed by chondrocytes. Its core protein is composed of three globular domains (G1, G2 and G3) and a large extended region between G2 and G3 for glycosaminoglycan chain attachment. This extended region comprises two domains, one substituted with keratan sulfate chains (KS domain) and one with chondroitin sulfate chains (CS domain). The CS domain has 100-150 glycosaminoglycan (GAG) chains attached to it. Aggrecan forms large complexes with Hyaluronan in which 50-100 Aggrecan molecules interact via the G1 domain and Link Protein with one Hyaluronan molecule. Upon uptake of water (due to the GAG content) these complexes form a reversibly deformable gel that resists compression. The structure, fluid retention and function of joint cartilage is linked to the matrix content of Aggrecan, and the amount of chondroitin sulfate bound to the intact core protein. Structurally, OA is characterized by degradation of Aggrecan, progressively releasing domains G3 and G2 (resulting in 'deflation' of the cartilage) and eventually release of the G1 domain and degradation of Collagen, irreversibly destroying the cartilage structure. The most significant Aggrecan cleavage site in OA pathogenesis is located at the sequence TEGE$^{373}\downarrow^{374}$ARGS. This cleavage site is positioned in the interglobular domain (IGD) of Aggrecan, located between the G1 and G2 domains.

Antibodies that recognize the $^{374}$ARGS neo-epitope led to the discovery of aggrecanase-1, which proved to be ADAMTS4 and aggrecanase-2, which is ADAMTS5. Subsequently, other related ADAMTS enzymes, including ADAMTS1, −8, −9, −15 and −20, were shown to have aggrecanase activity. ADAMTS16 and 18 are also weak aggrecanases. Various lines of evidence indicate that ADAMTS5 is a principal enzyme involved in the pathogenesis of osteoarthritis. In human cartilage explants and chondrocytes, knockdown of ADAMTS5 attenuated Aggrecan breakdown, suggesting that this enzyme may be involved in human tissues. Expression of the enzyme is augmented by cytokines such as interleukin-1 and oncostatin-M, which provoke Aggrecan breakdown in tissues. ADAMTS5-generated Aggrecan fragments are detected in the synovial fluid and serum of OA patients (Germaschewski et al., 2014 Osteoarthritis Cartilage 22:690-697). Several pharmaceutical companies have been developing DMOADs. Some of these compounds are claimed to be specific for ADAMTS5, whereas others have effect also against other ADAMTS members, or even against matrix metalloproteinases. These cross-inhibitions against MMPs in particular are considered to be responsible for musculoskeletal syndrome (MSS), a side effect caused by broad-spectrum inhibitors and involving arthralgia, myalgia, joint stiffness and tendonitis (Santamaria et al., 2015 Biochem J 471:391-401). These side effects were a reason for halting further development. The Pfizer aggrecanase inhibitor AGG-523 was used in a phase I clinical trial in OA, but has not been taken further. Nor have the other small molecule ADAMTS inhibitors entered any further clinical development as potential DMOAD (Bondeson et al., 2015 Drug Discovery 10:5-14). The Galapagos/Servier ADAMTS5 inhibitor GLPG1972 has recently finished a phase I trial, but its efficacy is yet to be determined. Indeed, despite a number of recent clinical trials specifically investigating DMOADs, no such treatments have been approved so far (El Bakali et al., 2014 Future Medicinal Chemistry (Review) 6:1399). A study of the Rottapharm monoclonal antibody (mAb) CRB0017, directed against the spacer domain of ADAMTS5, showed that in mice, intra-articular administration of this mAb significantly prevented disease progression in a dose-dependent manner (Chiusaroli et al., 2013 Osteoarthritis Cartilage 21:1807). There was, however, no comparison with systemic administration, nor was it assessed to what degree the mAb leaked from the synovial space. Another study used systemic administration of the mAb 12F4 in mice, which demonstrated both structural disease modification and alleviation of pain-related behaviour (Miller et al., 2014 Osteoarthritis Cartilage 22iii, S35). However, a single administration of mAb 12F4 in cynomolgus monkey caused focal haemorrhage, a dose-dependent increased mean arterial pressure and cardiac conductance abnormalities (more specifically, ST elevations and ventricular arrhythmias on the ECG) indicating cardiac ischemia, which were sustained for up to 8 months after administration of the single dose (Larkin et al., 2014 Osteoarthritis Cartilage 22iii, S483). Also in this case, the side effects halted further clinical development of mAb 12F4.

Next to the ADAMTS enzymes, there is compelling evidence that also the matrix metalloproteinases (MMPs) have a major role in tissue destruction associated with OA. MMPs are a family of zinc-dependent endopeptidases involved in the degradation of extracellular matrix and tissue remodeling.

There are some 28 MMP family members, which can be classified into various subgroups including collagenases, gelatinases, stromelysins, membrane-type MMPs, matrilysins, enamelysins and others. The collagenases, comprising MMP1, MMP8, MMP13 and MMP18, are capable of degrading triple-helical fibrillar Collagens into distinctive ¾ and ¼ fragments. In addition, MMP14 has also been shown to cleave fibrillar Collagen, and there is evidence that also MMP2 is capable of collagenolysis. MMPs have long been considered as attractive therapeutic targets for treatment of OA. However, as mentioned above, broad-spectrum MMP inhibitors developed for treatment of arthritis have failed in clinical trials due to painful, joint-stiffening side effects, i.e. MSS.

Therapeutic interventions in joints have further been hindered by the difficulty of targeting drugs to articular cartilage. Because articular cartilage is an avascular and alymphatic tissue, traditional routes of drug delivery (oral, intravenous, intramuscular) ultimately rely on transsynovial transfer of drugs from the synovial capillaries to cartilage by passive diffusion. This prompted the development of intra-articular (IA) delivery of medicaments. Although IA delivery circumvented the problem of passive diffusion, IA delivery of therapeutic proteins has been limited by their rapid clearance from the joint space and foremost lack of retention within cartilage. Notably, synovial residence time of a drug in the joint is often less than 24 h (Edwards 2011 Vet J 190:15-21; Larsen et al., 2008 J Pham Sci 97:4622-4654). Due to the rapid clearance of most IA injected drugs, frequent injections would be needed to maintain an effective concentration (Owen et al., 1994 Br J Clin Pharmacol 38:349-355). However, frequent IA-injections are undesired due to the pain and discomfort they may cause challenging patient compliance, as well as the risk of introducing joint infections.

There remains a need for effective DMOADs.

3 SUMMARY OF THE INVENTION

The present invention aims to provide polypeptides and constructs against OA with improved prophylactic, therapeutic and/or pharmacological properties, in addition to other advantageous properties (such as, for example, improved ease of preparation, good stability, and/or reduced costs of goods), compared to the prior art amino acid sequences and antibodies. In particular, the present invention aims to provide polypeptides inhibiting ADAMTS5 and/or MMP13, while being retained for extended periods in the joints.

Realizing that osteoarthritis does not evolve uniformly and that the pace of lesion progression can be very variable—in extreme cases, osteoarthritis may remain stable for decades, while in other patients the OA progresses very rapidly to complete destruction of the cartilage in the space of a few months—, the present inventors hypothesized (without being bound by theory, however) that such a variable disease progression pattern may be due to an inhomogeneous activity pattern of various proteases.

After identifying effective protease inhibitors from different families and cartilage anchoring moieties by creative and unconventional screening, characterization and combinatory strategies, the present inventors developed combinations in which various functionalities were joined. Two dual-specific polypeptides were engineered comprising cartilage anchoring moieties binding Aggrecan (CAP) and either an ADAMTS5 inhibitor or an MMP13 inhibitor, as well as tri-specific polypeptides comprising an ADAMTS5 inhibitor, an MMP13 inhibitor and CAP binders.

It was demonstrated that the polypeptides of the invention remained effective in various model systems, representing different OA states, even when the benchmark molecules (Wyeth and Pfizer) were not.

The present inventors were able to identify and re-engineer CAP binders that remained effective even when combined with two other moieties. It was also demonstrated that the CAP moiety of polypeptides of the invention resulted in an increased retention in the joint.

It was also demonstrated that the polypeptides of the invention remained stable in the joint.

Hence, the polypeptides of the present invention would on the one hand be broadly useful in OA patients, while on the other hand the burden of the (IA) administration schedule would be eased. In addition, by combining the various moieties in one molecule the effective dose can be increased.

Accordingly, the present invention relates to a polypeptide chosen from the group consisting of (a) polypeptides comprising at least 2 immunoglobulin single variable domains (ISVD), in which a first ISVD specifically binds a matrix metalloproteinase (MMP) and a second ISVD specifically binds Aggrecan, and optionally comprising a third ISVD specifically binding Aggrecan; (b) polypeptides comprising at least 2 ISVDs, in which a first ISVD specifically binds an A Disintegrin and Metalloproteinase with Thrombospondin motifs (ADAMTS) and a second ISVD specifically binds Aggrecan, and optionally comprising a third ISVD specifically binding Aggrecan; and (c) polypeptides comprising at least 3 ISVDs, in which a first ISVD specifically binds an MMP, a second ISVD specifically binds an ADAMTS and a third ISVD specifically binds Aggrecan, and optionally comprising a fourth ISVD specifically binding Aggrecan.

In an aspect the present invention relates to a polypeptide as described herein, in which a first ISVD specifically binds an MMP, a second ISVD specifically binds an ADAMTS, a third ISVD specifically binds Aggrecan and a fourth ISVD specifically binds Aggrecan, preferably said MMP is MMP13.

In one aspect the present invention provides an ISVD as described herein, wherein said ISVD has the structure FR1-CDR1-FR2-CDR2-FR3-CDR3-FR4, in which CDR1, CDR2 and CDR3 are as defined herein, and FR1, FR2, FR3 and FR4 are framework sequences.

In an aspect the present invention relates to a polypeptide as described herein, wherein said ISVD specifically binding MMP13 essentially consists of 4 framework regions (FR1 to FR4, respectively) and 3 complementarity determining regions (CDR1 to CDR3 respectively), in which (i) (a) CDR1 is SEQ ID NO: 8; and (b) amino acid sequences that have 1, 2 or 3 amino acid difference(s) with SEQ ID NO: 8; (ii) (c) CDR2 is SEQ ID NO: 10; and (d) amino acid sequences that have 1, 2 or 3 amino acid difference(s) with SEQ ID NO: 10; and (iii) (e) CDR3 is SEQ ID NO: 12; and (f) amino acid sequences that have 1, 2 or 3 amino acid difference(s) with SEQ ID NO: 12; preferably in which CDR1 is SEQ ID NO: 8, CDR2 is SEQ ID NO: 10 and CDR3 is SEQ ID NO: 12; even more preferably wherein said ISVD specifically binding MMP13 is represented by SEQ ID NO: 2.

In an aspect the present invention relates to a polypeptide as described herein, wherein said ADAMTS is ADAMTS5, preferably, wherein said ISVD specifically binding ADAMTS5 essentially consists of 4 framework regions (FR1 to FR4, respectively) and 3 complementarity determining regions (CDR1 to CDR3 respectively), in which (i) (a) CDR1 is SEQ ID NO: 14 [GRTVSSYAMG]; and (b) amino acid sequences that have 1, 2 or 3 amino acid difference(s) with SEQ ID NO: 14; (ii) (c) CDR2 is SEQ ID NO: 16 [GISRSAERTY]; and (d) amino acid sequences that have 1, 2 or 3 amino acid difference(s) with SEQ ID NO: 16; and (iii) (e) CDR3 is SEQ ID NO: 18 [DLDPNRIFSREEYAY]; and (f) amino acid sequences that have 1, 2 or 3 amino acid difference(s) with SEQ ID NO: 18; even more preferably, in which CDR1 is SEQ ID NO: 14, CDR2 is SEQ ID NO: 16 and CDR3 is SEQ ID NO: 18; and even more preferably, wherein said ISVD specifically binding ADAMTS5 is represented by SEQ ID NO: 3.

In an aspect the present invention relates to a polypeptide as described herein, wherein said ISVD specifically binding Aggrecan essentially consists of 4 framework regions (FR1 to FR4, respectively) and 3 complementarity determining regions (CDR1 to CDR3 respectively), in which (i) (a) CDR1 is SEQ ID NO: 19; and (b) amino acid sequences that have 1, 2 or 3 amino acid difference(s) with SEQ ID NO: 19; (ii) (c) CDR2 is SEQ ID NO: 21; and (d) amino acid sequences that have 1, 2 or 3 amino acid difference(s) with SEQ ID NO: 21; and (iii) (e) CDR3 is SEQ ID NO: 23; and (f) amino acid sequences that have 1, 2 or 3 amino acid difference(s) with SEQ ID NO: 23; more preferably, in which CDR1 is SEQ ID NO: 19, CDR2 is SEQ ID NO: 21 and CDR3 is SEQ ID NO: 23; even more preferably, wherein said ISVD specifically binding Aggrecan is represented by SEQ ID NO: 4.

In preferred embodiments of all aspects of the invention an immunoglobulin single variable domain (ISVD) according to the invention preferably consists of or essentially consists of 4 framework regions (FR1 to FR4, respectively) and 3 complementarity determining regions CDR1, CDR2 and CDR3 as outlined herein above and below. Preferred framework sequences are disclosed for example in the table A-2 below and can be used in an ISVD of the invention. Preferably, the CDRs depicted in Table A-2 are matched with the respective framework regions of the same ISVD construct.

In an aspect the present invention relates to a polypeptide as described herein, wherein said ISVDs are linked to each other via a linker, preferably said linker is chosen from the group consisting of SEQ ID NOs: 24 to 40, preferably SEQ ID NO: 28 [9GS] or SEQ ID NO: 35 [35GS].

In an aspect the present invention relates to a polypeptide as described herein, in which said first ISVD specifically binds MMP13, said second ISVD specifically binds ADAMTS5, said third ISVD specifically binds Aggrecan and said fourth ISVD specifically binds Aggrecan, preferably represented by SEQ ID NO: 1 or 62.

In an aspect the present invention relates to a polypeptide as described herein, in which said first ISVD specifically binds MMP13, said second ISVD specifically binds Aggrecan and said third ISVD specifically binds Aggrecan, preferably represented by SEQ ID NO: 5 or 63.

In an aspect the present invention relates to a polypeptide as described herein, in which said first ISVD specifically binds ADAMTS5, said second ISVD specifically binds Aggrecan, and said third ISVD specifically binds Aggrecan, preferably represented by SEQ ID NO: 6 or 64.

In an aspect the present invention relates to a construct that comprises or essentially consists of a polypeptide as described herein, which further comprises one or more other groups, residues, moieties or binding units, optionally linked via one or more peptidic linkers.

In an aspect the present invention relates to a nucleic acid encoding a polypeptide as described herein, or a construct as described herein.

In an aspect the present invention relates to an expression vector comprising a nucleic acid as described herein.

In an aspect the present invention relates to a host or host cell comprising a nucleic acid as described herein, or an expression vector as described herein.

In an aspect the present invention relates to a composition comprising a polypeptide as described herein, a construct as described herein or a nucleic acid as described herein.

In an aspect the present invention relates to a method for producing a polypeptide as described herein., said method at least comprising the steps of: a) expressing, in a suitable host cell, host organism or suitable expression system, a nucleic acid as described herein; optionally followed by b) isolating and/or purifying the polypeptide as described herein.

In an aspect the present invention relates to a composition as described herein, which is a pharmaceutical composition, preferably said composition further comprises at least one pharmaceutically acceptable carrier, diluent or excipient and/or adjuvant, and optionally comprises one or more further pharmaceutically active polypeptides and/or compounds.

In an aspect the present invention relates to a composition as described herein, a polypeptide as described herein, or a construct as described herein, for use as a medicament.

In an aspect the present invention relates to a composition as described herein, a polypeptide as described herein, or a construct as described herein, for use in preventing a symptom of or treating arthropathies and chondrodystrophies, arthritic disease, such as osteoarthritis, rheumatoid arthritis, gouty arthritis, psoriatic arthritis, traumatic rupture or detachment, achondroplasia, costochondritis, Spondyloepimetaphyseal dysplasia, spinal disc herniation, lumbar disk degeneration disease, degenerative joint disease, relapsing polychondritis, osteochondritis dissecans, aggrecanopathies, NASH, chronic periodontitis and abdominal aortic aneurysms.

In an aspect the present invention relates to a method of preventing a symptom of or treating a disease or disorder in an individual, the method comprising administering a polypeptide as described herein, a construct as described herein or a composition as described herein to said individual in an amount effective to treat or prevent a symptom of arthropathies and chondrodystrophies, arthritic disease, such as osteoarthritis, rheumatoid arthritis, gouty arthritis, psoriatic arthritis, traumatic rupture or detachment, achondroplasia, costochondritis, Spondyloepimetaphyseal dysplasia, spinal disc herniation, lumbar disc degeneration disease, degenerative joint disease, relapsing polychondritis, osteochondritis dissecans, aggrecanopathies, NASH, chronic periodontitis and abdominal aortic aneurysms.

Other aspects, advantages, applications and uses of the polypeptides and compositions will become clear from the further disclosure herein. Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

4 FIGURE LEGENDS

FIG. 1: Functional inhibition of species ADAMTS5 by polypeptide 949 ("C010100949", SEQ ID NO: 1) in FRET-based enzymatic activity assay. $V_i$: velocity (progress curve slope) of the inhibited enzyme reaction; $V_0$: velocity of the uninhibited reaction. Each point represents the average of technical duplicate measurements. Error bars: standard deviation across the technical duplicates. This graph is representative of 3 independent experiments.

Figure 2:
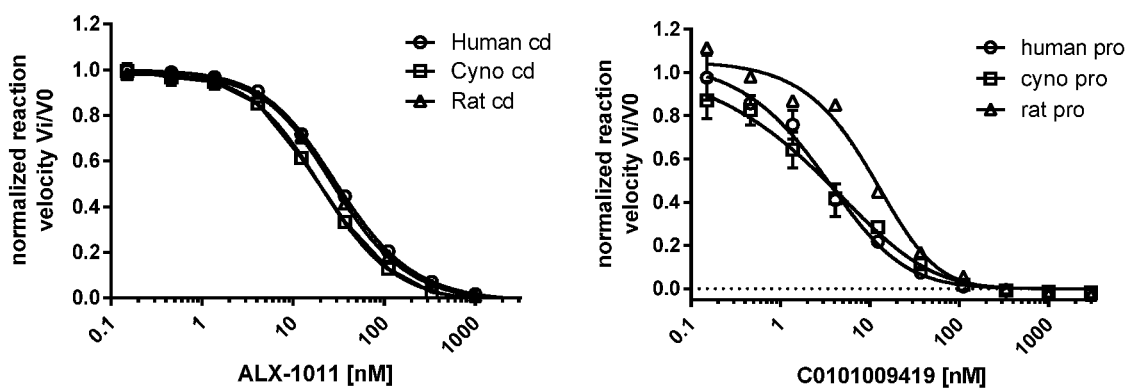

FIG. 2: Functional inhibition of human, cynomolgus and rat MMP13 by polypeptide 949 in FRET-based enzymatic activity assay. Left: Inhibition of species cdMMP13 by polypeptide 949 (ALX-1011). Right: Inhibition of species activated proMMP13 (polypeptide 949 is designated as C010100949). $V_i$: velocity (progress curve slope) of the inhibited enzyme reaction, $V_0$: velocity of the uninhibited reaction. Cd: catalytic domain; pro: activated pro-MMP13. Each point represents the average of technical duplicate measurements. Error bars: standard deviation across the technical duplicates. Figures are representative of at least two independent experiments.

Figure 3:
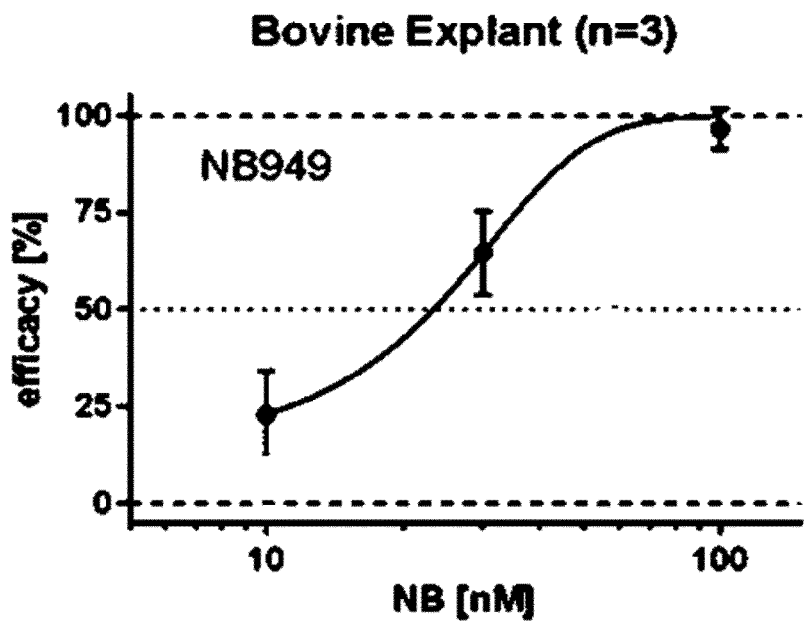

FIG. 3: Efficacy of polypeptide 949 ("NB949") in bovine cartilage explant assay. Efficacy was calculated as compared to a reference small molecule Aggrecanase inhibitor (AGG-523, Wyeth) which under these conditions fully inhibits the IL-1α stimulated GAG release, which was set at 100%, the non-induced cartilage was set at 0%.

Figure 4:
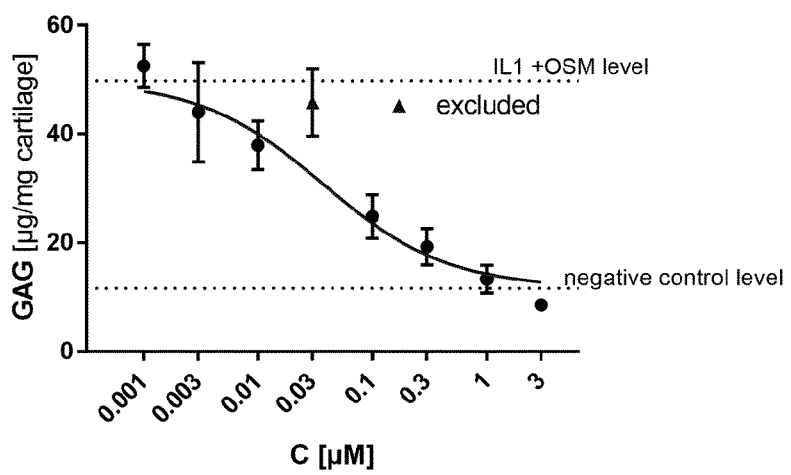

FIG. 4: Efficacy of polypeptide 949 in a human cartilage explant assay. Efficacy was calculated as compared to a reference small molecule Aggrecanase inhibitor (AGG-523, Wyeth) which under these conditions fully inhibits the IL-1α stimulated GAG release, which was set at 100%, the non-induced cartilage was set at 0%.

Figure 5:
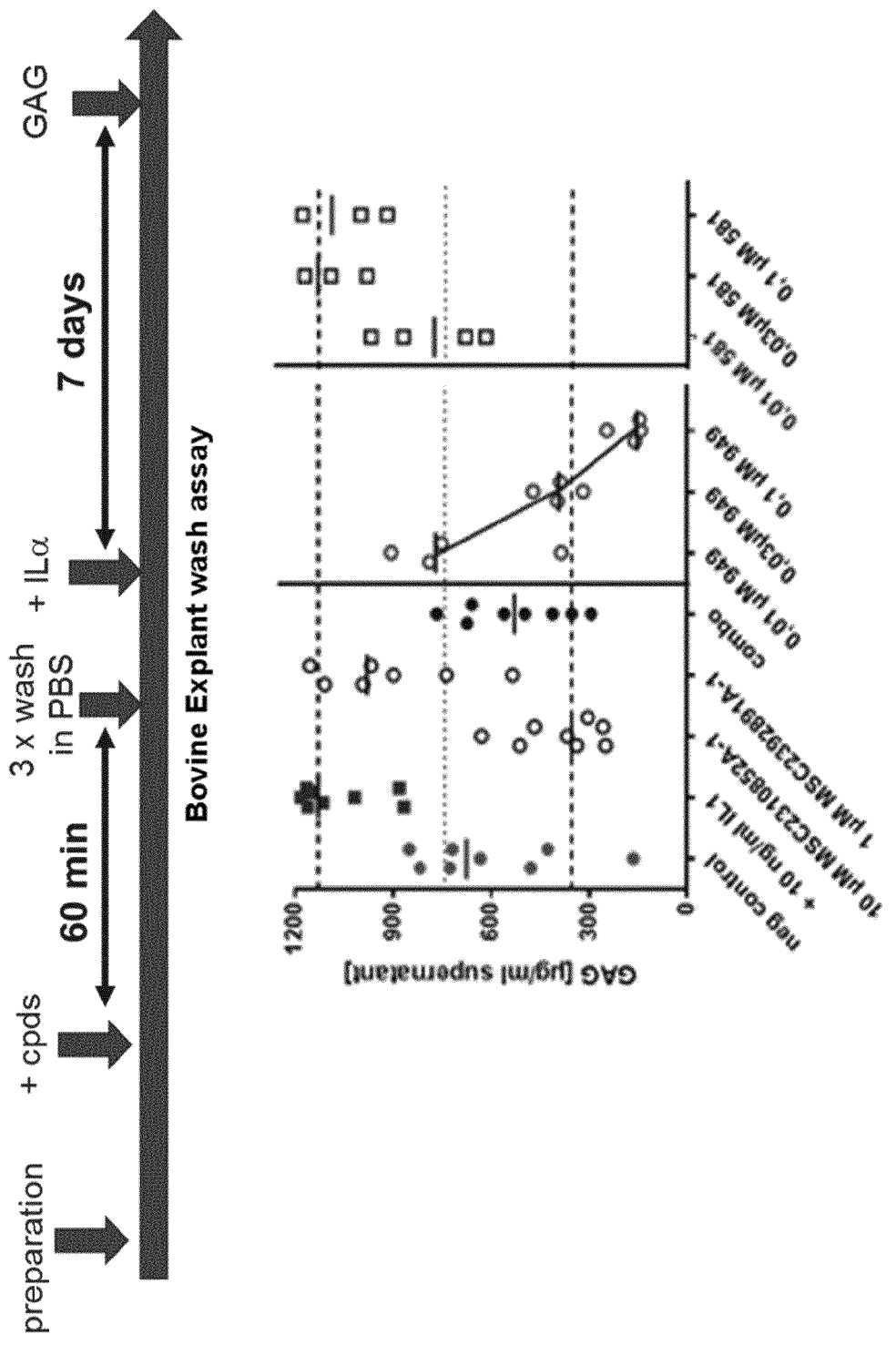

FIG. 5: Effect of CAP-mediated cartilage anchorage of polypeptides in bovine explant assay.

Figure 6:
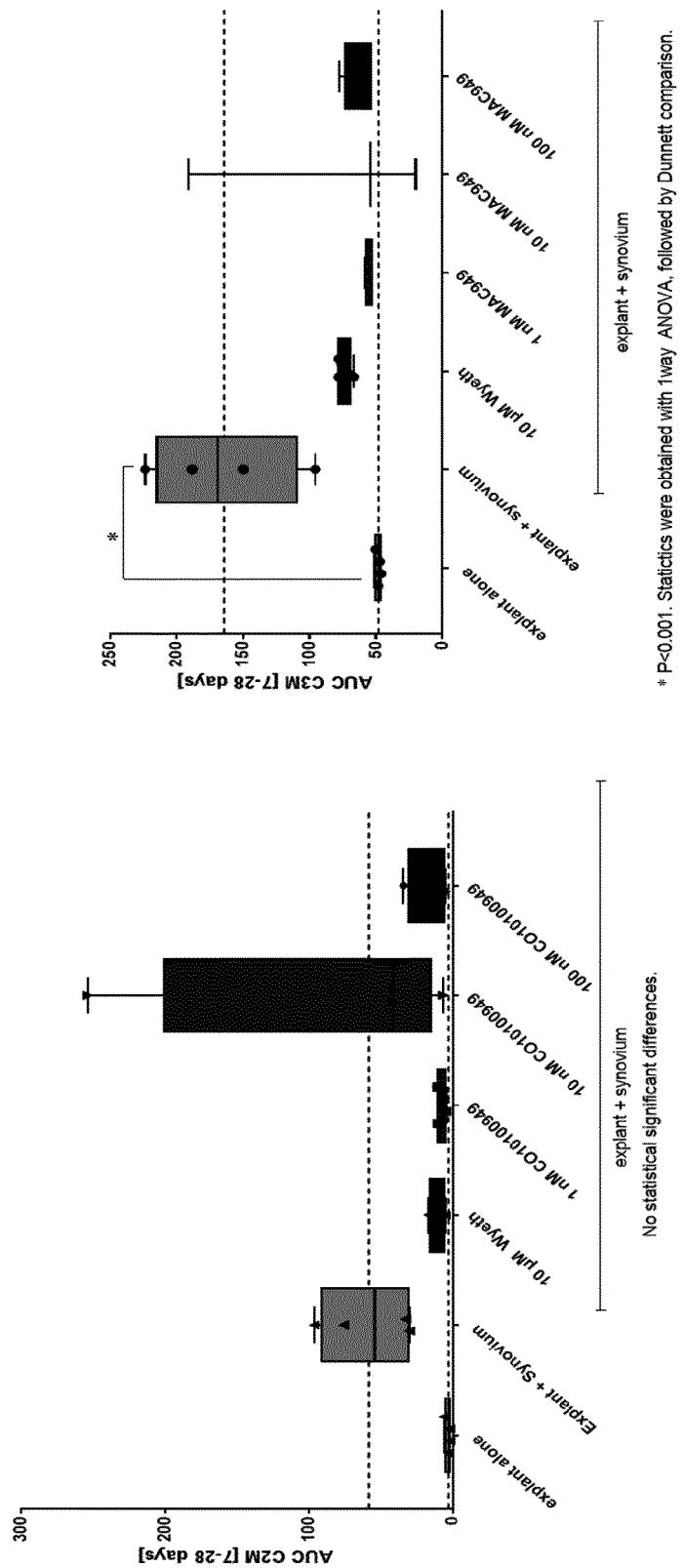

FIG. 6: Polypeptide 949 ("C010100949" or "MAC949") inhibits the release of C2M (Col II degradation=structure) and C3M (Col III degradation=associated with symptoms) out of the co-culture.

Figure 7:
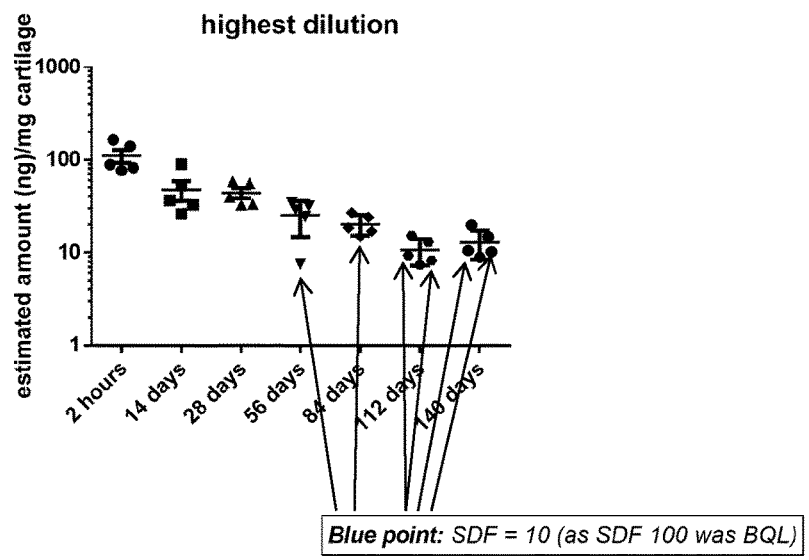

FIG. 7: Cartilage retention: local Nanobody construct concentrations at different time points in rats.

Figure 8:
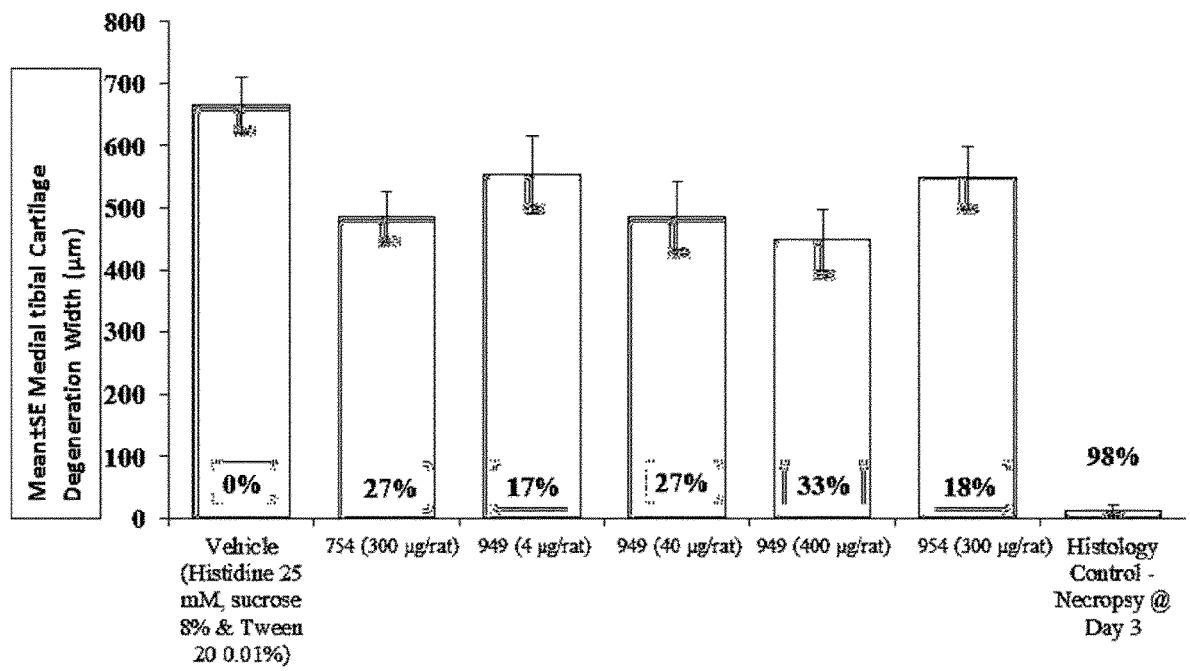

FIG. 8: Medial tibial substantial cartilage degeneration width in different groups.

Figure 9:
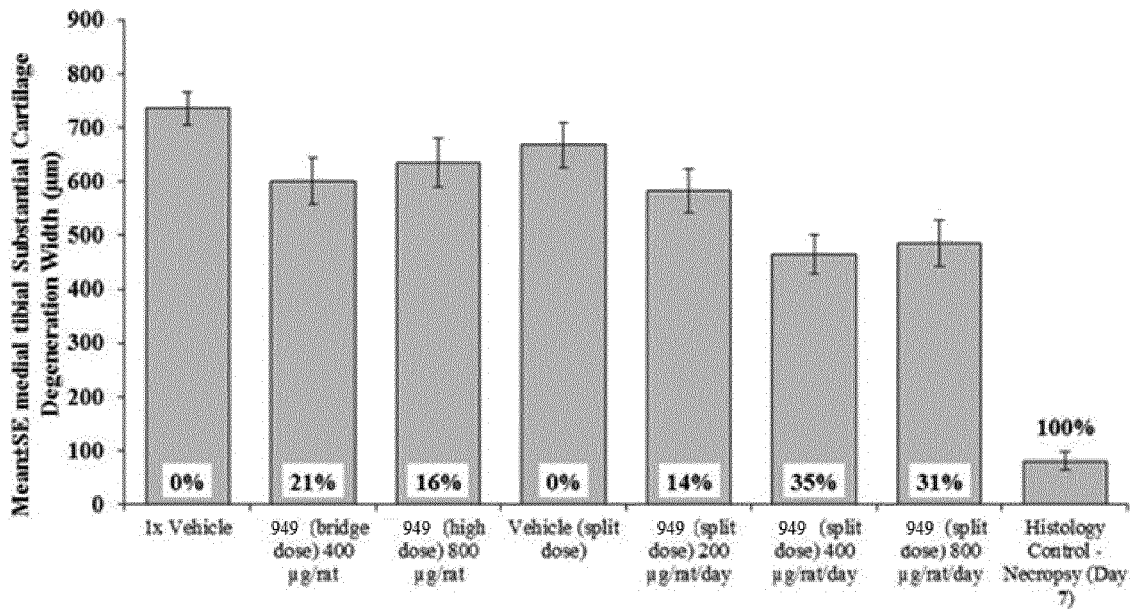

FIG. 9: Medial tibial cartilage degeneration width.

Figure 10:
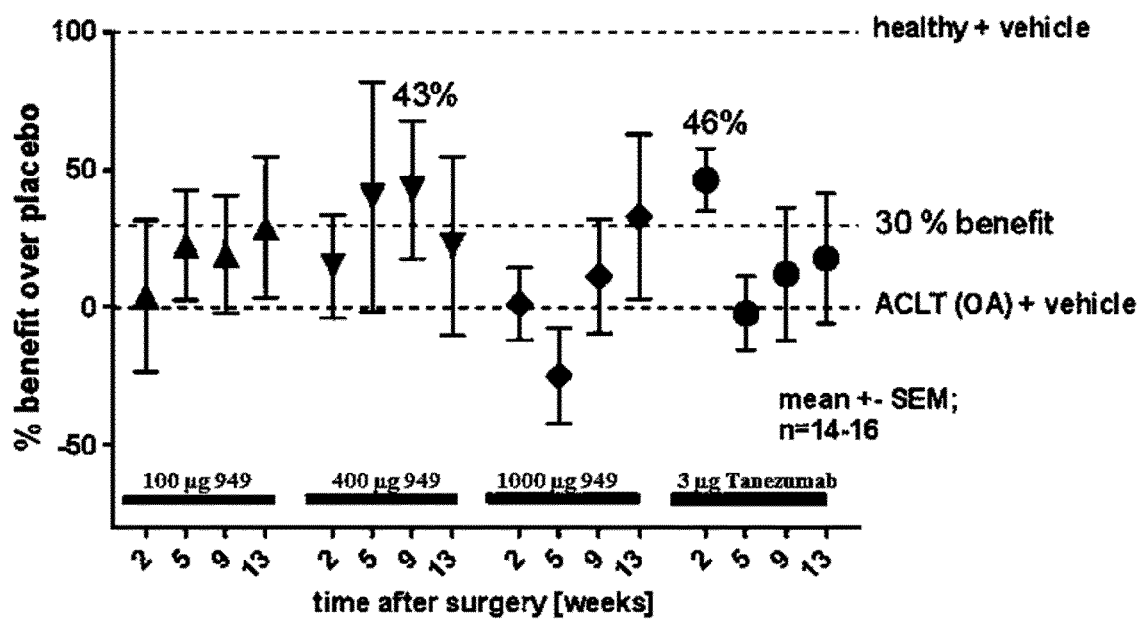

FIG. 10: Gait analysis by catwalk.

Figure 11:
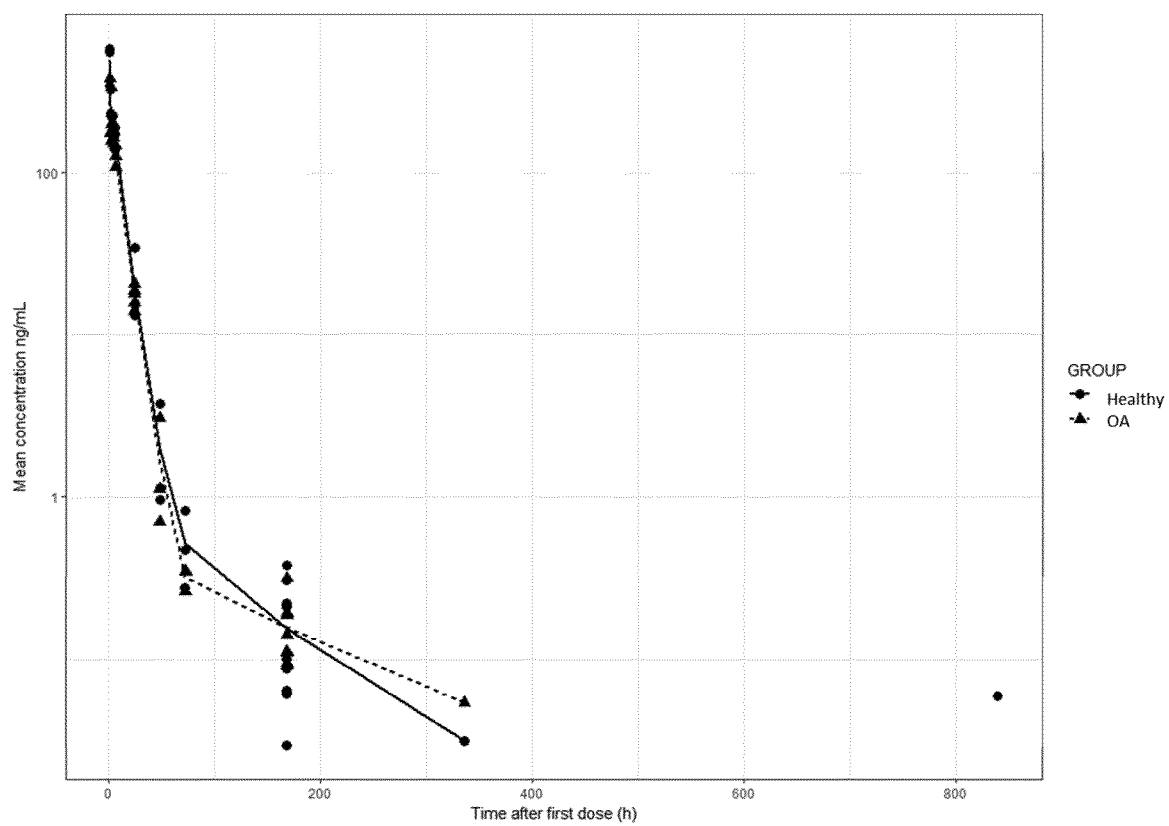

FIG. 11: Serum concentrations (mean concentration in ng/ml) versus time after first dose (h) of polypeptides in osteoarthritis rats and healthy rats, receiving a single intra-articular injection of 400 μg Nanobody construct per joint (right knee). Dots represent individual concentrations in healthy animals; triangles represent individual concentrations in OA animals; and lines represent mean concentrations.

5 DETAILED DESCRIPTION

There remains a need for safe and efficacious OA medicaments, in particular DMOADs. These medicaments should comply with various and frequently opposing requirements, especially when a broadly applicable format is intended. Such a format should preferably be useful in a broad range of patients. The format should preferably be safe and not induce infections due to frequent administration. In addition, the format should preferably be patient friendly, such as allowing for a convenient dosing regimen and route of administration, e.g. systemic administration. For instance, it is preferred that the format is not removed instantaneously from circulation upon administration. However, extending the half-life should preferably not introduce off-target activity and side effects or limit efficacy.

The present invention realizes at least one of these requirements.

Based on unconventional screening, characterization and combinatory strategies, the present inventors surprisingly observed that immunoglobulin single variable domains (ISVDs) performed exceptionally well in in vitro, ex vivo and in vivo experiments.

Moreover, the present inventors were able to re-engineer the ISVDs further outperforming comparator drugs in ameliorating OA. In addition, the ISVDs of the invention were also demonstrated to be significantly safer than the prior art compounds.

In addition, the inventors demonstrated that combining various functionalities, including MMP13 inhibitors, ADAMTS5 inhibitors and Aggrecan binders, an even better effect was obtained than with either of the inhibitors.

The present invention intends providing combinations of ISVDs antagonizing ADAMTSs, in particular ADAMTS5, and/or ISVDs antagonizing MMPs, in particular MMP13, coupled to CAP binders (e.g. Aggrecan binders), with improved prophylactic, therapeutic and/or pharmacological properties, including a safer profile, compared to the prior art amino acid sequences and antibodies.

Accordingly, the present invention relates to polypeptides chosen from the group consisting of
  (a) polypeptides comprising at least 2 immunoglobulin single variable domains (ISVD), in which a first ISVD specifically binds a matrix metalloproteinase (MMP) and a second ISVD specifically binds Aggrecan, and optionally comprising a third ISVD specifically binding Aggrecan;
  (b) polypeptides comprising at least 2 ISVDs, in which a first ISVD specifically binds an A Disintegrin and Metalloproteinase with Thrombospondin motifs (ADAMTS) and a second ISVD specifically binds Aggrecan, and optionally comprising a third ISVD specifically binding Aggrecan; and
  (c) polypeptides comprising at least 3 ISVDs, in which a first ISVD specifically binds an MMP, a second ISVD specifically binds an ADAMTS and a third ISVD specifically binds Aggrecan, and optionally comprising a fourth ISVD specifically binding Aggrecan.

Unless indicated or defined otherwise, all terms used have their usual meaning in the art, which will be clear to the skilled person. Reference is for example made to the standard handbooks, such as Sambrook et al. (Molecular Cloning: A Laboratory Manual ($2^{nd}$ Ed.) Vols. 1-3, Cold Spring Harbor Laboratory Press, 1989), F. Ausubel et al. (Current protocols in molecular biology, Green Publishing and Wiley Interscience, New York, 1987), Lewin (Genes II, John Wiley & Sons, New York, N.Y., 1985), Old et al. (Principles of Gene Manipulation: An Introduction to Genetic Engineering ($2^{nd}$ edition) University of California Press, Berkeley, Calif., 1981); Roitt et al. (Immunology ($6^{th}$ Ed.) Mosby/Elsevier, Edinburgh, 2001), Roitt et al. (Roitt's Essential Immunology ($10^{th}$ Ed.) Blackwell Publishing, UK, 2001), and Janeway et al. (Immunobiology ($6^{th}$ Ed.) Garland Science Publishing/Churchill Livingstone, N.Y., 2005), as well as to the general background art cited herein.

Unless indicated otherwise, all methods, steps, techniques and manipulations that are not specifically described in detail can be performed and have been performed in a manner known per se, as will be clear to the skilled person. Reference is for example again made to the standard handbooks and the general background art mentioned herein and to the further references cited therein; as well as to for example the following reviews Presta (Adv. Drug Deliv. Rev. 58 (5-6): 640-56, 2006), Levin and Weiss (Mol. Biosyst. 2(1): 49-57, 2006), Irving et al. (J. Immunol. Methods 248(1-2): 31-45, 2001), Schmitz et al. (Placenta 21 Suppl. A: S106-12, 2000), Gonzales et al. (Tumour Biol. 26(1): 31-43, 2005), which describe techniques for protein engineering, such as affinity maturation and other techniques for improving the specificity and other desired properties of proteins such as immunoglobulins.

It must be noted that as used herein, the singular forms "a", "an", and "the", include plural references unless the context clearly indicates otherwise. Thus, for example, reference to "a reagent" includes one or more of such different reagents and reference to "the method" includes reference to equivalent steps and methods known to those of ordinary skill in the art that could be modified or substituted for the methods described herein.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

The term "and/or" wherever used herein includes the meaning of "and", "or" and "all or any other combination of the elements connected by said term".

The term "about" or "approximately" as used herein means within 20%, preferably within 15%, more preferably within 10%, and most preferably within 5% of a given value or range.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having".

The term "sequence" as used herein (for example in terms like "immunoglobulin sequence", "antibody sequence", "variable domain sequence", "$V_{HH}$ sequence" or "protein sequence"), should generally be understood to include both the relevant amino acid sequence as well as nucleic acids or nucleotide sequences encoding the same, unless the context requires a more limited interpretation.

Amino acid sequences are interpreted to mean a single amino acid or an unbranched sequence of two or more amino acids, depending of the context. Nucleotide sequences are interpreted to mean an unbranched sequence of 3 or more nucleotides.

Amino acids are those L-amino acids commonly found in naturally occurring proteins. Amino acid residues will be indicated according to the standard three-letter or one-letter amino acid code. Reference is for instance made to Table A-2 on page 48 of WO 08/020079. Those amino acid sequences containing D-amino acids are not intended to be embraced by this definition. Any amino acid sequence that contains post-translationally modified amino acids may be described as the amino acid sequence that is initially translated using the symbols shown in this Table A-2 with the modified positions; e.g., hydroxylations or glycosylations, but these modifications shall not be shown explicitly in the amino acid sequence. Any peptide or protein that can be expressed as a sequence modified linkages, cross links and end caps, non-peptidyl bonds, etc., is embraced by this definition, all as known in the art.

The terms "protein", "peptide", "protein/peptide", and "polypeptide" are used interchangeably throughout the disclosure and each has the same meaning for purposes of this disclosure. Each term refers to an organic compound made of a linear chain of two or more amino acids. The compound may have ten or more amino acids; twenty-five or more amino acids; fifty or more amino acids; one hundred or more amino acids, two hundred or more amino acids, and even three hundred or more amino acids. The skilled artisan will appreciate that polypeptides generally comprise fewer amino acids than proteins, although there is no art-recognized cut-off point of the number of amino acids that distinguish a polypeptide and a protein; that polypeptides may be made by chemical synthesis or recombinant methods; and that proteins are generally made in vitro or in vivo by recombinant methods as known in the art. By convention, the amide bond in the primary structure of polypeptides is in the order that the amino acids are written, in which the amine end (N-terminus) of a polypeptide is always on the left, while the acid end (C-terminus) is on the right.

A nucleic acid or amino acid sequence is considered to be "(in) (essentially) isolated (form)"—for example, compared to the reaction medium or cultivation medium from which it has been obtained—when it has been separated from at least one other component with which it is usually associated in said source or medium, such as another nucleic acid, another protein/polypeptide, another biological component or macromolecule or at least one contaminant, impurity or minor component. In particular, a nucleic acid or amino acid sequence is considered "(essentially) isolated" when it has been purified at least 2-fold, in particular at least 10-fold, more in particular at least 100-fold, and up to 1000-fold or more. A nucleic acid or amino acid that is "in (essentially) isolated form" is preferably essentially homogeneous, as determined using a suitable technique, such as a suitable chromatographical technique, such as polyacrylamide-gel electrophoresis.

When a nucleotide sequence or amino acid sequence is said to "comprise" another nucleotide sequence or amino acid sequence, respectively, or to "essentially consist of" another nucleotide sequence or amino acid sequence, this may mean that the latter nucleotide sequence or amino acid sequence has been incorporated into the first mentioned nucleotide sequence or amino acid sequence, respectively, but more usually this generally means that the first mentioned nucleotide sequence or amino acid sequence comprises within its sequence a stretch of nucleotides or amino acid residues, respectively, that has the same nucleotide sequence or amino acid sequence, respectively, as the latter sequence, irrespective of how the first mentioned sequence has actually been generated or obtained (which may for example be by any suitable method described herein). By means of a non-limiting example, when a polypeptide of the invention is said to comprise an immunoglobulin single variable domain ("ISVD"), this may mean that said immunoglobulin single variable domain sequence has been incorporated into the sequence of the polypeptide of the invention, but more usually this generally means that the polypeptide of the invention contains within its sequence the sequence of the immunoglobulin single variable domains irrespective of how said polypeptide of the invention has been generated or obtained. Also, when a nucleic acid or nucleotide sequence is said to comprise another nucleotide sequence, the first mentioned nucleic acid or nucleotide sequence is preferably such that, when it is expressed into an expression product (e.g. a polypeptide), the amino acid sequence encoded by the latter nucleotide sequence forms part of said expression product (in other words, that the latter nucleotide sequence is in the same reading frame as the first mentioned, larger nucleic acid or nucleotide sequence). Also, when a construct of the invention is said to comprise a polypeptide or ISVD, this may mean that said construct at least encompasses said polypeptide or ISVD, respectively, but more usually this means that said construct encompasses groups, residues (e.g. amino acid residues), moieties and/or binding units in addition to said polypeptide or ISVD, irrespective of how said polypeptide or ISVD is connected to said groups, residues (e.g. amino acid residues), moieties and/or binding units and irrespective of how said construct has been generated or obtained.

By "essentially consist of" is meant that the ISVD used in the invention either is exactly the same as the ISVD of the invention or corresponds to an ISVD of the invention, having a limited number of amino acid residues, such as 1-20 amino acid residues, for example 1-10 amino acid residues and preferably 1-6 amino acid residues, such as 1, 2, 3, 4, 5 or 6 amino acid residues, added at the amino terminal end, at the carboxy terminal end, or at both the amino terminal end and the carboxy terminal end of the ISVD.

For the purposes of comparing two or more nucleotide sequences, the percentage of "sequence identity" between a first nucleotide sequence and a second nucleotide sequence may be calculated by dividing [the number of nucleotides in the first nucleotide sequence that are identical to the nucleotides at the corresponding positions in the second nucleotide sequence] by [the total number of nucleotides in the first nucleotide sequence] and multiplying by [100%], in which each deletion, insertion, substitution or addition of a nucleotide in the second nucleotide sequence-compared to the first nucleotide sequence—is considered as a difference at a single nucleotide (position). Alternatively, the degree of sequence identity between two or more nucleotide sequences may be calculated using a known computer algorithm for sequence alignment such as NCBI Blast v2.0, using standard settings. Some other techniques, computer algorithms and settings for determining the degree of sequence identity are for example described in WO 04/037999, EP 0967284, EP 1085089, WO 00/55318, WO 00/78972, WO 98/49185 and GB 2357768. Usually, for the purpose of determining the percentage of "sequence identity" between two nucleotide sequences in accordance with the calculation method outlined hereinabove, the nucleotide sequence with the greatest number of nucleotides will be taken as the "first" nucleotide sequence, and the other nucleotide sequence will be taken as the "second" nucleotide sequence.

For the purposes of comparing two or more amino acid sequences, the percentage of "sequence identity" between a first amino acid sequence and a second amino acid sequence (also referred to herein as "amino acid identity") may be calculated by dividing [the number of amino acid residues in the first amino acid sequence that are identical to the amino acid residues at the corresponding positions in the second amino acid sequence] by [the total number of amino acid residues in the first amino acid sequence] and multiplying by [100%], in which each deletion, insertion, substitution or addition of an amino acid residue in the second amino acid sequence-compared to the first amino acid sequence—is considered as a difference at a single amino acid residue (position), i.e., as an "amino acid difference" as defined herein. Alternatively, the degree of sequence identity between two amino acid sequences may be calculated using a known computer algorithm, such as those mentioned above for determining the degree of sequence identity for nucleotide sequences, again using standard settings. Usually, for the purpose of determining the percentage of "sequence identity" between two amino acid sequences in accordance with the calculation method outlined hereinabove, the amino acid sequence with the greatest number of amino acid residues will be taken as the "first" amino acid sequence, and the other amino acid sequence will be taken as the "second" amino acid sequence.

Also, in determining the degree of sequence identity between two amino acid sequences, the skilled person may take into account so-called "conservative" amino acid substitutions, which can generally be described as amino acid substitutions in which an amino acid residue is replaced with another amino acid residue of similar chemical structure and which has little or essentially no influence on the function, activity or other biological properties of the polypeptide. Such conservative amino acid substitutions are well known in the art, for example from WO 04/037999, GB 335768, WO 98/49185, WO 00/46383 and WO 01/09300; and (preferred) types and/or combinations of such substitutions may be selected on the basis of the pertinent teachings from WO 04/037999 as well as WO 98/49185 and from the further references cited therein.

Such conservative substitutions preferably are substitutions in which one amino acid within the following groups (a)-(e) is substituted by another amino acid residue within the same group: (a) small aliphatic, nonpolar or slightly polar residues: Ala, Ser, Thr, Pro and Gly; (b) polar, negatively charged residues and their (uncharged) amides: Asp, Asn, Glu and Gln; (c) polar, positively charged residues: His, Arg and Lys; (d) large aliphatic, nonpolar residues: Met, Leu, Ile, Val and Cys; and (e) aromatic residues: Phe, Tyr and Trp. Particularly preferred conservative substitutions are as follows: Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

Any amino acid substitutions applied to the polypeptides described herein may also be based on the analysis of the frequencies of amino acid variations between homologous proteins of different species developed by Schulz et al. ("Principles of Protein Structure", Springer-Verlag, 1978), on the analyses of structure forming potentials developed by Chou and Fasman (Biochemistry 13: 211, 1974; Adv. Enzymol., 47: 45-149, 1978), and on the analysis of hydrophobicity patterns in proteins developed by Eisenberg et al. (Proc. Natl. Acad Sci. USA 81: 140-144, 1984), Kyte and Doolittle (J. Molec. Biol. 157: 105-132, 1981), and Goldman et al. (Ann. Rev. Biophys. Chem. 15: 321-353, 1986), all incorporated herein in their entirety by reference. Information on the primary, secondary and tertiary structure of Nanobodies is given in the description herein and in the general background art cited above. Also, for this purpose, the crystal structure of a $V_{HH}$ domain from a llama is for example given by Desmyter et al. (Nature Structural Biology, 3: 803, 1996), Spinelli et al. (Natural Structural Biology, 3: 752-757, 1996) and Decanniere et al. (Structure, 7 (4): 361, 1999). Further information about some of the amino acid residues that in conventional $V_H$ domains form the $V_H/V_L$ interface and potential camelizing substitutions on these positions can be found in the prior art cited above.

Amino acid sequences and nucleic acid sequences are said to be "exactly the same" if they have 100% sequence identity (as defined herein) over their entire length.

When comparing two amino acid sequences, the term "amino acid(s) difference" refers to an insertion, deletion or substitution of a single amino acid residue on a position of the first sequence, compared to the second sequence; it being understood that two amino acid sequences can contain one, two or more such amino acid differences. More particularly, in the ISVDs and/or polypeptides of the present invention, the term "amino acid(s) difference" refers to an insertion, deletion or substitution of a single amino acid residue on a position of the CDR sequence specified in (b), (d) or (f), compared to the CDR sequence of respectively (a), (c) or (e); it being understood that the CDR sequence of (b), (d) and (f) can contain one, two, three, four or maximal five such amino acid differences compared to the CDR sequence of respectively (a), (c) or (e).

The "amino acid(s) difference" can be any one, two, three, four or maximal five substitutions, deletions or insertions, or any combination thereof, that either improve the properties of the ISVD of the invention, i.e. ADAMTS5 binder, MMP13 binder and/or Aggrecan binder of the invention, such as the polypeptide of the invention or that at least do not detract too much from the desired properties or from the balance or combination of desired properties of the ISVDs of the invention, i.e. ADAMTS5 binder, MMP13 binder and/or Aggrecan binder of the invention, such as the polypeptide(s) of the invention comprising an Aggrecan binder and a MMP13 binder and/or an ADAMTS5 binder. In this respect, the resulting polypeptide(s) of the invention should at least bind Aggrecan and MMP13 and/or ADAMTS5 with the same, about the same, or a higher affinity compared to the polypeptide comprising the one or more CDR sequences without the one, two, three, four or maximal five substitutions, deletions or insertions. The affinity can be measured by any suitable method known in the art, but is preferably measured by a method as described in the examples section.

In this respect, the amino acid sequence of the CDRs according to (b), (d) and/or (f) as indicated herein, may be an amino acid sequence that is derived from an amino acid sequence according to (a), (c) and/or (e) respectively by means of affinity maturation using one or more techniques of affinity maturation known per se or as described in the Examples. For example, and depending on the host organism used to express the polypeptide of the invention, such deletions and/or substitutions may be designed in such a way that one or more sites for post-translational modification (such as one or more glycosylation sites) are removed, as will be within the ability of the person skilled in the art (cf. Examples).

A "Nanobody family", "$V_{HH}$ family" or "family" as used in the present specification refers to a group of Nanobodies and/or $V_{HH}$ sequences that have identical lengths (i.e. they have the same number of amino acids within their sequence) and of which the amino acid sequence between position 8 and position 106 (according to Kabat numbering) has an amino acid sequence identity of 89% or more.

The terms "epitope" and "antigenic determinant", which can be used interchangeably, refer to the part of a macromolecule, such as a polypeptide or protein that is recognized by antigen-binding molecules, such as immunoglobulins, conventional antibodies, immunoglobulin single variable domains and/or polypeptides of the invention, and more particularly by the antigen-binding site of said molecules. Epitopes define the minimum binding site for an immunoglobulin, and thus represent the target of specificity of an immunoglobulin.

The part of an antigen-binding molecule (such as an immunoglobulin, a conventional antibody, an immunoglobulin single variable domain and/or a polypeptide of the invention) that recognizes the epitope is called a "paratope".

An amino acid sequence (such as an immunoglobulin single variable domain, an antibody, a polypeptide of the invention, or generally an antigen binding protein or polypeptide or a fragment thereof) that can "bind to" or "specifically bind to", that "has affinity for" and/or that "has specificity for" a certain epitope, antigen or protein (or for at least one part, fragment or epitope thereof) is said to be "against" or "directed against" said epitope, antigen or protein or is a "binding" molecule with respect to such epitope, antigen or protein, or is said to be "anti"-epitope, "anti"-antigen or "anti"-protein (e.g., "anti"-Aggrecan, "anti"-MMP13 and/or"anti"-ADAMTS5).

The affinity denotes the strength or stability of a molecular interaction. The affinity is commonly given as the $K_D$, or dissociation constant, which has units of mol/liter (or M). The affinity can also be expressed as an association constant, $K_A$, which equals $1/K_D$ and has units of (mol/liter)$^{-1}$ (or M$^{-1}$). In the present specification, the stability of the interaction between two molecules will mainly be expressed in terms of the $K_D$ value of their interaction; it being clear to the skilled person that in view of the relation $K_A=1/K_D$, specifying the strength of molecular interaction by its $K_D$ value can also be used to calculate the corresponding $K_A$ value. The $K_D$-value characterizes the strength of a molecular interaction also in a thermodynamic sense as it is related to the change of free energy (DG) of binding by the well-known relation DG=RT·ln($K_D$) (equivalently DG=−RT·ln($K_A$)), where R equals the gas constant, T equals the absolute temperature and ln denotes the natural logarithm. The $K_D$ for biological interactions which are considered meaningful (e.g. specific) are typically in the range of 10$^{-12}$M (0.001 nM) to 10$^{-5}$M (10000 nM). The stronger an interaction is, the lower is its $K_D$.

The $K_D$ can also be expressed as the ratio of the dissociation rate constant of a complex, denoted as $k_{off}$, to the rate of its association, denoted $k_{on}$ (so that $K_D=k_{off}/k_{on}$ and $K_A=k_{on}/k_{off}$). The off-rate $k_{off}$ has units s$^{-1}$ (where s is the SI unit notation of second). The on-rate $k_{on}$ has units M$^{-1}$s$^{-1}$. The on-rate may vary between 10$^2$ M$^{-1}$ s$^{-1}$ to about 10$^7$ M$^{-1}$ s$^{-1}$, approaching the diffusion-limited association rate constant for bimolecular interactions. The off-rate is related to the half-life of a given molecular interaction by the relation $t_{1/2}=\ln(2)/k_{off}$. The off-rate may vary between 10$^{-6}$ s$^{-1}$ (near irreversible complex with a $t_{1/2}$ of multiple days) to 1 s$^{-1}$ ($t_{1/2}$=0.69 s).

Specific binding of an antigen-binding protein, such as an ISVD, to an antigen or antigenic determinant can be determined in any suitable manner known per se, including, for example, saturation binding assays and/or competitive binding assays, such as radio-immunoassays (RIA), enzyme immunoassays (EIA) and sandwich competition assays, and the different variants thereof known per se in the art; as well as the other techniques mentioned herein.

The affinity of a molecular interaction between two molecules can be measured via different techniques known per se, such as the well-known surface plasmon resonance (SPR) biosensor technique (see for example Ober et al. 2001, Intern. Immunology 13: 1551-1559) where one molecule is immobilized on the biosensor chip and the other molecule is passed over the immobilized molecule under flow conditions yielding $k_{on}$, $k_{off}$ measurements and hence $K_D$ (or $K_A$) values. This can for example be performed using the well-known BIACORE® instruments (Pharmacia Biosensor AB, Uppsala, Sweden). Kinetic Exclusion Assay (KINEXA®) (Drake et al. 2004, Analytical Biochemistry 328: 35-43) measures binding events in solution without labeling of the binding partners and is based upon kinetically excluding the dissociation of a complex. In-solution affinity analysis can also be performed using the GYROLAB® immunoassay system, which provides a platform for automated bioanalysis and rapid sample turnaround (Fraley et al. 2013, Bioanalysis 5: 1765-74), or ELISA.

It will also be clear to the skilled person that the measured $K_D$ may correspond to the apparent $K_D$ if the measuring process somehow influences the intrinsic binding affinity of the implied molecules for example by artifacts related to the coating on the biosensor of one molecule. Also, an apparent $K_D$ may be measured if one molecule contains more than one recognition site for the other molecule. In such situation the measured affinity may be affected by the avidity of the interaction by the two molecules. In particular, the accurate measurement of $K_D$ may be quite labor-intensive and as a consequence, often apparent $K_D$ values are determined to assess the binding strength of two molecules. It should be noted that as long as all measurements are made in a consistent way (e.g. keeping the assay conditions unchanged) apparent $K_D$ measurements can be used as an approximation of the true $K_D$ and hence in the present document $K_D$ and apparent $K_D$ should be treated with equal importance or relevance.

The term "specificity" refers to the number of different types of antigens or antigenic determinants to which a particular antigen-binding molecule or antigen-binding protein (such as an ISVD or polypeptide of the invention) molecule can bind. The specificity of an antigen-binding protein can be determined based on affinity and/or avidity, for instance as described on pages 53-56 of WO 08/020079 (incorporated herein by reference), which also describes some preferred techniques for measuring binding between an antigen-binding molecule (such as a polypeptide or ISVD of the invention) and the pertinent antigen. Typically, antigen-binding proteins (such as the ISVDs and/or polypeptides of the invention) will bind to their antigen with a dissociation constant ($K_D$) of 10$^{-5}$ to 10$^{-12}$ moles/liter or less, and preferably 10$^{-7}$ to 10$^{-12}$ moles/liter or less and more preferably 10$^{-8}$ to 10$^{-12}$ moles/liter (i.e., with an association constant ($K_A$) of 10$^5$ to 10$^{12}$ liter/moles or more, and preferably 10$^7$ to 10$^{12}$ liter/moles or more and more preferably 10$^8$ to 10$^{12}$ liter/moles). Any $K_D$ value greater than 10$^{-4}$ mol/liter (or any $K_A$ value lower than 10$^4$ liter/mol) is generally considered to indicate non-specific binding. Preferably, a monovalent ISVD of the invention will bind to the desired antigen with an affinity less than 500 nM, preferably less than 200 nM, more preferably less than 10 nM, such as less than 500 pM, such as e.g., between 10 and 5 pM or less. Reference is also made to paragraph n) on pages 53-56 of WO 08/020079.

An ISVD and/or polypeptide is said to be "specific for" a (first) target or antigen compared to another (second) target or antigen when it binds to the first antigen with an affinity (as described above, and suitably expressed as a $K_D$ value, $K_A$ value, $K_{off}$ rate and/or $K_{on}$ rate) that is at least 10 times, such as at least 100 times, and preferably at least 1000 times or more better than the affinity with which the ISVD and/or polypeptide binds to the second target or antigen. For example, the ISVD and/or polypeptide may bind to the first target or antigen with a $K_D$ value that is at least 10 times less, such as at least 100 times less, and preferably at least 1000 times less or even less than that, than the $K_D$ with which said ISVD and/or polypeptide binds to the second target or antigen. Preferably, when an ISVD and/or polypeptide is "specific for" a first target or antigen compared to a second target or antigen, it is directed against (as defined herein) said first target or antigen, but not directed against said second target or antigen.

Specific binding of an antigen-binding protein to an antigen or antigenic determinant can be determined in any suitable manner known per se, including, for example, saturation binding assays and/or competitive binding assays, such as radioimmunoassays (RIA), enzyme immunoassays (EIA) and the different variants thereof known in the art; as well as the other techniques mentioned herein.

A preferred approach that may be used to assess affinity is the 2-step ELISA (Enzyme-Linked Immunosorbent Assay) procedure of Friguet et al. 1985 (J. Immunol. Methods 77: 305-19). This method establishes a solution phase binding equilibrium measurement and avoids possible artifacts relating to adsorption of one of the molecules on a support such as plastic. As will be clear to the skilled person, the dissociation constant may be the actual or apparent dissociation constant. Methods for determining the dissociation constant will be clear to the skilled person, and for example include the techniques mentioned on pages 53-56 of WO 08/020079.

Finally, it should be noted that in many situations the experienced scientist may judge it to be convenient to determine the binding affinity relative to some reference molecule. For example, to assess the binding strength between molecules A and B, one may e.g. use a reference molecule C that is known to bind to B and that is suitably labelled with a fluorophore or chromophore group or other chemical moiety, such as biotin for easy detection in an ELISA or FACS (Fluorescent activated cell sorting) or other format (the fluorophore for fluorescence detection, the chromophore for light absorption detection, the biotin for streptavidin-mediated ELISA detection). Typically, the reference molecule C is kept at a fixed concentration and the concentration of A is varied for a given concentration or amount of B. As a result an $IC_{50}$ value is obtained corresponding to the concentration of A at which the signal measured for C in absence of A is halved. Provided $K_{D\ ref}$, the $K_D$ of the reference molecule, is known, as well as the total concentration $c_{ref}$ of the reference molecule, the apparent $K_D$ for the interaction A-B can be obtained from following formula: $K_D = IC_{50}/(1+C_{ref}/K_{Dref})$. Note that if $c_{ref} \ll K_{D\ ref}$, $K_D \approx IC_{50}$. Provided the measurement of the $IC_{50}$ is performed in a consistent way (e.g. keeping $c_{ref}$ fixed) for the binders that are compared, the difference in strength or stability of a molecular interaction can be assessed by comparing the $IC_{50}$ and this measurement is judged as equivalent to $K_D$ or to apparent $K_D$ throughout this text.

The half maximal inhibitory concentration ($IC_{50}$) can also be a measure of the effectiveness of a compound in inhibiting a biological or biochemical function, e.g. a pharmacological effect. This quantitative measure indicates how much of the polypeptide or ISVD (e.g. a Nanobody) is needed to inhibit a given biological process (or component of a process, i.e. an enzyme, cell, cell receptor, chemotaxis, anaplasia, metastasis, invasiveness, etc.) by half. In other words, it is the half maximal (50%) inhibitory concentration (IC) of a substance (50% IC, or $IC_{50}$). $IC_{50}$ values can be calculated for a given antagonist such as the polypeptide or ISVD (e.g. a Nanobody) of the invention by determining the concentration needed to inhibit half of the maximum biological response of the agonist. The $K_D$ of a drug can be determined by constructing a dose-response curve and examining the effect of different concentrations of antagonist such as the polypeptide or ISVD (e.g. a Nanobody) of the invention on reversing agonist activity.

The term half maximal effective concentration ($EC_{50}$) refers to the concentration of a compound which induces a response halfway between the baseline and maximum after a specified exposure time. In the present context it is used as a measure of a polypeptide, ISVD (e.g. a Nanobody) its potency. The $EC_{50}$ of a graded dose response curve represents the concentration of a compound where 50% of its maximal effect is observed. Concentration is preferably expressed in molar units.

In biological systems, small changes in ligand concentration typically result in rapid changes in response, following a sigmoidal function. The inflection point at which the increase in response with increasing ligand concentration begins to slow is the $EC_{50}$. This can be determined mathematically by derivation of the best-fit line. Relying on a graph for estimation is convenient in most cases. In case the $EC_{50}$ is provided in the examples section, the experiments were designed to reflect the $K_D$ as accurate as possible. In other words, the $EC_{50}$ values may then be considered as $K_D$ values. The term "average $K_D$" relates to the average $K_D$ value obtained in at least 1, but preferably more than 1, such as at least 2 experiments. The term "average" refers to the mathematical term "average" (sums of data divided by the number of items in the data).

It is also related to $IC_{50}$ which is a measure of a compound its inhibition (50% inhibition). For competition binding assays and functional antagonist assays $IC_{50}$ is the most common summary measure of the dose-response curve. For agonist/stimulator assays the most common summary measure is the $EC_{50}$.

The inhibition constant (Ki) is an indication of how potent an inhibitor is; it is the concentration required to produce half maximum inhibition. Unlike $IC_{50}$, which can change depending on the experimental conditions, Ki is an absolute value and is often referred to as the inhibition constant of a drug. The inhibition constant $K_i$ can be calculated by using the Cheng-Prusoff equation:

$$K_i = \frac{IC50}{\frac{[L]}{K_D} + 1}$$

in which [L] is the fixed concentration of the ligand.

The term "potency" of a polypeptide and/or ISVD of the invention, as used herein, is a function of the amount of polypeptide and/or ISVD of the invention required for its specific effect to occur. It refers to the capacity of said polypeptide and/or ISVD of the invention to modulate and/or partially or fully inhibit an activity of MMP13 and/or to modulate and/or partially or fully inhibit an activity of ADAMTS5.

In particular, it may refer to the capacity of said polypeptide to reduce or even totally inhibit MMP13 activity as defined herein. As such, it may refer to the capacity of said polypeptide to inhibit proteolysis, such as protease activity endopeptidase activities, binding a substrate, such as, for instance Aggrecan, Collagen II, Collagen I, Collagen III, Collagen IV, Collagen IX, Collagen X, Collagen XIV and gelatin. The potency may be measured by any suitable assay known in the art or described herein.

In particular, it may refer to the capacity of said polypeptide and/or ISVD to reduce or even totally inhibit an ADAMTS5 activity as defined herein, and/or an MMP13 activity as defined herein. The potency may be measured by any suitable assay known in the art or described herein. As used herein, "aggrecanase activity" is defined as the proteolytic cleavage of Aggrecan.

The "efficacy" of the polypeptide of the invention measures the maximum strength of the effect itself, at saturating polypeptide concentrations. Efficacy indicates the maximum response achievable from the polypeptide of the invention. It refers to the ability of a polypeptide to produce the desired (therapeutic) effect.

In an aspect the invention relates to a polypeptide as described herein, wherein said polypeptide binds to ADAMTS5 with a $K_D$ between $1E^{-07}$ M and $1E^{13}$ M, such as between $1E^{-08}$ M and $1E^{-12}$ M, preferably at most $1E^{-07}$ M, preferably lower than $1E^{-8}$ M or $1E^{-9}$ M, or even lower than $1E^{-10}$ M, such as $5E^{-11}$ M, $4E^{-11}$ M, $3E^{-11}$ M, $2E^{-11}$ M, $1.7E^{-11}$ M, $1E^{-11}$ M, or even $5E^{-12}$ M, $4E^{-12}$ M, $3E^{-12}$ M, $1E^{-12}$ M, for instance as determined by Gyrolab or KinExA.

In an aspect the invention relates to a polypeptide as described herein, wherein said polypeptide binds to MMP13 with a $K_D$ between $1E^{-07}$ M and $1E^{-13}$ M, such as between $1E^{-8}$ M and $1E^{-12}$ M, preferably at most $1E^{-07}$ M, preferably lower than $1E^{-08}$ M or $1E^{-09}$ M, or even lower than $1E^{-10}$ M, such as $5E^{-11}$ M, $4E^{-11}$ M, $3E^{-11}$ M, $2E^{-11}$ M, $1.7E^{-11}$ M, $1E^{-11}$ M, or even $5E^{-12}$ M, $4E^{-12}$ M, $3E^{-12}$ M, $1E^{-12}$ M, for instance as determined by Gyrolab or KinExA.

In an aspect the invention relates to a polypeptide as described herein, wherein said polypeptide binds to Aggrecan a $K_D$ between $1E^{-07}$ M and $1E^{-13}$ M, such as between $1E^{-08}$ M and $1E^{-12}$ M, preferably at most $1E^{-07}$ M, preferably lower than $1E^{-08}$ M or $1E^{-09}$ M, or even lower than $1E^{-10}$ M, such as $5E^{-11}$ M, $4E^{-11}$ M, $3E^{-11}$ M, $2E^{-11}$ M, $1.7E^{-11}$ M, $1E^{-11}$ M, or even $5E^{-12}$ M, $4E^{-12}$ M, $3E^{-12}$ M, $1E^{-12}$ M, for instance as determined by Gyrolab or KinExA.

In an aspect the invention relates to a polypeptide as described herein, wherein said polypeptide binds to ADAMTS5 with an off-rate of less than $5E^{-4}$ $s^{-1}$, such as, e.g. less than $1E^{-4}$ $s^{-1}$ or $5E^{-05}$ $s^{-1}$, or even less than $1E^{-5}$ $s^{-1}$, for instance as determined by SPR.

In an aspect the invention relates to a polypeptide as described herein, wherein said polypeptide binds to MMP13 with an off-rate of less than $5E^{-04}$ $s^{-1}$, such as less than $1E^{-04}$ $s^{-1}$ or $5E^{-05}$ $s^{-1}$, or even less than $1E^{-05}$ $s^{-1}$, for instance as determined by SPR.

In an aspect the invention relates to a polypeptide as described herein, wherein said polypeptide binds to Aggrecan with an off-rate of less than $5E^{-4}$ $s^{-1}$, such as less than $1E^{-04}$ $s^{-1}$ or $5E^{-05}$ $s^{-1}$, or even less than $1E^{05}$ $s^{-1}$, for instance as determined by SPR.

In an aspect the invention relates to a polypeptide as described herein, wherein said polypeptide modulates an ADAMTS5 activity and/or an MMP13 activity with an $EC_{50}$ between $1E^{-07}$ M and $1E^{-12}$ M, such as between $1E^{-08}$ M and $1E^{-11}$ M, for instance as determined by binding ELISA (for determining ADAMTS5 activity) or e.g. competition ELISA, competition TIMP-2 ELISA, fluorogenic peptide assay, fluorogenic collagen assay or collagenolytic assay (for determining MMP13 activity).

In an aspect the invention relates to a polypeptide as described herein, wherein said polypeptide inhibits an activity of ADAMTS5 and/or MMP13 with an $IC_{50}$ between $1E^{-07}$ M and $1E^{-12}$ M, such as between $1E^{-08}$ M and $1E^{-11}$ M, for instance as determined by human FRET assay or human AlphaLISA (for determining ADAMTS5 activity) or e.g. competition ELISA, competition TIMP-2 ELISA, fluorogenic peptide assay, fluorogenic collagen assay or collagenolytic assay (for determining MMP13 activity).

In an aspect the invention relates to a polypeptide as described herein, wherein said polypeptide inhibits an enzymatic activity of ADAMTS5 and/or MMP13 with an $IC_{50}$ of at most $1E^{-07}$ M, preferably $1E^{-08}$ M, $5E^{-09}$ M, or $4E^{-9}$ M, $3E^{-9}$ M, $2E^{-9}$ M, such as $1E^{-9}$ M.

An amino acid sequence, such as an ISVD or polypeptide, is said to be "cross-reactive" for two different antigens or antigenic determinants (such as e.g., ADAMTS5 from different species of mammals, such as e.g., human ADAMTS5, bovine ADAMTS5, rat ADAMTS5, guinea pig ADAMTS5, mouse ADAMTS5 or cynomolgus ADAMTS5 or such as e.g., MMP13 from different species of mammals, such as e.g., human MMP13, dog MMP13, bovine MMP13, rat MMP13, pig MMP13, mouse MMP13, rabbit MMP13, cynomolgus MMP13, and/or rhesus MMP13 or such as e.g., Aggrecan from different species of mammals, such as e.g., human Aggrecan, dog Aggrecan, bovine Aggrecan, rat Aggrecan, pig Aggrecan, mouse Aggrecan, rabbit Aggrecan, cynomolgus Aggrecan, and/or rhesus Aggrecan) if it is specific for (as defined herein) these different antigens or antigenic determinants. It will be appreciated that an ISVD or polypeptide may be considered to be cross-reactive although the binding affinity for the two different antigens can differ, such as by a factor, 2, 5, 10, 50, 100 or even more provided it is specific for (as defined herein) these different antigens or antigenic determinants.

ADAMTS5 is also known as ADAMTS11, ADMP-2 or Aggrecanase-2. Relevant structural information for ADAMTS5 may be found, for example, at UniProt Accession Numbers as depicted in the Table B-1 below (cf. Table B).

TABLE B-1

| Protein Acc. | Gene | Organism |
| --- | --- | --- |
| Q9UNA0 | ADAMTS5 | H. sapiens |
| Q9TT92 | ADAMTS5 | B. taurus |
| Q6TY19 | ADAMTS5 | R. norvegicus |
| H0VFP0 | ADAMTS5 | Cavia Porcellus |
| Q9R001 | ADAMTS5 | M. musculus |
| F6Z3S6 | ADAMTS5 | M. mulatta |

"Human ADAMTS5" refers to the ADAMTS5 comprising the amino acid sequence of SEQ ID NO: 67. In an aspect the polypeptide of the invention specifically binds ADAMTS5 from Human sapiens, Mus musculus, Cavia Porcellus, Bos taurus, Macaca mulatta and/or Rattus norvegicus, preferably human ADAMTS5, preferably SEQ ID NO: 67.

MMP13 is also known as CLG3 or Collagenase 3, MANDP1, MMP-13, Matrix metallopeptidase 13, or MDST. Relevant structural information for MMP13 may be found, for example, at UniProt Accession Numbers as depicted in the Table B-2 below (cf. Table B).

TABLE B-2

| Protein Acc. | Gene | Organism |
| --- | --- | --- |
| NP 002418.1 | MMP13 | H. sapiens |
| XP 001154361.1 | MMP13 | P. troglodytes |
| XP 001098996.1 | MMP13 | M. mulatta |
| XP 536598.3 | MMP13 | C. lupus |
| NP 776814.1 | MMP13 | B. taurus |
| NP 032633.1 | MMP13 | M. musculus |
| NP 598214.1 | MMP13 | R. norvegicus |
| XP 003640635.1 | MMP13 | G. gallus |

"Human MMP13" refers to the MMP13 comprising the amino acid sequence of SEQ ID NO: 66. In an aspect the polypeptide of the invention specifically binds MMP13 from Human sapiens, Mus musculus, Canis lupus, Bos taurus, Macaca mulatta, Rattus norvegicus, Gallus gallus, and/or P. troglodytes, preferably human MMP13, preferably SEQ ID NO: 66.

Aggrecan is also known as aggrecan 1, ACAN, AGC1, AGCAN, CSPGCP, MSK16, SEDK, cartilage-specific proteoglycan core protein (CSPCP) or chondroitin sulfate proteoglycan 1 (CSPG1). Aggrecan is in humans encoded by the ACAN gene, which is located at chromosome Chr 15: q26.1. Relevant structural information for Aggrecan may be found, for example, at UniProt Accession Numbers as depicted in the Table B-3 below (cf. Table B).

TABLE B-3

| Protein Acc. | Gene | Organism |
| --- | --- | --- |
| P16112 | ACAN | H. sapiens |
| XP_003952775.2 | ACAN | P. troglodytes |
| XP_002804990.1 | ACAN | M. mulatta |

TABLE B-3-continued

| Protein Acc. | Gene | Organism |
| --- | --- | --- |
| Q28343 | ACAN | C. lupus |
| P13608 | ACAN | B. taurus |
| Q61282 | ACAN | M. musculus |
| P07897 | ACAN | R. norvegicus |
| Q29011 | ACAN | S. scrofa |
| G1U677-1 | ACAN | O. cuniculus |
| NP_990286.2 | ACAN | G. gallus |

"Human Aggrecan" refers to the Aggrecan comprising the amino acid sequence of SEQ ID NO: 68. In an aspect the polypeptide of the invention specifically binds Aggrecan from *Human sapiens, Mus musculus, Bos taurus, Macaca mulatta, Pan troglodytes, Gallus gallus, Canis lupus, Sus scrofa, Oryctolagus cuniculus* and/or *Rattus norvegicus*, preferably human Aggrecan, preferably SEQ ID NO: 68.

The terms "(cross)-block", "(cross)-blocked", "(cross)-blocking", "competitive binding", "(cross)-compete", "(cross)-competing" and "(cross)-competition" are used interchangeably herein to mean the ability of an immunoglobulin, antibody, ISVD, polypeptide or other binding agent to interfere with the binding of other immunoglobulins, antibodies, ISVDs, polypeptides or binding agents to a given target. The extent to which an immunoglobulin, antibody, ISVD, polypeptide or other binding agent is able to interfere with the binding of another to the target, and therefore whether it may be said to cross-block according to the invention, may be determined using competition binding assays, which are common in the art, such as, for instance, by screening purified ISVDs against ISVDs displayed on phage in a competition ELISA. Particularly suitable quantitative cross-blocking assays include ELISA.

Other methods for determining whether an immunoglobulin, antibody, ISVD, polypeptide or other binding agent directed against a target (cross)-blocks, is capable of (cross)-blocking, competitively binds or is (cross)-competitive as defined herein, can be evaluated by an SPR-based "sandwich assay", such as for instance described in the Examples section. Other suitable methods are described e.g. in Xiao-Chi Jia et al. (Journal of Immunological Methods 288: 91-98, 2004), Miller et al. (Journal of Immunological Methods 365: 118-125, 2011).

"ADAMTS5 activities" and "activities of ADAMTS5" (these terms are used interchangeably herein) include, but are not limited to enzymatic activities, such as proteolysis, e.g. protease activity (also called proteinase or peptidase activity), and endopeptidase activities, on the one hand, and the activities by the exosites, such as for instance recognizing and/or binding the substrate, e.g. by disintegrin-like domain, central thrombospondin type I-like (TS) repeat, cysteine-rich domain, spacer region and/or additional TS motifs. ADAMTS5 activities include binding and/or proteolysis of substrates such as hyaluronan-binding chondroitin sulfate proteoglycan (CSPG) extracellular proteins, such as Aggrecan, Versican, Brevican, Neurocan, Decorin and Biglycan. As used herein, proteolysis is the breakdown of proteins into smaller polypeptides or amino acids by hydrolysis of the peptide bonds that link amino acids together in a polypeptide chain.

"MMP13 activities" and "activities by MMP13" (these terms are used interchangeably herein) include, but are not limited to, proteolysis, such as protease activity (also called proteinase or peptidase activity), and endopeptidase activities, on the one hand, and binding the substrate, for instance by Hemopexin-like domain and peptidoglycan binding domain. MMP13 activities include binding and/or proteolysis of substrates such as Aggrecan, Collagen II, Collagen I, Collagen III, Collagen IV, Collagen IX, Collagen X, Collagen XIV and Gelatin. As used herein, proteolysis is the breakdown of proteins into smaller polypeptides or amino acids by hydrolysis of the peptide bonds that link amino acids together in a polypeptide chain.

In the context of the present invention, "modulating" or "to modulate" generally means altering an activity by ADAMTS5 and/or MMP13, as measured using a suitable in vitro, cellular or in vivo assay (such as those mentioned herein). In particular, "modulating" or "to modulate" may mean either reducing or inhibiting an activity of, or alternatively increasing an activity of ADAMTS5 and/or MMP13, as measured using a suitable in vitro, cellular or in vivo assay (for instance, such as those mentioned herein), by at least 1%, preferably at least 5%, such as at least 10% or at least 25%, for example by at least 50%, at least 60%, at least 70%, at least 80%, or 90% or more, compared to activity of ADAMTS5 and/or MMP13 in the same assay under the same conditions but without the presence of the ISVD or polypeptide of the invention.

Accordingly, the present invention relates to a polypeptide as described herein, wherein said polypeptide modulates an activity of ADAMTS5 and/or MMP13, preferably inhibiting an activity of ADAMTS5 and/or MMP13.

Accordingly, the present invention relates to a polypeptide as described herein, wherein said polypeptide inhibits protease activity of ADAMTS5, such as inhibits the proteolysis of a substrate, such as Aggrecan, Versican, Brevican, Neurocan, Decorin, and/or Biglycan.

Accordingly, the present invention relates to a polypeptide as described herein, wherein said polypeptide blocks the binding of ADAMTS5 to a substrate, such as Aggrecan, Versican, Brevican, Neurocan, Decorin, and/or Biglycan, wherein said substrate is preferably Aggrecan.

In an aspect the invention relates to a polypeptide as described herein, wherein said polypeptide blocks the binding of ADAMTS5 to Aggrecan of at least 20%, such as at least 30%, 40%, 50%, 60%, 70%, 80%, 90%, 95% or even more, for instance as determined by ELISA.

In an aspect the invention relates to a polypeptide as described herein, wherein said polypeptide antagonizes or inhibits an activity of ADAMTS5, such as (i) a protease activity, preferably cleavage of Aggrecan, Versican, Brevican, Neurocan, Decorin, and/or Biglycan, preferably cleavage of Aggrecan; preferably antagonizes aggrecanase activity of ADAMTS5; (ii) binding of a substrate to ADAMTS5, such as an exosite of ADAMTS5, for instance the disintegrin-like domain, the central thrombospondin type I-like (TS) repeat, the cysteine-rich domain, the spacer region or the additional TS motif.

Accordingly, the present invention relates to a polypeptide as described herein, wherein said polypeptide inhibits protease activity of MMP13, such as inhibits the proteolysis of a substrate, such as Aggrecan, Collagen II, Collagen I, Collagen III, Collagen IV, Collagen IX, Collagen X, Collagen XIV and/or Gelatin.

Accordingly, the present invention relates to a polypeptide as described herein, wherein said polypeptide blocks the binding of MMP13 to a substrate, such as Aggrecan, Collagen II, Collagen I, Collagen III, Collagen IV, Collagen IX, Collagen X, Collagen XIV and/or Gelatin, wherein said Collagen is preferably Collagen II.

In an aspect the invention relates to a polypeptide as described herein, wherein said polypeptide blocks the binding of MMP13 to Collagen and/or Aggrecan of at least 20%, such as at least 30%, 40%, 50%, 60%, 70%, 80%, 90%, 95% or even more, for instance as determined by ELISA-based competition assays (cf. Howes et al. 2014 J. Biol. Chem. 289:24091-24101).

In an aspect the invention relates to a polypeptide as described herein, wherein said polypeptide antagonizes or inhibits an activity of MMP13, such as (i) a protease activity, preferably cleavage of Aggrecan and/or Collagen, wherein said Collagen is preferably Collagen II; (ii) binding of Collagen to the hemopexin-like domain.

In an aspect, the present invention relates to a polypeptide as described herein, wherein said polypeptide inhibits protease activity of ADAMTS5 and/or MMP13, preferably by at least 5%, such as 10%, 20%, 30%, 40%, 50% or even more, such as at least 60%, 70%, 80%, 90%, 95% or even more, as determined by any suitable method known in the art, such as for instance by competition assays or as described in the Examples section.

Although the ADAMs, ADAMTSs and MMPs share a binding site to Aggrecan that is very similar both in sequence and in overall shape, e.g., the catalytic domains of ADAMTS4 and ADAMTS5 share a high degree of sequence similarity, the inventors were able to identify ISVDs which were target specific, as demonstrated in the examples. The target specificity also would avoid or at least limit musculoskeletal syndrome, which is a side-effect caused by broad-spectrum inhibitors.

In an aspect the invention relates to an ADAMTS5 binder such as an ISVD and polypeptide of the invention, wherein said ADAMTS5 binder does not bind ADAMTS4, ADAMTS1, ADAMTS15, MMP1 and/or MMP14 (membrane type). Preferably, the present invention relates to a polypeptide as defined herein, wherein said ISVD binding ADAMTS5 does not bind ADAMTS4, MMP1 or MMP14.

In an aspect the invention relates to an MMP13 binder such as an ISVD and polypeptide of the invention, wherein said MMP13 binder does not bind MMP1 and/or MMP14 (membrane type). Preferably, the present invention relates to a polypeptide as defined herein, wherein said ISVD binding MMP13 does not bind MMP1 or MMP14.

Unless indicated otherwise, the terms "immunoglobulin" and "immunoglobulin sequence"—whether used herein to refer to a heavy chain antibody or to a conventional 4-chain antibody—is used as a general term to include both the full-size antibody, the individual chains thereof, as well as all parts, domains or fragments thereof (including but not limited to antigen-binding domains or fragments such as $V_{HH}$ domains or $V_H/V_L$ domains, respectively).

The term "domain" (of a polypeptide or protein) as used herein refers to a folded protein structure which has the ability to retain its tertiary structure independently of the rest of the protein. Generally, domains are responsible for discrete functional properties of proteins, and in many cases may be added, removed or transferred to other proteins without loss of function of the remainder of the protein and/or of the domain.

The term "immunoglobulin domain" as used herein refers to a globular region of an antibody chain (such as e.g., a chain of a conventional 4-chain antibody or of a heavy chain antibody), or to a polypeptide that essentially consists of such a globular region. Immunoglobulin domains are characterized in that they retain the immunoglobulin fold characteristic of antibody molecules, which consists of a two-layer sandwich of about seven antiparallel beta-strands arranged in two beta-sheets, optionally stabilized by a conserved disulphide bond.

The term "immunoglobulin variable domain" as used herein means an immunoglobulin domain essentially consisting of four "framework regions" which are referred to in the art and herein below as "framework region 1" or "FR1"; as "framework region 2" or "FR2"; as "framework region 3" or "FR3"; and as "framework region 4" or "FR4", respectively; which framework regions are interrupted by three "complementarity determining regions" or "CDRs", which are referred to in the art and herein below as "complementarity determining region 1" or "CDR1"; as "complementarity determining region 2" or "CDR2"; and as "complementarity determining region 3" or "CDR3", respectively. Thus, the general structure or sequence of an immunoglobulin variable domain may be indicated as follows: FR1-CDR1-FR2-CDR2-FR3-CDR3-FR4. It is the immunoglobulin variable donnain(s) that confer specificity to an antibody for the antigen by carrying the antigen-binding site.

The term "immunoglobulin single variable domain" (abbreviated herein as "ISVD" or "ISV"), and interchangeably used with "single variable domain", defines molecules wherein the antigen binding site is present on, and formed by, a single immunoglobulin domain. This sets immunoglobulin single variable domains apart from "conventional" immunoglobulins or their fragments, wherein two immunoglobulin domains, in particular two variable domains, interact to form an antigen binding site. Typically, in conventional immunoglobulins, a heavy chain variable domain ($V_H$) and a light chain variable domain ($V_L$) interact to form an antigen binding site. In the latter case, the complementarity determining regions (CDRs) of both $V_H$ and $V_L$ will contribute to the antigen binding site, i.e. a total of 6 CDRs will be involved in antigen binding site formation.

In view of the above definition, the antigen-binding domain of a conventional 4-chain antibody (such as an IgG, IgM, IgA, IgD or IgE molecule; known in the art) or of a Fab fragment, a $F(ab')_2$ fragment, an Fv fragment such as a disulphide linked Fv or a scFv fragment, or a diabody (all known in the art) derived from such conventional 4-chain antibody, would normally not be regarded as an immunoglobulin single variable domain, as, in these cases, binding to the respective epitope of an antigen would normally not occur by one (single) immunoglobulin domain but by a pair of (associating) immunoglobulin domains such as light and heavy chain variable domains, i.e., by a $V_H$-$V_L$ pair of immunoglobulin domains, which jointly bind to an epitope of the respective antigen.

In contrast, ISVDs are capable of specifically binding to an epitope of the antigen without pairing with an additional immunoglobulin variable domain. The binding site of an ISVD is formed by a single $V_{HH}$, $V_H$ or $V_L$ domain. Hence, the antigen binding site of an ISVD is formed by no more than three CDRs.

As such, the single variable domain may be a light chain variable domain sequence (e.g., a $V_L$-sequence) or a suitable fragment thereof; or a heavy chain variable domain sequence (e.g., a $V_H$-sequence or $V_{HH}$ sequence) or a suitable fragment thereof; as long as it is capable of forming a single antigen binding unit (i.e., a functional antigen binding unit that essentially consists of the single variable domain, such that the single antigen binding domain does not need to interact with another variable domain to form a functional antigen binding unit).

In one embodiment of the invention, the ISVDs are heavy chain variable domain sequences (e.g., a $V_H$-sequence); more specifically, the ISVDs may be heavy chain variable domain sequences that are derived from a conventional four-chain antibody or heavy chain variable domain sequences that are derived from a heavy chain antibody.

For example, the ISVD may be a (single) domain antibody (or an amino acid that is suitable for use as a (single) domain antibody), a "dAb" or sdAb (or an amino acid that is suitable for use as a dAb) or a Nanobody (as defined herein, and including but not limited to a VHH); other single variable domains, or any suitable fragment of any one thereof.

In particular, the ISVD may be a Nanobody® (as defined herein) or a suitable fragment thereof. [Note: Nanobody®, Nanobodies® and Nanoclone® are registered trademarks of Ablynx N.V.] For a general description of Nanobodies, reference is made to the further description below, as well as to the prior art cited herein, such as e.g. described in WO 08/020079 (page 16).

"$V_{HH}$ domains", also known as $V_HHs$, $V_HH$ domains, VHH antibody fragments, and VHH antibodies, have originally been described as the antigen binding immunoglobulin (variable) domain of "heavy chain antibodies" (i.e., of "antibodies devoid of light chains"; Hamers-Casterman et al. 1993 Nature 363: 446-448). The term "$V_{HH}$ domain" has been chosen in order to distinguish these variable domains from the heavy chain variable domains that are present in conventional 4-chain antibodies (which are referred to herein as "$V_H$ domains" or "VH domains") and from the light chain variable domains that are present in conventional 4-chain antibodies (which are referred to herein as "$V_L$ domains" or "VL domains"). For a further description of VHHs and Nanobodies, reference is made to the review article by Muyldermans (Reviews in Molecular Biotechnology 74: 277-302, 2001), as well as to the following patent applications, which are mentioned as general background art: WO 94/04678, WO 95/04079 and WO 96/34103 of the Vrije Universiteit Brussel; WO 94/25591, WO 99/37681, WO 00/40968, WO 00/43507, WO 00/65057, WO 01/40310, WO 01/44301, EP 1134231 and WO 02/48193 of Unilever; WO 97/49805, WO 01/21817, WO 03/035694, WO 03/054016 and WO 03/055527 of the Vlaams Instituut voor Biotechnologie (VIB); WO 03/050531 of Algonomics N.V. and Ablynx N.V.; WO 01/90190 by the National Research Council of Canada; WO 03/025020 (=EP 1433793) by the Institute of Antibodies; as well as WO 04/041867, WO 04/041862, WO 04/041865, WO 04/041863, WO 04/062551, WO 05/044858, WO 06/40153, WO 06/079372, WO 06/122786, WO 06/122787 and WO 06/122825, by Ablynx N.V. and the further published patent applications by Ablynx N.V. Reference is also made to the further prior art mentioned in these applications, and in particular to the list of references mentioned on pages 41-43 of the International application WO 06/040153, which list and references are incorporated herein by reference. As described in these references, Nanobodies (in particular VHH sequences and partially humanized Nanobodies) can in particular be characterized by the presence of one or more "Hallmark residues" in one or more of the framework sequences. A further description of the Nanobodies, including humanization and/or camelization of Nanobodies, as well as other modifications, parts or fragments, derivatives or "Nanobody fusions", multivalent constructs (including some non-limiting examples of linker sequences) and different modifications to increase the half-life of the Nanobodies and their preparations may be found e.g. in WO 08/101985 and WO 08/142164. For a further general description of Nanobodies, reference is made to the prior art cited herein, such as e.g. described in WO 08/020079 (page 16).

In particular, the framework sequences present in the Aggrecan, ADAMTS5 and/or MMP13 binders of the invention, such as the ISVDs and/or polypeptides of the invention, may contain one or more of Hallmark residues (for instance as described in WO 08/020079 (Tables A-3 to A-8)), such that the Aggrecan, ADAMTS5 and/or MMP13 binder of the invention is a Nanobody. Some preferred, but non-limiting examples of (suitable combinations of) such framework sequences will become clear from the further disclosure herein (see e.g., Table A-2). Generally, Nanobodies (in particular $V_{HH}$ sequences and partially humanized Nanobodies) can in particular be characterized by the presence of one or more "Hallmark residues" in one or more of the framework sequences (as e.g., further described in WO 08/020079, page 61, line 24 to page 98, line 3). As used herein "represented by" in the context of any SEQ ID NO is equivalent to "comprises or consists of" said SEQ ID NO and preferably equivalent to "consists of" said SEQ ID NO.

More in particular, the invention provides Aggrecan, ADAMTS5 and/or MMP13 binders comprising at least one immunoglobulin single variable domain that is an amino acid sequence with the (general) structure:
  FR1-CDR1-FR2-CDR2-FR3-CDR3-FR4
in which FR1 to FR4 refer to framework regions 1 to 4, respectively, and in which CDR1 to CDR3 refer to the complementarity determining regions 1 to 3, respectively, and which:

i) have at least 80%, more preferably 90%, even more preferably 95% amino acid identity with at least one of the amino acid sequences of SEQ ID NOs: 2, 3 or 4 (see Table A-1), in which for the purposes of determining the degree of amino acid identity, the amino acid residues that form the CDR sequences are disregarded. In this respect, reference is also made to Table A-2, which lists the framework 1 sequences (SEQ ID NO: 7), framework 2 sequences (SEQ ID NOs: 9, 15 and 20), framework 3 sequences (SEQ ID NOs: 11, 17 and 22) and framework 4 sequences (SEQ ID NO: 13) of the immunoglobulin single variable domains of SEQ ID NOs: 2, 3 and 4; or
  ii) combinations of framework sequences as depicted in Table A-2;
and in which:
  iii) preferably one or more of the amino acid residues at positions 11, 37, 44, 45, 47, 83, 84, 103, 104 and 108 according to the Kabat numbering are chosen from the Hallmark residues, for instance, such as mentioned in Table A-3 to Table A-8 of WO 08/020079.

The Aggrecan, ADAMTS5 and/or MMP13 binders of the invention, such as the ISVDs and/or polypeptides of the invention, may also contain the specific mutations/amino acid residues described in the following co-pending US provisional applications, all entitled "Improved immunoglobulin variable domains": US 61/994552 filed May 16, 2014; US 61/014,015 filed Jun. 18, 2014; US 62/040,167 filed Aug. 21, 2014; and U.S. 62/047,560, filed Sep. 8, 2014 (all assigned to Ablynx N.V.).

In particular, the Aggrecan, ADAMTS5 and/or MMP13 binders of the invention, such as the ISVDs and/or polypeptides of the invention, may suitably contain (i) a K or Q at position 112; or (ii) a K or Q at position 110 in combination with a V at position 11; or (iii) a T at position 89; or (iv) an L on position 89 with a K or Q at position 110; or (v) a V at position 11 and an L at position 89; or any suitable combination of (i) to (v).

As also described in said co-pending US provisional applications, when the Aggrecan, ADAMTS5 and/or MMP13 binders of the invention, such as the ISVDs and/or polypeptides of the invention, contain the mutations according to one of (i) to (v) above (or a suitable combination thereof):

the amino acid residue at position 11 is preferably chosen from L, V or K (and is most preferably V); and/or
the amino acid residue at position 14 is preferably suitably chosen from A or P; and/or
the amino acid residue at position 41 is preferably suitably chosen from A or P; and/or
the amino acid residue at position 89 is preferably suitably chosen from T, V or L; and/or
the amino acid residue at position 108 is preferably suitably chosen from Q or L; and/or
the amino acid residue at position 110 is preferably suitably chosen from T, K or Q; and/or
the amino acid residue at position 112 is preferably suitably chosen from S, K or Q.

As mentioned in said co-pending US provisional applications, said mutations are effective in preventing or reducing binding of so-called "pre-existing antibodies" to the immunoglobulins and compounds of the invention. For this purpose, the Aggrecan, ADAMTS5 and/or MMP13 binders of the invention, such as the ISVDs and/or polypeptides of the invention, may also contain (optionally in combination with said mutations) a C-terminal extension (X)n (in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I)), see e.g. US provisional applications as well as WO 12/175741. In particular, an Aggrecan, ADAMTS5 and/or MMP13 binder of the invention, such as an ISVD and/or polypeptide of the invention, may contain such a C-terminal extension when it forms the C-terminal end of a protein, polypeptide or other compound or construct comprising the same (see e.g. said US provisional applications as well as WO 12/175741).

An Aggrecan, ADAMTS5 and/or MMP13 binder of the invention may be an immunoglobulin, such as an immunoglobulin single variable domain, derived in any suitable manner and from any suitable source, and may for example be naturally occurring $V_{HH}$ sequences (i.e., from a suitable species of Camelid) or synthetic or semi-synthetic amino acid sequences, including but not limited to "humanized" (as defined herein) Nanobodies or VHH sequences, "camelized" (as defined herein) immunoglobulin sequences (and in particular camelized heavy chain variable domain sequences), as well as Nanobodies that have been obtained by techniques such as affinity maturation (for example, starting from synthetic, random or naturally occurring immunoglobulin sequences), CDR grafting, veneering, combining fragments derived from different immunoglobulin sequences, PCR assembly using overlapping primers, and similar techniques for engineering immunoglobulin sequences well known to the skilled person; or any suitable combination of any of the foregoing as further described herein. Also, when an immunoglobulin comprises a $V_{HH}$ sequence, said immunoglobulin may be suitably humanized, as further described herein, so as to provide one or more further (partially or fully) humanized immunoglobulins of the invention. Similarly, when an immunoglobulin comprises a synthetic or semi-synthetic sequence (such as a partially humanized sequence), said immunoglobulin may optionally be further suitably humanized, again as described herein, again so as to provide one or more further (partially or fully) humanized immunoglobulins of the invention.

"Domain antibodies", also known as "Dab"s, "Domain Antibodies", and "dAbs" (the terms "Domain Antibodies" and "dAbs" being used as trademarks by the GlaxoSmithKline group of companies) have been described in e.g., EP 0368684, Ward et al. (Nature 341: 544-546, 1989), Holt et al. (Tends in Biotechnology 21: 484-490, 2003) and WO 03/002609 as well as for example WO 04/068820, WO 06/030220, WO 06/003388 and other published patent applications of Domantis Ltd. Domain antibodies essentially correspond to the VH or VL domains of non-camelid mammalians, in particular human 4-chain antibodies. In order to bind an epitope as a single antigen binding domain, i.e., without being paired with a $V_L$ or $V_H$ domain, respectively, specific selection for such antigen binding properties is required, e.g. by using libraries of human single $V_H$ or $V_L$ domain sequences. Domain antibodies have, like $V_{HH}$s, a molecular weight of approximately 13 to approximately 16 kDa and, if derived from fully human sequences, do not require humanization for e.g. therapeutical use in humans.

It should also be noted that, although less preferred in the context of the present invention because they are not of mammalian origin, single variable domains can be derived from certain species of shark (for example, the so-called "IgNAR domains", see for example WO 05/18629).

The present invention relates particularly to ISVDs, wherein said ISVDs are chosen from the group consisting of VHHs, humanized VHHs and camelized VHs.

The amino acid residues of a VHH domain are numbered according to the general numbering for $V_H$ domains given by Kabat et al. ("Sequence of proteins of immunological interest", US Public Health Services, NIH Bethesda, Md., Publication No. 91), as applied to VHH domains from Camelids, as shown e.g., in FIG. 2 of Riechmann and Muyldermans (J. Immunol. Methods 231: 25-38, 1999), all as known in the art. Alternative methods for numbering the amino acid residues of $V_H$ domains, which methods can also be applied in an analogous manner to VHH domains, are known in the art. However, in the present description, claims and figures, the numbering according to Kabat applied to VHH domains as described above will be followed, unless indicated otherwise.

It should be noted that—as is well known in the art for $V_H$ domains and for VHH domains—the total number of amino acid residues in each of the CDRs may vary and may not correspond to the total number of amino acid residues indicated by the Kabat numbering (that is, one or more positions according to the Kabat numbering may not be occupied in the actual sequence, or the actual sequence may contain more amino acid residues than the number allowed for by the Kabat numbering). This means that, generally, the numbering according to Kabat may or may not correspond to the actual numbering of the amino acid residues in the actual sequence. The total number of amino acid residues in a VH domain and a VHH domain will usually be in the range of from 110 to 120, often between 112 and 115. It should however be noted that smaller and longer sequences may also be suitable for the purposes described herein.

With regard to the CDRs, as is well-known in the art, there are multiple conventions to define and describe the CDRs of a VH or VHH fragment, such as the Kabat definition (which is based on sequence variability and is the most commonly used) and the Chothia definition (which is based on the location of the structural loop regions). Reference is for example made to the website http://www.bioinf.org.uk/abs/. For the purposes of the present specification and claims the CDRs are most preferably defined on the basis of the Abm definition (which is based on Oxford Molecular's AbM antibody modelling software), as this is considered to be an optimal compromise between the Kabat and Chothia definitions (cf. http://www.bioinf.org.uk/abs/). As used herein, FR1 comprises the amino acid residues at positions 1-25, CDR1 comprises the amino acid residues at positions 26-35, FR2 comprises the amino acids at positions 36-49, CDR2 comprises the amino acid residues at positions 50-58, FR3 comprises the amino acid residues at positions 59-94, CDR3 comprises the amino acid residues at positions 95-102, and FR4 comprises the amino acid residues at positions 103-113.

In the meaning of the present invention, the term "immunoglobulin single variable domain" or "single variable domain" comprises polypeptides which are derived from a non-human source, preferably a camelid, preferably a camelid heavy chain antibody. They may be humanized, as described herein. Moreover, the term comprises polypeptides derived from non-camelid sources, e.g. mouse or human, which have been "camelized", as described herein.

Hence, ISVDs such as Domain antibodies and Nanobodies (including VHH domains) may be subjected to humanization. In particular, humanized ISVDs, such as Nanobodies (including VHH domains) may be ISVDs that are as generally defined herein, but in which at least one amino acid residue is present (and in particular, in at least one of the framework residues) that is and/or that corresponds to a humanizing substitution (as defined herein). Potentially useful humanizing substitutions may be ascertained by comparing the sequence of the framework regions of a naturally occurring $V_{HH}$ sequence with the corresponding framework sequence of one or more closely related human $V_H$ sequences, after which one or more of the potentially useful humanizing substitutions (or combinations thereof) thus determined may be introduced into said $V_{HH}$ sequence (in any manner known per se, as further described herein) and the resulting humanized $V_{HH}$ sequences may be tested for affinity for the target, for stability, for ease and level of expression, and/or for other desired properties. In this way, by means of a limited degree of trial and error, other suitable humanizing substitutions (or suitable combinations thereof) may be determined by the skilled person based on the disclosure herein. Also, based on the foregoing, (the framework regions of) an ISVD, such as a Nanobody (including VHH domains) may be partially humanized or fully humanized.

Another particularly preferred class of ISVDs of the invention comprises ISVDs with an amino acid sequence that corresponds to the amino acid sequence of a naturally occurring $V_H$ domain, but that has been "camelized", i.e. by replacing one or more amino acid residues in the amino acid sequence of a naturally occurring $V_H$ domain from a conventional 4-chain antibody by one or more of the amino acid residues that occur at the corresponding position(s) in a $V_{HH}$ domain of a heavy chain antibody. This can be performed in a manner known per se, which will be clear to the skilled person, for example on the basis of the description herein. Such "camelizing" substitutions are preferably inserted at amino acid positions that form and/or are present at the $V_H$-$V_L$ interface, and/or at the so-called Camelidae hallmark residues, as defined herein (see also for example WO 94/04678 and Davies and Riechmann (1994 and 1996)). Preferably, the $V_H$ sequence that is used as a starting material or starting point for generating or designing the camelized immunoglobulin single variable domains is preferably a $V_H$ sequence from a mammal, more preferably the $V_H$ sequence of a human being, such as a $V_H3$ sequence. However, it should be noted that such camelized immunoglobulin single variable domains of the invention can be obtained in any suitable manner known per se and thus are not strictly limited to polypeptides that have been obtained using a polypeptide that comprises a naturally occurring $V_H$ domain as a starting material. Reference is made to Davies and Riechmann (FEBS 339: 285-290, 1994; Biotechnol. 13: 475-479, 1995; Prot. Eng. 9: 531-537, 1996) and Riechmann and Muyldermans (J. Immunol. Methods 231: 25-38, 1999)

For example, again as further described herein, both "humanization" and "camelization" can be performed by providing a nucleotide sequence that encodes a naturally occurring $V_{HH}$ domain or $V_H$ domain, respectively, and then changing, in a manner known per se, one or more codons in said nucleotide sequence in such a way that the new nucleotide sequence encodes a "humanized" or "camelized" ISVD of the invention, respectively. This nucleic acid can then be expressed in a manner known per se, so as to provide the desired ISVDs of the invention. Alternatively, based on the amino acid sequence of a naturally occurring $V_{HH}$ domain or $V_H$ domain, respectively, the amino acid sequence of the desired humanized or camelized ISVDs of the invention, respectively, can be designed and then synthesized de novo using techniques for peptide synthesis known per se. Also, based on the amino acid sequence or nucleotide sequence of a naturally occurring $V_{HH}$ domain or $V_H$ domain, respectively, a nucleotide sequence encoding the desired humanized or camelized ISVDs of the invention, respectively, can be designed and then synthesized de novo using techniques for nucleic acid synthesis known per se, after which the nucleic acid thus obtained can be expressed in a manner known per se, so as to provide the desired ISVDs of the invention.

ISVDs such as Domain antibodies and Nanobodies (including VHH domains and humanized VHH domains), can also be subjected to affinity maturation by introducing one or more alterations in the amino acid sequence of one or more CDRs, which alterations result in an improved affinity of the resulting ISVD for its respective antigen, as compared to the respective parent molecule. Affinity-matured ISVD molecules of the invention may be prepared by methods known in the art, for example, as described by Marks et al. (Biotechnology 10:779-783, 1992), Barbas, et al. (Proc. Nat. Acad. Sci, USA 91: 3809-3813, 1994), Shier et al. (Gene 169: 147-155, 1995), Yelton et al. (Immunol. 155: 1994-2004, 1995), Jackson et al. (J. Immunol. 154: 3310-9, 1995), Hawkins et al. (J. Mol. Biol. 226: 889 896, 1992), Johnson and Hawkins (Affinity maturation of antibodies using phage display, Oxford University Press, 1996).

The process of designing/selecting and/or preparing a polypeptide, starting from an ISVD such as a $V_H$, $V_L$, $V_{HH}$, Domain antibody or a Nanobody, is also referred to herein as "formatting" said ISVD; and an ISVD that is made part of a polypeptide is said to be "formatted" or to be "in the format of" said polypeptide. Examples of ways in which an ISVD may be formatted and examples of such formats will be clear to the skilled person based on the disclosure herein; and such formatted immunoglobulin single variable domain form a further aspect of the invention.

Preferred CDRs are depicted in Table A-2.

In particular, the present invention relates to a polypeptide as described herein, wherein said ISVD specifically binding MMP13 essentially consists of 4 framework regions (FR1 to FR4, respectively) and 3 complementarity determining regions (CDR1 to CDR3 respectively), in which (i) CDR1 is SEQ ID NO: 8; and amino acid sequences that have 1, 2 or 3 amino acid difference(s) with SEQ ID NO: 8;

(ii) CDR2 is SEQ ID NO: 10; and amino acid sequences that have 1, 2 or 3 amino acid difference(s) with SEQ ID NO: 10; and (iii) CDR3 is SEQ ID NO: 12; and amino acid sequences that have 1, 2 or 3 amino acid difference(s) with SEQ ID NO: 12.

In particular, the present invention relates to a polypeptide as described herein, wherein said ISVD specifically binding MMP13 essentially consists of 4 framework regions (FR1 to FR4, respectively) and 3 complementarity determining regions (CDR1 to CDR3 respectively), in which CDR1 is SEQ ID NO: 8, CDR2 is SEQ ID NO: 10 and CDR3 is SEQ ID NO: 12.

In particular, the present invention relates to an ISVD as described herein, wherein said ISVD specifically binding ADAMTS5 essentially consists of 4 framework regions (FR1 to FR4, respectively) and 3 complementarity determining regions (CDR1 to CDR3 respectively), in which (i) CDR1 is SEQ ID NO: 14 [GRTVSSYAMG]; and amino acid sequences that have 1, 2 or 3 amino acid difference(s) with SEQ ID NO: 14;

(ii) CDR2 is SEQ ID NO: 16 [GISRSAERTY]; and amino acid sequences that have 1, 2 or 3 amino acid difference(s) with SEQ ID NO: 16; and (iii) CDR3 is SEQ ID NO: 18 [DLDPNRIFSREEYAY]; and amino acid sequences that have 1, 2 or 3 amino acid difference(s) with SEQ ID NO: 18.

In particular, the present invention relates to an ISVD as described herein, wherein said ISVD specifically binding ADAMTS5 essentially consists of 4 framework regions (FR1 to FR4, respectively) and 3 complementarity determining regions (CDR1 to CDR3 respectively), in which CDR1 is SEQ ID NO: 14, CDR2 is SEQ ID NO: 16 and CDR3 is SEQ ID NO: 18.

In particular, the present invention relates to an ISVD as described herein, wherein said ISVD specifically binding Aggrecan essentially consists of 4 framework regions (FR1 to FR4, respectively) and 3 complementarity determining regions (CDR1 to CDR3 respectively), in which (i) CDR1 is SEQ ID NO: 19; and amino acid sequences that have 1, 2 or 3 amino acid difference(s) with SEQ ID NO: 19;

(ii) CDR2 is SEQ ID NO: 21; and amino acid sequences that have 1, 2 or 3 amino acid difference(s) with SEQ ID NO: 21; and (iii) CDR3 is SEQ ID NO: 23; and amino acid sequences that have 1, 2 or 3 amino acid difference(s) with SEQ ID NO: 23.

In particular, the present invention relates to an ISVD as described herein, wherein said ISVD specifically binding Aggrecan essentially consists of 4 framework regions (FR1 to FR4, respectively) and 3 complementarity determining regions (CDR1 to CDR3 respectively), in which CDR1 is SEQ ID NO: 19, CDR2 is SEQ ID NO: 21 and CDR3 is SEQ ID NO: 23.

In particular, the present invention relates to a polypeptide as described herein, wherein said ISVD specifically binding MMP13 is SEQ ID NO: 2.

In particular, the present invention relates to a polypeptide as described herein, wherein said ISVD specifically binding ADAMTS5 is SEQ ID NO: 3.

In particular, the present invention relates to a polypeptide as described herein, wherein said ISVD specifically binding Aggrecan is SEQ ID NO: 4.

In a further preferred embodiment the Aggrecan, ADAMTS5 and/or MMP13 binder of the invention comprises at least two CDR1 sequences, at least two CDR2 sequences and at least two CDR3 sequences, each selected independently from the following table:

| CDR1 | CDR2 | CDR3 |
|---|---|---|
| SEQ ID NO: 8 (CDR1a) | SEQ ID NO: 10 (CDR2a) | SEQ ID NO: 12 (CDR3a) |
| SEQ ID NO: 14 (CDR1b) | SEQ ID NO: 16 (CDR2b) | SEQ ID NO: 18 (CDR3b) |
| SEQ ID NO: 19 (CDR1c) | SEQ ID NO: 21 (CDR2c) | SEQ ID NO: 23 (CDR3c) |

In the aforementioned Aggrecan, ADAMTS5 and/or MMP13 binder the order of the sequences is preferably CDR1a-CDR2a-CDR3a-Linker-CDR1b-CDR2b-CDR3b, wherein Linker is a polypeptide longer than 5 amino acids that is suitable for linking the first set of CDRs (CDR1a-CDR2a-CDR3a) to the second set (CDR1b-CDR2b-CDR3b). Preferably, the Linker is selected from Table C below and most preferably is a linker with an amino acid sequence according to SEQ ID NO: 35. In a more preferred embodiment the Aggrecan, ADAMTS5 and/or MMP13 binder comprises all nine CDR sequences from the table above, wherein the CDR sequences and the linker polypeptides are in the following order: CDR1a-CDR2a-CDR3a-Linker1-CDR1b-CDR2b-CDR3b-Linker2-CDR1c-CDR2c-CDR3c, wherein Linker1 and Linker2 are each polypeptides of at least 5 amino acids and wherein the polypeptide sequences of Linker1 and Linker2 are identical to each other or non-identical to each other. Preferably, Linker1 and Linker2 are each selected independently from each other from Table C below and most preferably at least one (preferably both) of the linkers has/have the amino acid sequence according to SEQ ID NO: 35.

In a further preferred embodiment the Aggrecan, ADAMTS5 and/or MMP13 binder of the invention preferably comprises at least the CDR sequences listed in the following table:

| | | |
|---|---|---|
| SEQ ID NO: 8 (CDR1a) | SEQ ID NO: 10 (CDR2a) | SEQ ID NO: 12 (CDR3a) |
| SEQ ID NO: 14 (CDR1b) | SEQ ID NO: 16 (CDR2b) | SEQ ID NO: 18 (CDR3b) |
| SEQ ID NO: 19 (CDR1c) | SEQ ID NO: 21 (CDR2c) | SEQ ID NO: 23 (CDR3c) |
| SEQ ID NO: 19 (CDR1d) | SEQ ID NO: 21 (CDR2d) | SEQ ID NO: 23 (CDR3d) |

In the aforementioned embodiment the order of the CDR sequences can be CDR1a-CDR2a-CDR3a-Linker1-CDR1b-CDR2b-CDR3b-Linker2-CDR1c-CDR2c-CDR3c-Linker3-

CDR1d-CDR2d-CDR3d; wherein Linker1, Linker2 and Linker3 are each polypeptides of at least 5 amino acids and wherein the polypeptide sequences of Linker1, Linker2 and Linker 3 are identical to each other or non-identical to each other. Preferably, Linker1, Linker2 and Linker3 are selected independently from each other from Table C below and most preferably at least one (preferably all three) of the linkers has/have the amino acid sequence according to SEQ ID NO: 35. It is understood that in the preferred embodiments outlined in the context of the two tables above the CDR sequences may be linked to each other via framework sequences as described elsewhere herein and preferably those framework sequences disclosed in Table A-2 may be used in this regard.

It will be appreciated that, without limitation, the immunoglobulin single variable domains of the present invention may be used as a "building block" for the preparation of a polypeptide, which may optionally contain one or more further immunoglobulin single variable domains that can serve as a building block.

The art is in need of more effective therapies for disorders affecting cartilage in joints, such as osteoarthritis. Even when administered intra-articularly, the residence time of most drugs for treating affected cartilage is insufficient. Without being bound by theory, the present inventors hypothesized that the efficacy of a therapeutic drug, such as a construct, polypeptide and ISVD of the invention, may be modulated by coupling the therapeutic drug to a moiety which would "anchor" the drug in the joint and consequently increase retention of the drug, but which should not disrupt the efficacy of said therapeutic drug (this moiety is herein also indicated as "cartilage anchoring protein" or "CAP"). This anchoring concept could not only modulate the efficacy of a drug, but also the operational specificity for a diseased joint by decreasing toxicity and side-effects, thus widening the number of possible useful drugs.

It was anticipated that a format of a molecule for clinical use comprises one or two building blocks, such as ISVDs, binding MMP13 and/or ADAMTS5 and one or more building blocks, e.g. ISVDs, with such a retention mode of action, and possibly further moieties. It is demonstrated in the present invention that such formats retain both MMP13 and/or ADAMTS5 binding and a therapeutic effect, e.g. inhibitory activity, as well as retention properties. The one or more building blocks, such as ISVDs, with a retention mode of action can be any building block having a retention effect ("CAP building block") in diseases in which MMP13 and/or ADAMTS5 is involved, such as arthritic disease, osteoarthritis, spondyloepimetaphyseal dysplasia, lumbar disk degeneration disease, Degenerative joint disease, rheumatoid arthritis, osteochondritis dissecans, aggrecanopathies.

A "CAP building block" is used for directing, anchoring and/or retaining other, e.g. therapeutic, building blocks, such as ISVDs binding MMP13 and/or ADAMTS5 at a desired site, such as e.g. in a joint, in which said other, e.g. therapeutic, building block is to exert its effect, e.g. binding and/or inhibiting MMP13 and/or ADAMTS5.

Again without being bound to theory, the present inventors further hypothesized that Aggrecan binders, such as ISVD(s) binding Aggrecan, might potentially function as such an anchor, although Aggrecan is heavily glycosylated and degraded in various disorders affecting cartilage in joints. Moreover, in view of the costs and extensive testing in various animal models required before a drug can enter the clinic, such Aggrecan binders should preferentially have a broad cross-reactivity, e.g. the Aggrecan binders should bind to Aggrecan of various species.

Using various ingenious immunization, screening and characterization methods, the present inventors were able to identify various Aggrecan binders with superior selectivity, stability and specificity features, which enabled prolonged retention and activity in the joint.

In an aspect, the present invention relates to a method for reducing and/or inhibiting the efflux of a composition, a polypeptide or a construct from a joint, wherein said method comprises administering a pharmaceutically active amount of at least one polypeptide according to the invention, a construct according to the invention, or a composition according to the invention to a person in need thereof.

In the present invention the term "reducing and/or inhibiting the efflux" means reducing and/or inhibiting the outward flow of the composition, polypeptide or construct from within a joint to the outside. Preferably, the efflux is reduced and/or inhibited by at least 10% such as at least 20%, 30%, 40% or 50% or even more such as at least 60%, 70%, 80%, 90% or even 100%, compared to the efflux of the aforementioned composition, polypeptide or construct in a joint under the same conditions but without the presence of the Aggrecan binder of the invention, e.g. ISVD(s) binding Aggrecan.

Next to the diseases in which MMP13 and/or ADAMTS5 is involved, such as arthritic disease, osteoarthritis, spondyloepimetaphyseal dysplasia, lumbar disk degeneration disease, Degenerative joint disease, rheumatoid arthritis, osteochondritis dissecans and aggrecanopathies it is anticipated that the Aggrecan binders of the invention can also be used in various other diseases affecting cartilage, such as arthropathies and chondrodystrophies, arthritic disease (such as osteoarthritis, rheumatoid arthritis, gouty arthritis, psoriatic arthritis, traumatic rupture or detachment), achondroplasia, costochondritis, Spondyloepimetaphyseal dysplasia, spinal disc herniation, lumbar disk degeneration disease, degenerative joint disease, and relapsing polychondritis (commonly indicated herein as "Aggrecan associated diseases").

Said CAP building block, e.g. ISVD(s) binding Aggrecan, preferably binds to cartilaginous tissue such as cartilage and/or meniscus. In a preferred aspect, the CAP building block is cross-reactive for other species and specifically binds one or more of human Aggrecan (SEQ ID NO: 68), dog Aggrecan, bovine Aggrecan, rat Aggrecan; pig Aggrecan; mouse Aggrecan, rabbit Aggrecan; cynomolgus Aggrecan and/or rhesus Aggrecan. Relevant structural information for Aggrecan may be found, for example, at (UniProt) Accession Numbers as depicted in the Table B-3 above.

A preferred CAP building block is an ISVD binding Aggrecan, preferably human Aggrecan, preferably represented by SEQ ID NO: 68 as depicted in Table B.

The present invention thus pertains to a polypeptide or construct according to the invention, further comprising at least one CAP building block.

The present invention thus pertains to a polypeptide or construct according to the invention, further comprising at least one ISVD specifically binding Aggrecan, preferably said ISVD is represented by SEQ ID NO: 4.

In an aspect the present invention relates to a polypeptide as described herein, comprising at least 2 ISVDs specifically binding Aggrecan.

In an aspect the present invention relates to a polypeptide as described herein, comprising at least 2 ISVDs specifically binding Aggrecan, wherein said at least 2 ISVDs specifically binding Aggrecan can be the same or different.

In an aspect the present invention relates to a polypeptide as described herein, comprising at least 2 ISVDs specifically binding Aggrecan, wherein each of said at least 2 ISVDs specifically binding Aggrecan is represented by SEQ ID NO: 4.

In an aspect the present invention relates to a polypeptide as described herein, comprising an ISVD specifically binding Aggrecan, wherein said ISVD specifically binding Aggrecan, specifically binds to human Aggrecan [SEQ ID NO: 68].

In an aspect the present invention relates to a polypeptide as described herein, wherein said ISVD specifically binding Aggrecan, specifically binds human Aggrecan (SEQ ID NO: 68), dog Aggrecan, bovine Aggrecan, rat Aggrecan, pig Aggrecan, mouse Aggrecan, rabbit Aggrecan, cynomolgus Aggrecan and/or rhesus Aggrecan.

In an aspect the present invention relates to a polypeptide as described herein, wherein said ISVD specifically binding Aggrecan preferably binds to cartilaginous tissue such as cartilage and/or meniscus.

It will be appreciated that the ISVD, polypeptide and construct of the invention is preferably stable. The stability of a polypeptide, construct or ISVD of the invention can be measured by routine assays known to the person skilled in the art. Typical assays include (without being limiting) assays in which the activity of said polypeptide, construct or ISVD is determined, followed by incubating in Synovial Fluid for a desired period of time, after which the activity is determined again.

In an aspect the present invention relates to an ISVD, polypeptide or construct of the invention having a stability of at least 7 days, such as at least 14 days, 21 days, 1 month, 2 months or even 3 months in synovial fluid (SF) at 37° C.

The desired activity of the therapeutic building block, e.g. an ISVD binding MMP13 and/or ADAMTS5 in the multivalent polypeptide or construct of the invention can be measured by routine assays known to the person skilled in the art. Typical assays include (without being limiting) GAG release assays as detailed in the Examples section.

The polypeptide of the invention (also indicated herein as "Nanobody construct") is chosen from the group consisting of (a) polypeptides comprising at least 2 immunoglobulin single variable domains (ISVDs), comprising a first ISVD specifically binding Aggrecan and a second ISVD specifically binding a matrix metalloproteinase (MMP);

(b) polypeptides comprising at least 2 ISVDs, comprising a first ISVD specifically binding Aggrecan and a second ISVD specifically binding an A Disintegrin and Metalloproteinase with Thrombospondin motifs (ADAMTS); and (c) polypeptides comprising at least 3 ISVDs, comprising a first ISVD specifically binding an Aggrecan, a second ISVD specifically binding an ADAMTS and a third ISVD specifically binding MMP.

In a polypeptide of the invention, the ISVDs may be directly linked or linked via a linker. Even more preferably, the polypeptide of the invention comprises a C-terminal extension. As will be detailed herein, the C-terminal extension essentially prevents/removes binding of pre-existing antibodies/factors in most samples of human subjects/patients. The C-terminal extension is present C-terminally of the last amino acid residue (usually a serine residue) of the last (most C-terminally located) ISVD.

As further elaborated infra, the ISVDs may be derived from a $V_{HH}$, $V_H$ or a $V_L$ domain, however, the ISVDs are chosen such that they do not form complementary pairs of $V_H$ and $V_L$ domains in the polypeptides of the invention. The Nanobody, $V_{HH}$, and humanized $V_{HH}$ are unusual in that they are derived from natural camelid antibodies which have no light chains, and indeed these domains are unable to associate with camelid light chains to form complementary $V_{HH}$ and $V_L$ pairs. Thus, the polypeptides of the present invention do not comprise complementary ISVDs and/or form complementary ISVD pairs, such as, for instance, complementary $V_H/V_L$ pairs.

Generally, polypeptides or constructs that comprise or essentially consist of a single building block, single ISVD or single Nanobody will be referred to as "monovalent" polypeptides and "monovalent constructs", respectively. Polypeptides or constructs that comprise two or more building blocks (such as e.g., ISVDs) will also be referred to as "multivalent" polypeptides or constructs, and the building blocks/ISVDs present in such polypeptides or constructs will also be referred to herein as being in a "multivalent format". For example, a "bivalent" polypeptide may comprise two ISVDs, optionally linked via a linker sequence, whereas a "trivalent" polypeptide may comprise three ISVDs, optionally linked via two linker sequences; whereas a "tetravalent" polypeptide may comprise four ISVDs, optionally linked via three linker sequences, etc.

In a multivalent polypeptide, the two or more ISVDs may be the same or different, and may be directed against the same antigen or antigenic determinant (for example against the same part(s) or epitope(s) or against different parts or epitopes) or may alternatively be directed against different antigens or antigenic determinants; or any suitable combination thereof, such as, e.g. directed against Aggrecan. Polypeptides and constructs that contain at least two building blocks (such as, e.g., ISVDs) in which at least one building block is directed against a first antigen (e.g., Aggrecan) and at least one building block is directed against a second antigen (i.e., different from Aggrecan, such as for instance directed against ADAMTS5) will also be referred to as "multispecific" polypeptides and constructs, and the building blocks (such as, e.g., ISVDs) present in such polypeptides and constructs will also be referred to herein as being in a "multispecific format". Thus, for example, a "bispecific" polypeptide of the invention is a polypeptide that comprises at least one ISVD directed against a first antigen (e.g., Aggrecan) and at least one further ISVD directed against a second antigen (i.e., different from Aggrecan, such as, for instance directed against ADAMTS5), whereas a "trispecific" polypeptide of the invention is a polypeptide that comprises at least one ISVD directed against a first antigen (e.g., Aggrecan), at least one further ISVD directed against a second antigen (i.e., different from Aggrecan such as e.g. directed against ADAMTS5) and at least one further ISVD directed against a third antigen (i.e., different from both Aggrecan and ADAMTS5, such as, e.g. directed against MMP); etc.

In an aspect, the present invention relates to a polypeptide, comprising at least 2 ISVDs, wherein at least one ISVD specifically binds an MMP, preferably MMP13, more preferably said one ISVD is represented by the amino acid sequence of SEQ ID NO: 2.

In an aspect, the present invention relates to a polypeptide, comprising at least 2 ISVDs, wherein at least one ISVD specifically binds an ADAMTS, preferably ADAMTS5, more preferably said one ISVD is represented by the amino acid sequence of SEQ ID NO: 3.

In an aspect, the present invention relates to a polypeptide, comprising at least 2 ISVDs, wherein at least one ISVD specifically binds Aggrecan more preferably said one ISVD is represented by the amino acid sequence of SEQ ID NO: 4.

"Multiparatopic" polypeptides and "multiparatopic" constructs, such as e.g., "biparatopic" polypeptides or constructs and "triparatopic" polypeptides or constructs, comprise or essentially consist of two or more building blocks that each have a different paratope.

The one or more ISVDs of the invention can be used as a building block in such a polypeptide or construct, so as to provide a monovalent, multivalent or multiparatopic polypeptide or construct of the invention, respectively, all as described herein.

The present invention thus also relates to a polypeptide or construct which is a multivalent polypeptide or multivalent construct, respectively, such as e.g., a bivalent or trivalent polypeptide or construct comprising or essentially consisting of two or more ISVDs of the invention (for multivalent and multispecific polypeptides containing one or more VHH domains and their preparation, reference is also made to Conrath et al. (J. Biol. Chem. 276: 7346-7350, 2001), as well as to for example WO 96/34103, WO 99/23221 and WO 2010/115998).

In another aspect, the multivalent polypeptide or construct of the invention may be a bispecific polypeptide or construct of the invention, comprising a first ISVD, such as a Nanobody, directed against Aggrecan, and a second ISVD, such as a Nanobody, directed against a second antigen, such as, for instance, ADAMTS5 or MMP13, in which said first and second ISVDs, such as Nanobodies, may optionally be linked via a linker sequence (as defined herein); whereas a multivalent polypeptide or construct of the invention may also be a trispecific polypeptide or construct of the invention, comprising a first ISVD, such as a Nanobody, directed against ADAMTS5, a second ISVD, such as a Nanobody, directed against a second antigen, such as, for instance Aggrecan, and a third ISVD, such as a Nanobody, directed against a third antigen, such as, for instance MMP13, in which said first, second and third ISVDs, such as Nanobodies, may optionally be linked via one or more, and in particular two, linker sequences.

The invention further relates to a multivalent polypeptide that comprises or (essentially) consists of at least one ISVD (or suitable fragments thereof) binding ADAMTS5, preferably human ADAMTS5, and one additional ISVD, such as an ISVD binding Aggrecan.

Particularly preferred bivalent, bispecific polypeptides or constructs and tetravalent, trispecific polypeptides or constructs in accordance with the invention are those shown in the Examples described herein and in Table A-1 (e.g. SEQ ID NO:s 1, 5, 6, 62, 63 or 64).

The two or more ISVDs present in the multivalent polypeptide or construct of the invention may consist of a light chain variable domain sequence (e.g., a $V_L$-sequence) or of a heavy chain variable domain sequence (e.g., a $V_H$-sequence); they may consist of a heavy chain variable domain sequence that is derived from a conventional four-chain antibody or of a heavy chain variable domain sequence that is derived from heavy chain antibody. In a preferred aspect, they consist of a Domain antibody (or an amino acid that is suitable for use as a domain antibody), of a single domain antibody (or an amino acid that is suitable for use as a single domain antibody), of a "dAb" (or an amino acid that is suitable for use as a dAb), of a Nanobody® (including but not limited to $V_{HH}$), of a humanized $V_{HH}$ sequence, of a camelized $V_H$ sequence; or of a $V_{HH}$ sequence that has been obtained by affinity maturation. The two or more immunoglobulin single variable domains may consist of a partially or fully humanized Nanobody or a partially or fully humanized VHH.

In a particularly preferred aspect, the polypeptide or construct of the invention comprises or essentially consists of four or more ISVDs, of which at least two ISVDs are directed against Aggrecan. It will be appreciated that said at least two ISVDs directed against Aggrecan can be the same or different, can be directed against the same epitope or different epitopes of Aggrecan, can belong to the same epitope bin or to different epitope bins, and/or can bind to the same or different domains of Aggrecan.

The relative affinities may depend on the location of the ISVDs in the polypeptide. It will be appreciated that the order of the ISVDs in a polypeptide of the invention (orientation) may be chosen according to the needs of the person skilled in the art. The order of the individual ISVDs as well as whether the polypeptide comprises a linker is a matter of design choice. Some orientations, with or without linkers, may provide preferred binding characteristics in comparison to other orientations. For instance, the order of a first ISVD (e.g. ISVD 1) and a second ISVD (e.g. ISVD 2) in the polypeptide of the invention may be (from N-terminus to C-terminus): (i) ISVD 1 (e.g. Nanobody 1)-[linker]-ISVD 2 (e.g. Nanobody 2)-[C-terminal extension]; or (ii) ISVD 2 (e.g. Nanobody 2)-[linker]-ISVD 1 (e.g. Nanobody 1)-[C-terminal extension]; (wherein the moieties between the square brackets, i.e. linker and C-terminal extension, are optional). All orientations are encompassed by the invention. Polypeptides that contain an orientation of ISVDs that provides desired binding characteristics may be easily identified by routine screening, for instance as exemplified in the examples section.

In a preferred order, the ISVD binding Aggrecan is located at the C-terminal side of the polypeptide. A particularly preferred order is from N-terminus to C-terminus: ISVD binding ADAMTS5-[linker]-ISVD binding Aggrecan-[C-terminal extension], or ISVD binding MMP13-[linker]-ISVD binding Aggrecan-[C-terminal extension], wherein the moieties between the square brackets are optional. A further particularly preferred order is from N-terminus to C-terminus: ISVD binding ADAMTS5-[linker]-ISVD binding Aggrecan-[linker]-ISVD binding Aggrecan-[C-terminal extension], or ISVD binding MMP13-[linker]-ISVD binding Aggrecan-[linker]-ISVD binding Aggrecan-[C-terminal extension], wherein the moieties between the square brackets are optional. For instance, a preferred order is from N-terminus to C-terminus: ISVD binding MMP13-[linker]-ISVD binding ADAMTS5-[linker]-ISVD binding Aggrecan-[C-terminal extension], wherein the moieties between the square brackets are optional. For instance, a particularly preferred order is from N-terminus to C-terminus: ISVD binding MMP13-[linker]-ISVD binding ADAMTS5-[linker]-ISVD binding Aggrecan-[linker]-ISVD binding Aggrecan—[C-terminal extension], wherein the moieties between the square brackets are optional.

In a further aspect, the invention relates to a polypeptide as described herein, wherein said polypeptide has at least 80%, 90%, 95% or 100% sequence identity with any of SEQ ID NO:s 1, 5, 6, 62, 63 or 64.

In an aspect, the present invention relates to a polypeptide as described herein, which is chosen from the group consisting of SEQ ID NO: 1 (ALX-1011), SEQ ID NO: 5 (MMP13-CAP-CAP), and SEQ ID NO: 6 (ATS5-CAP-CAP), SEQ ID NO: 62, SEQ ID NO: 63 and SEQ ID NO: 64.

In a specific aspect of the invention, a construct or polypeptide of the invention may have a moiety conferring an increased half-life, compared to the corresponding construct or polypeptide of the invention without said moiety. Some preferred, but non-limiting examples of such constructs and polypeptides of the invention will become clear to the skilled person based on the further disclosure herein, and for example comprise ISVDs or polypeptides of the invention that have been chemically modified to increase the half-life thereof (for example, by means of pegylation); the polypeptides or constructs of the invention that comprise at least one additional binding site for binding to a serum protein (such as serum albumin); or polypeptides of the invention which comprise at least one ISVD of the invention that is linked to at least one moiety (and in particular at least one amino acid sequence) which increases the half-life of the amino acid sequence of the invention. Examples of constructs of the invention and polypeptides of the invention comprising such half-life extending moieties or ISVDs will become clear to the skilled person based on the further disclosure herein; and for example include, without limitation, polypeptides in which the one or more ISVDs of the invention are suitably linked to one or more serum proteins or fragments thereof (such as (human) serum albumin or suitable fragments thereof) or to one or more binding units that can bind to serum proteins (such as, for example, domain antibodies, immunoglobulin single variable domains that are suitable for use as a domain antibody, single domain antibodies, ISVDs that are suitable for use as a single domain antibody, dAbs, ISVDs that are suitable for use as a dAb, or Nanobodies that can bind to serum proteins such as serum albumin (such as human serum albumin), serum immunoglobulins such as IgG, or transferrin; reference is made to the further description and references mentioned herein); polypeptides in which an amino acid sequence of the invention is linked to an Fc portion (such as a human Fc) or a suitable part or fragment thereof; or polypeptides in which the one or more immunoglobulin single variable domains of the invention are suitable linked to one or more small proteins or peptides that can bind to serum proteins, such as, for instance, the proteins and peptides described in WO 91/01743, WO 01/45746, WO 02/076489, WO2008/068280, WO2009/127691 and PCT/EP2011/051559.

In an aspect the present invention provides a polypeptide and construct of the invention, wherein said construct or said polypeptide further comprises a serum protein binding moiety or a serum protein. Preferably, said serum protein binding moiety binds serum albumin, such as human serum albumin.

In an aspect, the present invention relates to a polypeptide as described herein, comprising an ISVD binding serum albumin.

Generally, the constructs or polypeptides of the invention with increased half-life preferably have a half-life that is at least 1.5 times, preferably at least 2 times, such as at least 5 times, for example at least 10 times or more than 20 times, greater than the half-life of the corresponding constructs or polypeptides of the invention per se, i.e. without the moiety conferring the increased half-life. For example, the constructs or polypeptides of the invention with increased half-life may have a half-life e.g., in humans that is increased with more than 1 hour, preferably more than 2 hours, more preferably more than 6 hours, such as more than 12 hours, or even more than 24, 48 or 72 hours, compared to the corresponding constructs or polypeptides of the invention per se, i.e. without the moiety conferring the increased half-life.

In a preferred aspect of the invention, the constructs of the invention and polypeptides of the invention, have a serum half-life e.g. in humans that is increased with more than 1 hour, preferably more than 2 hours, more preferably more than 6 hours, such as more than 12 hours, or even more than 24, 48 or 72 hours, compared to the corresponding constructs or polypeptides of the invention per se, i.e. without the moiety conferring the increased half-life.

In another preferred aspect of the invention, such constructs and polypeptides of the invention exhibit a serum half-life in human of at least about 12 hours, preferably at least 24 hours, more preferably at least 48 hours, even more preferably at least 72 hours or more. For example, constructs or polypeptides of the invention may have a half-life of at least 5 days (such as about 5 to 10 days), preferably at least 9 days (such as about 9 to 14 days), more preferably at least about 10 days (such as about 10 to 15 days), or at least about 11 days (such as about 11 to 16 days), more preferably at least about 12 days (such as about 12 to 18 days or more), or more than 14 days (such as about 14 to 19 days).

In a particularly preferred aspect of the invention, the invention provides a construct of the invention and a polypeptide of the invention, comprising besides the one or more building blocks binding Aggrecan and the one or more building blocks binding ADAMTS5 and/or MMP13, at least one building block binding serum albumin, such as an ISVD binding serum albumin, such as human serum albumin as described herein. Preferably, said ISVD binding serum albumin comprises or essentially consists of 4 framework regions (FR1 to FR4, respectively) and 3 complementarity determining regions (CDR1 to CDR3 respectively), in which CDR1 is SFGMS, CDR2 is SISGSGSDTLYADSVKG and CDR3 is GGSLSR. Preferably, said ISVD binding human serum albumin is chosen from the group consisting of Alb8, Alb23, Alb129, Alb132, Alb11, Alb11 (S112K)-A, Alb82, Alb82-A, Alb82-AA, Alb82-AAA, Alb82-G, Alb82-GG, Alb82-GGG, Alb92 or Alb223 (cf. Table D).

In an embodiment, the present invention relates to a construct of the invention, such as a polypeptide comprising a serum protein binding moiety, wherein said serum protein binding moiety is a non-antibody based polypeptide.

In an aspect, the present invention relates to a construct as described herein comprising at least one ISVD or polypeptide and one or more other groups, residues, moieties or binding units. The one or more other groups, residues, moieties or binding units are preferably chosen from the group consisting of a polyethylene glycol molecule, serum proteins or fragments thereof, binding units that can bind to serum proteins, an Fc portion, and small proteins or peptides that can bind to serum proteins, further amino acid residues, tags or other functional moieties, e.g., toxins, labels, radiochemicals, etc.

In an embodiment, as mentioned infra, the present invention relates to a construct of the invention, such as a polypeptide comprising a moiety conferring half-life extension, wherein said moiety is a PEG. Hence, the present invention relates also to a construct or polypeptide of the invention comprising PEG.

The further amino acid residues may or may not change, alter or otherwise influence other (biological) properties of the polypeptide of the invention and may or may not add further functionality to the polypeptide of the invention. For example, such amino acid residues:

a) can comprise an N-terminal Met residue, for example as result of expression in a heterologous host cell or host organism.
b) may form a signal sequence or leader sequence that directs secretion of the polypeptide from a host cell upon synthesis (for example to provide a pre-, pro- or prepro-form of the polypeptide of the invention, depending on the host cell used to express the polypeptide of the invention). Suitable secretory leader peptides will be clear to the skilled person, and may be as further described herein. Usually, such a leader sequence will be linked to the N-terminus of the polypeptide, although the invention in its broadest sense is not limited thereto;
c) may form a "tag", for example an amino acid sequence or residue that allows or facilitates the purification of the polypeptide, for example using affinity techniques directed against said sequence or residue. Thereafter, said sequence or residue may be removed (e.g. by chemical or enzymatical cleavage) to provide the polypeptide (for this purpose, the tag may optionally be linked to the amino acid sequence or polypeptide sequence via a cleavable linker sequence or contain a cleavable motif). Some preferred, but non-limiting examples of such residues are multiple histidine residues, glutathione residues and a myc-tag such as AAAEQKLISEEDLNGAA;
d) may be one or more amino acid residues that have been functionalized and/or that can serve as a site for attachment of functional groups. Suitable amino acid residues and functional groups will be clear to the skilled person and include, but are not limited to, the amino acid residues and functional groups mentioned herein for the derivatives of the polypeptides of the invention.

Also encompassed in the present invention are constructs comprising a polypeptide and/or ISVD of the invention, which further comprise other functional moieties, e.g., toxins, labels, radiochemicals, etc.

The other groups, residues, moieties or binding units may for example be chemical groups, residues, moieties, which may or may not by themselves be biologically and/or pharmacologically active. For example, and without limitation, such groups may be linked to the one or more ISVDs or polypeptides of the invention so as to provide a "derivative" of the polypeptide or construct of the invention.

Accordingly, the invention in its broadest sense also comprises constructs and/or polypeptides that are derivatives of the constructs and/or polypeptides of the invention. Such derivatives can generally be obtained by modification, and in particular by chemical and/or biological (e.g., enzymatic) modification, of the constructs and/or polypeptides of the invention and/or of one or more of the amino acid residues that form a polypeptide of the invention.

Examples of such modifications, as well as examples of amino acid residues within the polypeptide sequences that can be modified in such a manner (i.e. either on the protein backbone but preferably on a side chain), methods and techniques that can be used to introduce such modifications and the potential uses and advantages of such modifications will be clear to the skilled person (see also Zangi et al., Nat Biotechnol 31(10):898-907, 2013).

For example, such a modification may involve the introduction (e.g., by covalent linking or in any other suitable manner) of one or more (functional) groups, residues or moieties into or onto the polypeptide of the invention, and in particular of one or more functional groups, residues or moieties that confer one or more desired properties or functionalities to the construct and/or polypeptide of the invention. Examples of such functional groups will be clear to the skilled person.

For example, such modification may comprise the introduction (e.g., by covalent binding or in any other suitable manner) of one or more functional moieties that increase the half-life, the solubility and/or the absorption of the construct or polypeptide of the invention, that reduce the immunogenicity and/or the toxicity of the construct or polypeptide of the invention, that eliminate or attenuate any undesirable side effects of the construct or polypeptide of the invention, and/or that confer other advantageous properties to and/or reduce the undesired properties of the construct or polypeptide of the invention; or any combination of two or more of the foregoing. Examples of such functional moieties and of techniques for introducing them will be clear to the skilled person, and can generally comprise all functional moieties and techniques mentioned in the general background art cited hereinabove as well as the functional moieties and techniques known per se for the modification of pharmaceutical proteins, and in particular for the modification of antibodies or antibody fragments (including ScFv's and single domain antibodies), for which reference is for example made to Remington (Pharmaceutical Sciences, 16$^{th}$ ed., Mack Publishing Co., Easton, Pa., 1980). Such functional moieties may for example be linked directly (for example covalently) to a polypeptide of the invention, or optionally via a suitable linker or spacer, as will again be clear to the skilled person.

One specific example is a derivative polypeptide or construct of the invention wherein the polypeptide or construct of the invention has been chemically modified to increase the half-life thereof (for example, by means of pegylation). This is one of the most widely used techniques for increasing the half-life and/or reducing the immunogenicity of pharmaceutical proteins and comprises attachment of a suitable pharmacologically acceptable polymer, such as poly(ethyleneglycol) (PEG) or derivatives thereof (such as methoxy-poly(ethyleneglycol) or mPEG). Generally, any suitable form of pegylation can be used, such as the pegylation used in the art for antibodies and antibody fragments (including but not limited to (single) domain antibodies and ScFv's); reference is made to, for example, Chapman (Nat. Biotechnol. 54: 531-545, 2002), Veronese and Harris (Adv. Drug Deliv. Rev. 54: 453-456, 2003), Harris and Chess (Nat. Rev. Drug. Discov. 2: 214-221, 2003) and WO 04/060965. Various reagents for pegylation of proteins are also commercially available, for example from Nektar Therapeutics, USA.

Preferably, site-directed pegylation is used, in particular via a cysteine-residue (see for example Yang et al. (Protein Engineering 16: 761-770, 2003). For example, for this purpose, PEG may be attached to a cysteine residue that naturally occurs in a polypeptide of the invention, a construct or polypeptide of the invention may be modified so as to suitably introduce one or more cysteine residues for attachment of PEG, or an amino acid sequence comprising one or more cysteine residues for attachment of PEG may be fused to the N- and/or C-terminus of a construct or polypeptide of the invention, all using techniques of protein engineering known per se to the skilled person.

Preferably, for the constructs or polypeptides of the invention, a PEG is used with a molecular weight of more than 5000, such as more than 10,000 and less than 200,000, such as less than 100,000; for example in the range of 20,000-80,000.

Another, usually less preferred modification comprises N-linked or O-linked glycosylation, usually as part of co-translational and/or post-translational modification, depending on the host cell used for expressing the polypeptide of the invention.

Yet another modification may comprise the introduction of one or more detectable labels or other signal-generating groups or moieties, depending on the intended use of the polypeptide or construct of the invention. Suitable labels and techniques for attaching, using and detecting them will be clear to the skilled person, and for example include, but are not limited to, fluorescent labels (such as fluorescein, isothiocyanate, rhodamine, phycoerythrin, phycocyanin, allophycocyanin, o-phthaldehyde, and fluorescamine and fluorescent metals, such as, $^{152}$Eu or others metals from the lanthanide series), phosphorescent labels, chemiluminescent labels or bioluminescent labels (such as luminal, isoluminol, theromatic acridinium ester, imidazole, acridinium salts, oxalate ester, dioxetane or GFP and its analogs), radio-isotopes (such as $^{3}$H, $^{125}$I, $^{32}$P, $^{35}$S, $^{14}$C, $^{51}$Cr, $^{36}$Cl, $^{57}$Co, $^{58}$Co, $^{59}$Fe, and $^{75}$Se), metals, metal-chelates or metallic cations (for example metallic cations such as $^{99m}$Tc, $^{123}$I, $^{111}$In, $^{131}$I, $^{97}$Ru, $^{67}$Cu, $^{67}$Ga, and $^{68}$Ga or other metals or metallic cations that are particularly suited for use in in vivo, in vitro or in situ diagnosis and imaging, such as ($^{157}$Gd, $^{55}$Mn, $^{162}$Dy, $^{52}$Cr, and $^{56}$Fe)), as well as chromophores and enzymes (such as malate dehydrogenase, staphylococcal nuclease, delta-V-steroid isomerase, yeast alcohol dehydrogenase, alpha-glycerophosphate dehydrogenase, triose phosphate isomerase, biotinavidin peroxidase, horseradish peroxidase, alkaline phosphatase, asparaginase, glucose oxidase, β-galactosidase, ribonuclease, urease, catalase, glucose-VI-phosphate dehydrogenase, glucoamylase and acetylcholine esterase). Other suitable labels will be clear to the skilled person, and for example include moieties that can be detected using NMR or ESR spectroscopy.

Such labelled polypeptides and constructs of the invention may, for example, be used for in vitro, in vivo or in situ assays (including immunoassays known per se such as ELISA, RIA, EIA and other "sandwich assays", etc.) as well as in vivo diagnostic and imaging purposes, depending on the choice of the specific label.

As will be clear to the skilled person, another modification may involve the introduction of a chelating group, for example to chelate one of the metals or metallic cations referred to above. Suitable chelating groups for example include, without limitation, diethyl-enetriaminepentaacetic acid (DTPA) or ethylene-diaminetetraacetic acid (EDTA).

Yet another modification may comprise the introduction of a functional moiety that is one part of a specific binding pair, such as the biotin-(strept)avidin binding pair. Such a functional moiety may be used to link the polypeptide of the invention to another protein, polypeptide or chemical compound that is bound to the other half of the binding pair, i.e. through formation of the binding pair. For example, a construct or polypeptide of the invention may be conjugated to biotin, and linked to another protein, polypeptide, compound or carrier conjugated to avidin or streptavidin. For example, such a conjugated construct or polypeptide of the invention may be used as a reporter, for example in a diagnostic system where a detectable signal-producing agent is conjugated to avidin or streptavidin. Such binding pairs may for example also be used to bind the construct or polypeptide of the invention to a carrier, including carriers suitable for pharmaceutical purposes. One non-limiting example is the liposomal formulations described by Cao and Suresh (Journal of Drug Targeting 8: 257, 2000). Such binding pairs may also be used to link a therapeutically active agent to the polypeptide of the invention.

Other potential chemical and enzymatical modifications will be clear to the skilled person. Such modifications may also be introduced for research purposes (e.g. to study function-activity relationships). Reference is for example made to Lundblad and Bradshaw (Biotechnol. Appl. Biochem. 26: 143-151, 1997).

Preferably, the constructs, polypeptides and/or derivatives are such that they bind to Aggrecan and ADAMTS5 and/or MMP13, with an affinity (suitably measured and/or expressed as a $K_D$-value (actual or apparent), a $K_A$-value (actual or apparent), a $k_{on}$-rate or on-rate and/or $k_{off}$ or off-rate, or alternatively as an $IC_{50}$ value, as further described herein) that is as defined herein (e.g. as defined for the polypeptides of the invention).

Such constructs and/or polypeptides of the invention and derivatives thereof may also be in essentially isolated form (as defined herein).

In an aspect, the present invention relates to a construct of the invention, that comprises or essentially consists of an ISVD according to the invention or a polypeptide according to the invention, and which further comprises one or more other groups, residues, moieties or binding units, which are optionally linked via one or more peptidic linkers.

In an aspect, the present invention relates to a construct of the invention, in which one or more other groups, residues, moieties or binding units are chosen from the group consisting of a polyethylene glycol molecule, serum proteins or fragments thereof, binding units that can bind to serum proteins, an Fc portion, and small proteins or peptides that can bind to serum proteins.

In the constructs of the invention, such as the polypeptides of the invention, the two or more building blocks, such as e.g. ISVDs, and the optionally one or more other groups, drugs, agents, residues, moieties or binding units may be directly linked to each other (as for example described in WO 99/23221) and/or may be linked to each other via one or more suitable spacers or linkers, or any combination thereof. Suitable spacers or linkers for use in multivalent and multispecific polypeptides will be clear to the skilled person, and may generally be any linker or spacer used in the art to link amino acid sequences. Preferably, said linker or spacer is suitable for use in constructing constructs, proteins or polypeptides that are intended for pharmaceutical use.

For instance, the polypeptide of the invention may, for example, be a trivalent, trispecific polypeptide, comprising one building block, such as an ISVD binding Aggrecan, an ISVD binding ADAMTS5, and potentially another building block, such as a third ISVD binding MMP13, in which said first, second and third building blocks, such as ISVDs, may optionally be linked via one or more, and in particular 2, linker sequences. Also, the present invention provides a construct or polypeptide of the invention comprising a first ISVD binding Aggrecan and possibly a second ISVD binding Aggrecan and/or possibly a third ISVD ADAMTS5 and/or possibly a fourth ISVD binding MMP13, wherein said first ISVD and/or said second ISVD and/or possibly said third ISVD and/or possibly said fourth ISVD are linked via linkers, in particular 3 linkers.

Some particularly preferred linkers include the linkers that are used in the art to link antibody fragments or antibody domains. These include the linkers mentioned in the general background art cited above, as well as for example linkers that are used in the art to construct diabodies or ScFv fragments (in this respect, however, it should be noted that, whereas in diabodies and in ScFv fragments, the linker sequence used should have a length, a degree of flexibility and other properties that allow the pertinent $V_H$ and $V_L$ domains to come together to form the complete antigen-binding site, there is no particular limitation on the length or the flexibility of the linker used in the polypeptide of the invention, since each ISVD, such as Nanobodies, by itself forms a complete antigen-binding site).

For example, a linker may be a suitable amino acid sequence, and in particular amino acid sequences of between 1 and 50, preferably between 1 and 30, such as between 1 and 10 amino acid residues. Some preferred examples of such amino acid sequences include gly-ser linkers, for example of the type $(gly_x ser_y)_2$, such as (for example $(gly_4 ser)_3$ or $(gly_3 ser_2)_3$, as described in WO 99/42077 and the GS30, GS15, GS9 and GS7 linkers described in the applications by Ablynx mentioned herein (see for example WO 06/040153 and WO 06/122825), as well as hinge-like regions, such as the hinge regions of naturally occurring heavy chain antibodies or similar sequences (such as described in WO 94/04678). Preferred linkers are depicted in Table C.

Some particularly preferred linkers are GS9 (see also SEQ ID NO: 84 in WO 06/122825) and GS35, as well as poly-alanine (such as AAA) and the linker GS30 (see also SEQ ID NO: 85 in WO 06/122825).

Other suitable linkers generally comprise organic compounds or polymers, in particular those suitable for use in proteins for pharmaceutical use. For instance, poly(ethyleneglycol) moieties have been used to link antibody domains, see for example WO 04/081026.

It is encompassed within the scope of the invention that the length, the degree of flexibility and/or other properties of the linker(s) used (although not critical, as it usually is for linkers used in ScFv fragments) may have some influence on the properties of the final the construct of the invention, such as the polypeptide of the invention, including but not limited to the affinity, specificity or avidity for a chemokine, or for one or more of the other antigens. Based on the disclosure herein, the skilled person will be able to determine the optimal linker(s) for use in a specific construct of the invention, such as the polypeptide of the invention, optionally after some limited routine experiments.

For example, in multivalent polypeptides of the invention that comprise building blocks, ISVDs or Nanobodies directed against Aggrecan and another target such as e.g. ADAMTS5 and/or MMP13, the length and flexibility of the linker are preferably such that it allows each building block, such as an ISVD, of the invention present in the polypeptide to bind to its cognate target, e.g. the antigenic determinant on each of the targets. Again, based on the disclosure herein, the skilled person will be able to determine the optimal linker(s) for use in a specific construct of the invention, such as a polypeptide of the invention, optionally after some limited routine experiments.

It is also within the scope of the invention that the linker(s) used, confer one or more other favourable properties or functionality to the constructs of the invention, such as the polypeptides of the invention, and/or provide one or more sites for the formation of derivatives and/or for the attachment of functional groups (e.g. as described herein for the derivatives of the ISVDs of the invention). For example, linkers containing one or more charged amino acid residues can provide improved hydrophilic properties, whereas linkers that form or contain small epitopes or tags can be used for the purposes of detection, identification and/or purification. Again, based on the disclosure herein, the skilled person will be able to determine the optimal linkers for use in a specific polypeptide of the invention, optionally after some limited routine experiments.

Finally, when two or more linkers are used in the constructs such as polypeptides of the invention, these linkers may be the same or different. Again, based on the disclosure herein, the skilled person will be able to determine the optimal linkers for use in a specific construct or polypeptide of the invention, optionally after some limited routine experiments.

Usually, for the ease of expression and production, a construct of the invention, such as a polypeptide of the invention, will be a linear polypeptide. However, the invention in its broadest sense is not limited thereto. For example, when a construct of the invention, such as a polypeptide of the invention, comprises three of more building blocks, ISVDs or Nanobodies, it is possible to link them by use of a linker with three or more "arms", which each "arm" being linked to a building block, ISVD or Nanobody, so as to provide a "star-shaped" construct. It is also possible, although usually less preferred, to use circular constructs.

Accordingly, the present invention relates to a construct of the invention, such as a polypeptide of the invention, wherein said ISVDs are directly linked to each other or are linked via a linker.

Accordingly, the present invention relates to a construct of the invention, such as a polypeptide of the invention, wherein a first ISVD and/or a second ISVD and/or possibly an ISVD binding serum albumin are linked via a linker.

Accordingly, the present invention relates to a construct of the invention, such as a polypeptide of the invention, wherein said linker is chosen from the group consisting of linkers of 9GS, 35GS, 3A, 5GS, 7GS, 10GS, 15GS, 18GS, 20GS, 25GS, 30GS, poly-A, 8GS, 40GS, G1 hinge, 9GS-G1 hinge, llama upper long hinge region, and G3 hinge, such as e.g. presented in Table C (SEQ ID NO:s 28, 35, 24-27, 29-34 and 36-40).

Accordingly, the present invention relates to a construct of the invention, such as a polypeptide of the invention, wherein said polypeptide is chosen from the group consisting of SEQ ID NOs: 62-64, 1, 5 and 6.

The invention further relates to methods for preparing the constructs, polypeptides, ISVDs, nucleic acids, host cells, and compositions described herein.

The multivalent polypeptides of the invention can generally be prepared by a method which comprises at least the step of suitably linking the ISVD and/or monovalent polypeptide of the invention to one or more further ISVDs, optionally via the one or more suitable linkers, so as to provide the multivalent polypeptide of the invention. Polypeptides of the invention can also be prepared by a method which generally comprises at least the steps of providing a nucleic acid that encodes a polypeptide of the invention, expressing said nucleic acid in a suitable manner, and recovering the expressed polypeptide of the invention. Such methods can be performed in a manner known per se, which will be clear to the skilled person, for example on the basis of the methods and techniques further described herein.

A method for preparing multivalent polypeptides of the invention may comprise at least the steps of linking two or more ISVDs of the invention and for example one or more linkers together in a suitable manner. The ISVDs of the invention (and linkers) can be coupled by any method known in the art and as further described herein. Preferred techniques include the linking of the nucleic acid sequences that encode the ISVDs of the invention (and linkers) to prepare a genetic construct that expresses the multivalent polypeptide. Techniques for linking amino acids or nucleic acids will be clear to the skilled person, and reference is again made to the standard handbooks, such as Sambrook et al. and Ausubel et al., mentioned above, as well as the Examples below.

Accordingly, the present invention also relates to the use of an ISVD of the invention in preparing a multivalent polypeptide of the invention. The method for preparing a multivalent polypeptide will comprise the linking of an ISVD of the invention to at least one further ISVD of the invention, optionally via one or more linkers. The ISVD of the invention is then used as a binding domain or building block in providing and/or preparing the multivalent polypeptide comprising 2 (e.g., in a bivalent polypeptide), 3 (e.g., in a trivalent polypeptide), 4 (e.g., in a tetravalent) or more (e.g., in a multivalent polypeptide) building blocks. In this respect, the ISVD of the invention may be used as a binding domain or binding unit in providing and/or preparing a multivalent, such as bivalent, trivalent or tetravalent polypeptide of the invention comprising 2, 3, 4 or more building blocks.

Accordingly, the present invention also relates to the use of an ISVD polypeptide of the invention (as described herein) in preparing a multivalent polypeptide. The method for the preparation of the multivalent polypeptide will comprise the linking of the ISVD of the invention to at least one further ISVD of the invention, optionally via one or more linkers.

The polypeptides and nucleic acids of the invention can be prepared in a manner known per se, as will be clear to the skilled person from the further description herein. For example, the polypeptides of the invention can be prepared in any manner known per se for the preparation of antibodies and in particular for the preparation of antibody fragments (including but not limited to (single) domain antibodies and ScFv fragments). Some preferred, but non-limiting methods for preparing the polypeptides and nucleic acids include the methods and techniques described herein.

The method for producing a polypeptide of the invention may comprise the following steps: the expression, in a suitable host cell or host organism (also referred to herein as a "host of the invention") or in another suitable expression system of a nucleic acid that encodes said polypeptide of the invention (also referred to herein as a "nucleic acid of the invention"); optionally followed by isolating and/or purifying the polypeptide of the invention thus obtained.

In particular, such a method may comprise the steps of: cultivating and/or maintaining a host of the invention under conditions that are such that said host of the invention expresses and/or produces at least one polypeptide of the invention; optionally followed by isolating and/or purifying the polypeptide of the invention thus obtained.

Accordingly, the present invention also relates to a nucleic acid or nucleotide sequence that encodes a polypeptide, ISVD or construct of the invention (also referred to as "nucleic acid of the invention").

A nucleic acid of the invention can be in the form of single or double stranded DNA or RNA. According to one embodiment of the invention, the nucleic acid of the invention is in essentially isolated from, as defined herein. The nucleic acid of the invention may also be in the form of, be present in and/or be part of a vector, e.g. expression vector, such as for example a plasmid, cosmid or YAC, which again may be in essentially isolated form. Accordingly, the present invention also relates to an expression vector comprising a nucleic acid or nucleotide sequence of the invention.

The nucleic acids of the invention can be prepared or obtained in a manner known per se, based on the information on the polypeptides of the invention given herein, and/or can be isolated from a suitable natural source. Also, as will be clear to the skilled person, to prepare a nucleic acid of the invention, also several nucleotide sequences, such as at least two nucleic acids encoding ISVDs of the invention and for example nucleic acids encoding one or more linkers can be linked together in a suitable manner. Techniques for generating the nucleic acids of the invention will be clear to the skilled person and may for instance include, but are not limited to, automated DNA synthesis; site-directed mutagenesis; combining two or more naturally occurring and/or synthetic sequences (or two or more parts thereof), introduction of mutations that lead to the expression of a truncated expression product; introduction of one or more restriction sites (e.g. to create cassettes and/or regions that may easily be digested and/or ligated using suitable restriction enzymes), and/or the introduction of mutations by means of a PCR reaction using one or more "mismatched" primers. These and other techniques will be clear to the skilled person, and reference is again made to the standard handbooks, such as Sambrook et al. and Ausubel et al., mentioned above, as well as to the Examples below.

In a preferred but non-limiting embodiment, a genetic construct of the invention comprises a) at least one nucleic acid of the invention;
b) operably connected to one or more regulatory elements, such as a promoter and optionally a suitable terminator; and optionally also
c) one or more further elements of genetic constructs known per se; in which the terms "regulatory element", "promoter", "terminator" and "operably connected" have their usual meaning in the art.

The genetic constructs of the invention may generally be provided by suitably linking the nucleotide sequence(s) of the invention to the one or more further elements described above, for example using the techniques described in the general handbooks such as Sambrook et al. and Ausubel et al., mentioned above.

The nucleic acids of the invention and/or the genetic constructs of the invention may be used to transform a host cell or host organism, i.e., for expression and/or production of the polypeptide of the invention. Suitable hosts or host cells will be clear to the skilled person, and may for example be any suitable fungal, prokaryotic or eukaryotic cell or cell line or any suitable fungal, prokaryotic or (non-human) eukaryotic organism as well as all other host cells or (non-human) hosts known per se for the expression and production of antibodies and antibody fragments (including but not limited to (single) domain antibodies and ScFv fragments), which will be clear to the skilled person. Reference is also made to the general background art cited hereinabove, as well as to for example WO 94/29457; WO 96/34103; WO 99/42077; Frenken et al. (Res Immunol. 149: 589-99, 1998); Riechmann and Muyldermans (1999), supra; van der Linden (J. Biotechnol. 80: 261-70, 2000); Joosten et al. (Microb. Cell Fact. 2: 1, 2003); Joosten et al. (Appl. Microbiol. Biotechnol. 66: 384-92, 2005); and the further references cited herein. Furthermore, the polypeptides of the invention can also be expressed and/or produced in cell-free expression systems, and suitable examples of such systems will be clear to the skilled person. Suitable techniques for transforming a host or host cell of the invention will be clear to the skilled person and may depend on the intended host cell/host organism and the genetic construct to be used. Reference is again made to the handbooks and patent applications mentioned above. The transformed host cell (which may be in the form or a stable cell line) or host organisms (which may be in the form of a stable mutant line or strain) form further aspects of the present invention. Accordingly, the present invention relates to a host or host cell comprising a nucleic acid according to the invention, or an expression vector according to the invention. Preferably, these host cells or host organisms are such that they express, or are (at least) capable of expressing (e.g., under suitable conditions), a polypeptide of the invention (and in case of a host organism: in at least one cell, part, tissue or organ thereof). The invention also includes further generations, progeny and/or offspring of the host cell or host organism of the invention, that may for instance be obtained by cell division or by sexual or asexual reproduction.

To produce/obtain expression of the polypeptides of the invention, the transformed host cell or transformed host organism may generally be kept, maintained and/or cultured under conditions such that the (desired) polypeptide of the invention is expressed/produced. Suitable conditions will be clear to the skilled person and will usually depend upon the host cell/host organism used, as well as on the regulatory elements that control the expression of the (relevant) nucleotide sequence of the invention. Again, reference is made to the handbooks and patent applications mentioned above in the paragraphs on the genetic constructs of the invention.

The polypeptide of the invention may then be isolated from the host cell/host organism and/or from the medium in which said host cell or host organism was cultivated, using protein isolation and/or purification techniques known per se, such as (preparative) chromatography and/or electrophoresis techniques, differential precipitation techniques, affinity techniques (e.g., using a specific, cleavable amino acid sequence fused with the polypeptide of the invention) and/or preparative immunological techniques (i.e. using antibodies against the polypeptide to be isolated).

In an aspect the invention relates to method for producing a construct, polypeptide or ISVD according to the invention comprising at least the steps of: (a) expressing, in a suitable host cell or host organism or in another suitable expression system, a nucleic acid sequence according to the invention; optionally followed by (b) isolating and/or purifying the construct, polypeptide or ISVD according to the invention.

In an aspect the invention relates to a composition comprising a construct, polypeptide, ISVD or nucleic acid according to the invention.

As mentioned supra, there remains a need for safe and efficacious OA medicaments. First, the present inventors identified very effective cartilage anchoring proteins, i.e. ISVDs binding Aggrecan, which were used as building blocks to engineer molecules which bound ADAMTS5 and/or MMP13 as well. The resulting molecules had an increased retention in a subject and could be administered systemically while retaining activity. The present inventors subsequently demonstrated that a combination of both ADAMTS5 inhibitors as well as MMP13 inhibitors was more effective in ameliorating OA than inhibiting either target alone. Moreover, the polypeptides and constructs of the invention were also demonstrated to be significantly more efficacious than the prior art compounds.

The present invention thus provides compositions, constructs and/or polypeptides with improved prophylactic, therapeutic and/or pharmacological properties, including a safer profile, compared to prior art amino acid sequences and antibodies.

In an aspect the present invention relates to a method of treating or prevention of diseases or disorders in an individual, for instance in which ADAMTS5 and/or MMP13 activity is involved, the method comprising administering a composition, polypeptide and/or construct according to the invention to said individual in an amount effective to treat or prevent (a symptom of) said disease or disorder.

In an aspect the present invention relates to a composition according to the invention, a polypeptide according to the invention, and/or a construct according to the invention for use as a medicament.

In another aspect, the invention relates to the use of a composition, polypeptide and/or construct according to the invention in the preparation of a pharmaceutical composition for prevention and/or treatment of at least an ADAMTS5 and/or MMP13 associated disease, such as OA; and/or for use in one or more of the methods of treatment mentioned herein.

The invention also relates to the use of a composition, polypeptide and/or construct according to the invention in the preparation of a pharmaceutical composition for the prevention and/or treatment of at least one disease or disorder that can be prevented and/or treated by modulating the activity of an ADAMTS, preferably inhibiting an activity of ADAMTS5.

The invention also relates to the use of a composition, polypeptide and/or construct according to the invention in the preparation of a pharmaceutical composition for the prevention and/or treatment of at least one disease or disorder that can be prevented and/or treated by modulating the activity of an MMP, preferably inhibiting the activity of MMP13.

The invention also relates to the use of an ISVD, polypeptide, composition and/or construct of the invention in the preparation of a pharmaceutical composition for the prevention and/or treatment of at least one disease, disorder or condition that can be prevented and/or treated by administering an ISVD, polypeptide, composition and/or construct of the invention to a patient.

The invention further relates to an ISVD, composition, polypeptide and/or construct of the invention or a pharmaceutical composition comprising the same for use in the prevention and/or treatment of at least an ADAMTS5 associated disease and/or MMP13 associated disease.

It is anticipated that the ADAMTS5 binders of the invention can be used in various diseases affecting cartilage, such as arthropathies and chondrodystrophies, arthritic disease, such as osteoarthritis, rheumatoid arthritis, gouty arthritis, psoriatic arthritis, traumatic rupture or detachment, achondroplasia, costochondritis, spondyloepimetaphyseal dysplasia, spinal disc herniation, lumbar disk degeneration disease, degenerative joint disease, and relapsing polychondritis, osteochondritis dissecans and aggrecanopathies and non-alcoholic steatohepatitis (NASH) (commonly indicated herein as "ADAMTS5 associated diseases"), preferably OA.

It is anticipated that the MMP13 binders of the invention can be used in various diseases affecting cartilage, such as arthropathies and chondrodystrophies, arthritic disease, such as osteoarthritis, rheumatoid arthritis, gouty arthritis, psoriatic arthritis, traumatic rupture or detachment, achondroplasia, costochondritis, spondyloepimetaphyseal dysplasia, spinal disc herniation, lumbar disk degeneration disease, degenerative joint disease, relapsing polychondritis, osteochondritis dissecans, aggrecanopathies, chronic periodontitis and abdominal aortic aneurysms (commonly indicated herein as "MMP13 associated diseases"), preferably OA.

In an aspect the present invention relates to a composition, an ISVD, a polypeptide and/or a construct according to the invention for use in treating or preventing a symptom of an ADAMTS5 associated disease and/or MMP13 associated disease, such as e.g. arthropathies and chondrodystrophies, arthritic disease, such as osteoarthritis, rheumatoid arthritis, gouty arthritis, psoriatic arthritis, traumatic rupture or detachment, achondroplasia, costochondritis, spondyloepimetaphyseal dysplasia, spinal disc herniation, lumbar disk degeneration disease, degenerative joint disease, relapsing polychondritis, osteochondritis dissecans, aggrecanopathies, NASH, chronic periodontitis and abdominal aortic aneurysms, preferably OA.

In an aspect the present invention relates to a method for preventing or treating arthropathies and chondrodystrophies, arthritic disease, such as osteoarthritis, rheumatoid arthritis, gouty arthritis, psoriatic arthritis, traumatic rupture or detachment, achondroplasia, costochondritis, spondyloepimetaphyseal dysplasia, spinal disc herniation, lumbar disk degeneration disease, degenerative joint disease, relapsing polychondritis, NASH, chronic periodontitis and abdominal aortic aneurysms, preferably OA, wherein said method comprises administering, to a subject in need thereof, a pharmaceutically active amount of at least a composition, immunoglobulin, polypeptide and/or construct according to the invention to a person in need thereof.

In an aspect the present invention relates to the use of an ISVD, polypeptide, composition and/or construct according to the invention, in the preparation of a pharmaceutical composition for treating or preventing a disease or disorder such as arthropathies and chondrodystrophies, arthritic disease, such as osteoarthritis, rheumatoid arthritis, gouty arthritis, psoriatic arthritis, traumatic rupture or detachment, achondroplasia, costochondritis, spondyloepimetaphyseal dysplasia, spinal disc herniation, lumbar disk degeneration disease, degenerative joint disease, relapsing polychondritis, osteochondritis dissecans, aggrecanopathies, NASH, chronic periodontitis and abdominal aortic aneurysms, preferably OA.

It is also expected that by binding to Aggrecan, the ISVDs, constructs and/or polypeptides of the invention may reduce or inhibit an activity of a member of the serine protease family, cathepsins, matrix metallo-proteinases (MMPs other than MMP13), such as e.g. MMP20, but also ADAMTS4 (Aggrecanase-1) and/or ADAMTS11 in degrading Aggrecan.

In the context of the present invention, the term "prevention and/or treatment" not only comprises preventing and/or treating the disease, but also generally comprises preventing the onset of the disease, slowing or reversing the progress of disease, preventing or slowing the onset of one or more symptoms associated with the disease, reducing and/or alleviating one or more symptoms associated with the disease, reducing the severity and/or the duration of the disease and/or of any symptoms associated therewith and/or preventing a further increase in the severity of the disease and/or of any symptoms associated therewith, preventing, reducing or reversing any physiological damage caused by the disease, and generally any pharmacological action that is beneficial to the patient being treated.

The dosage regimen will be determined by the attending physician and clinical factors. As is well known in the medical arts, dosage for any one patient depends upon many factors, including the patient's size, weight, body surface area, age, the particular compound to be administered, the activity of the employed polypeptide (including antibodies), time and route of administration, general health, and combination with other therapies or treatments. Proteinaceous pharmaceutically active matter may be present in amounts between 1 g and 100 mg/kg body weight per dose; however, doses below or above this exemplary range are also envisioned. If the regimen is a continuous infusion, it may be in the range of 1 pg to 100 mg per kilogram of body weight per minute.

An ISVD, polypeptide or construct of the invention may be employed at a concentration of, e.g., 0.01, 0.1, 0.5, 1, 2, 5, 10, 20 or 50 pg/ml in order to inhibit and/or neutralize an activity of ADAMTS5 and/or MMP13 by at least about 50%, preferably 75%, more preferably 90%, 95% or up to 99%, and most preferably approximately 100% (essentially completely) as assayed by methods well known in the art.

Generally, the treatment regimen will comprise the administration of one or more polypeptides and/or constructs of the invention, or of one or more compositions comprising the same, in one or more pharmaceutically effective amounts or doses. The specific amounts) or doses to be administered can be determined by the clinician, again based on the factors cited above. Useful dosages of the compositions, constructs and/or polypeptides of the invention can be determined by comparing their in vitro activity, and in vivo activity in animal models. Methods for the extrapolation of effective dosages in mice, and other animals, to humans are known to the art; for example, see U.S. Pat. No. 4,938,949.

Generally, depending on the specific disease, disorder or condition to be treated, the potency of the specific polypeptide and/or construct of the invention to be used, the specific route of administration and the specific pharmaceutical formulation or composition used, the clinician will be able to determine a suitable dosing regimen.

The amount of the compositions, constructs and/or polypeptides of the invention required for use in treatment will vary not only with the particular composition, polypeptide and/or construct selected but also with the route of administration, the nature of the condition being treated and the age and condition of the patient and will be ultimately at the discretion of the attendant physician or clinician. Also the dosage of the compositions, constructs and/or polypeptides of the invention varies depending on the target cell, tissue or organ.

The desired dose may conveniently be presented in a single dose or—less preferred—as divided doses administered at appropriate intervals, for example, as two, three, four or more sub-doses per day. The sub-dose itself may be further divided, e.g., into a number of discrete loosely spaced administrations.

An administration regimen could include long-term, daily treatment. By "long-term" is meant at least two weeks and preferably, several weeks, months, or years of duration. Necessary modifications in this dosage range may be determined by one of ordinary skill in the art using only routine experimentation given the teachings herein. See Remington's Pharmaceutical Sciences (Martin, E. W., ed. 4), Mack Publishing Co., Easton, Pa. The dosage can also be adjusted by the individual physician in the event of any complication. It has been shown that the compositions, polypeptides and constructs are extremely stable and remain efficacious for extended periods of time.

Usually, in the above method, a composition, polypeptide and/or construct of the invention will be used. It is however within the scope of the invention to use two or more compositions, polypeptides and/or constructs of the invention in combination, such as, for instance, a combination of SEQ ID NO:s 5 and 6, SEQ ID NO:s 63 and 64, SEQ ID NO:s 5 and 64, or SEQ ID NO:s 63 and 6.

The compositions, polypeptides and/or constructs of the invention may be used in combination with one or more further pharmaceutically active compounds or principles, i.e., as a combined treatment regimen, which may or may not lead to a synergistic effect.

The pharmaceutical composition may also comprise at least one further active agent, e.g. one or more further antibodies or antigen-binding fragments thereof, peptides, proteins, nucleic acids, organic and inorganic molecules.

Again, the clinician will be able to select such further compounds or principles, as well as a suitable combined treatment regimen, based on the factors cited above and his expert judgment.

In particular, the compositions, polypeptides and/or constructs of the invention may be used in combination with other pharmaceutically active compounds or principles that are or can be used for the prevention and/or treatment of the diseases, disorders and conditions cited herein, as a result of which a synergistic effect may or may not be obtained. Examples of such compounds and principles, as well as routes, methods and pharmaceutical formulations or compositions for administering them will be clear to the clinician.

When two or more substances or principles, such as for instance (a composition comprising) a polypeptide comprising an ISVD inhibiting ADAMTS5 and another polypeptide comprising an ISVD inhibiting MMP13, are to be used as part of a combined treatment regimen, such as, for instance, a combination of SEQ ID NO:s 5 and 6, SEQ ID NO:s 63 and 64, SEQ ID NO:s 5 and 64, or SEQ ID NO:s 63 and 6, they can be administered via the same route of administration or via different routes of administration, at essentially the same time or at different times (e.g. essentially simultaneously, consecutively, or according to an alternating regime). When the substances or principles are to be administered simultaneously via the same route of administration, they may be administered as different pharmaceutical formulations or compositions or part of a combined pharmaceutical formulation or composition, as will be clear to the skilled person.

Also, when two or more active substances or principles are to be used as part of a combined treatment regimen, such as, for instance a (composition comprising a) polypeptide comprising an ISVD inhibiting ADAMTS5 and another polypeptide comprising an ISVD inhibiting MMP13, each of the substances or principles may be administered in the same amount and according to the same regimen as used when the compound or principle is used on its own, and such combined use may or may not lead to a synergistic effect. However, when the combined use of the two or more active substances or principles leads to a synergistic effect, it may also be possible to reduce the amount of one, more or all of the substances or principles to be administered, while still achieving the desired therapeutic action. This may for example be useful for avoiding, limiting or reducing any unwanted side-effects that are associated with the use of one or more of the substances or principles when they are used in their usual amounts, while still obtaining the desired pharmaceutical or therapeutic effect.

The effectiveness of the treatment regimen used according to the invention may be determined and/or followed in any manner known per se for the disease, disorder or condition involved, as will be clear to the clinician. The clinician will also be able, where appropriate and on a case-by-case basis, to change or modify a particular treatment regimen, so as to achieve the desired therapeutic effect, to avoid, limit or reduce unwanted side-effects, and/or to achieve an appropriate balance between achieving the desired therapeutic effect on the one hand and avoiding, limiting or reducing undesired side effects on the other hand.

Generally, the treatment regimen will be followed until the desired therapeutic effect is achieved and/or for as long as the desired therapeutic effect is to be maintained. Again, this can be determined by the clinician.

Thus, in a further aspect, the invention relates to a pharmaceutical composition that contains at least one construct of the invention or at least one polypeptide of the invention and at least one suitable carrier, diluent or excipient (i.e., suitable for pharmaceutical use), and optionally one or more further active substances. In a particular aspect, the invention relates to a pharmaceutical composition that comprises at least one composition, construct or polypeptide according to the invention, preferably at least one of SEQ ID NOs: 1 and 62, or a combination of SEQ ID NO:s 5 and 6, SEQ ID NO:s 63 and 64, SEQ ID NO:s 5 and 64, or SEQ ID NO:s 63 and 6, and at least one suitable carrier, diluent or excipient suitable for pharmaceutical use), and optionally one or more further active substances.

The subject to be treated may be any warm-blooded animal, but is in particular a mammal, and more in particular a human being. In veterinary applications, the subject to be treated includes any animal raised for commercial purposes or kept as a pet. As will be clear to the skilled person, the subject to be treated will in particular be a person suffering from, or at risk of, the diseases, disorders and conditions mentioned herein. Hence, in a preferred embodiment of the invention, the pharmaceutical compositions comprising a polypeptide of the invention are for use in medicine or diagnostics. Preferably, the pharmaceutical compositions are for use in human medicine, but they may also be used for veterinary purposes.

Again, in such a pharmaceutical composition, the one or more compositions, polypeptides and/or constructs of the invention, or nucleotide encoding the same, and/or a pharmaceutical composition comprising the same, may also be suitably combined with one or more other active principles, such as those mentioned herein.

The invention also relates to a composition (such as, without limitation, a pharmaceutical composition or preparation as further described herein) for use, either in vitro (e.g. in an in vitro or cellular assay) or in vivo (e.g. in an a single cell or multi-cellular organism, and in particular in a mammal, and more in particular in a human being, such as in a human being that is at risk of or suffers from a disease, disorder or condition of the invention).

It is to be understood that reference to treatment includes both treatment of established symptoms and prophylactic treatment, unless explicitly stated otherwise.

Generally, for pharmaceutical use, the compositions, constructs, polypeptides and/or ISVDs of the invention may be formulated as a pharmaceutical preparation or composition comprising at least one construct, polypeptide and/or ISVD of the invention and at least one pharmaceutically acceptable carrier, diluent or excipient and/or adjuvant, and optionally one or more pharmaceutically active polypeptides and/or compounds. By means of non-limiting examples, such a formulation may be in a form suitable for oral administration, for parenteral administration (such as by intra-articular, intravenous, intramuscular or subcutaneous injection or intravenous infusion), for topical administration, for administration by inhalation, by a skin patch, by an implant, by a suppository, etc., wherein the parenteral administration is preferred. Such suitable administration forms—which may be solid, semi-solid or liquid, depending on the manner of administration—as well as methods and carriers for use in the preparation thereof, will be clear to the skilled person, and are further described herein. Such a pharmaceutical preparation or composition will generally be referred to herein as a "pharmaceutical composition".

As exemplary excipients, disintegrators, binders, fillers, and lubricants may be mentioned. Examples of disintegrators include agar-agar, algins, calcium carbonate, cellulose, colloid silicon dioxide, gums, magnesium aluminium silicate, methylcellulose, and starch. Examples of binders include micro-crystalline cellulose, hydroxymethyl cellulose, hydroxypropylcellulose, and polyvinylpyrrolidone. Examples of fillers include calcium carbonate, calcium phosphate, tribasic calcium sulfate, calcium carboxymethylcellulose, cellulose, dextrin, dextrose, fructose, lactitol, lactose, magnesium carbonate, magnesium oxide, maltitol, maltodextrins, maltose, sorbitol, starch, sucrose, sugar, and xylitol. Examples of lubricants include agar, ethyl oleate, ethyl laureate, glycerin, glyceryl palmitostearate, hydrogenated vegetable oil, magnesium oxide, stearates, mannitol, poloxamer, glycols, sodium benzoate, sodium lauryl sulfate, sodium stearyl, sorbitol, and talc. Usual stabilizers, preservatives, wetting and emulsifying agents, consistency-improving agents, flavour-improving agents, salts for varying the osmotic pressure, buffer substances, solubilizers, diluents, emollients, colorants and masking agents and antioxidants come into consideration as pharmaceutical adjuvants.

Suitable carriers include but are not limited to magnesium carbonate, magnesium stearate, talc, sugar, lactose, pectin, dextrin, starch, gelatine, tragacanth, methylcellulose, sodium carboxymethyl-cellulose, a low melting-point wax, cocoa butter, water, alcohols, polyols, glycerol, vegetable oils and the like.

Generally, the constructs, polypeptides, and/or ISVDs of the invention can be formulated and administered in any suitable manner known per se. Reference is for example made to the general background art cited above (and in particular to WO 04/041862, WO 04/041863, WO 04/041865, WO 04/041867 and WO 08/020079) as well as to the standard handbooks, such as Remington's Pharmaceutical Sciences, 18$^{th}$ Ed., Mack Publishing Company, USA (1990), Remington, the Science and Practice of Pharmacy, 21st Edition, Lippincott Williams and Wilkins (2005); or the Handbook of Therapeutic Antibodies (S. Dubel, Ed.), Wiley, Weinheim, 2007 (see for example pages 252-255).

In a particular aspect, the invention relates to a pharmaceutical composition that comprises at least a composition, construct, polypeptide, ISVD or nucleic acid according to the invention, and which further comprises at least one pharmaceutically acceptable carrier, diluent or excipient and/or adjuvant, and optionally comprises one or more further pharmaceutically active polypeptides and/or constructs.

The compositions, constructs, polypeptides, and/or ISVDs of the invention may be formulated and administered in any manner known per se for conventional antibodies and antibody fragments (including ScFv's and diabodies) and other pharmaceutically active proteins. Such formulations and methods for preparing the same will be clear to the skilled person, and for example include preparations preferable for suitable for parenteral administration (e.g. intra-articular, intravenous, intraperitoneal, subcutaneous, intramuscular, intraluminal, intra-arterial, intrathecal intranasal or intrabronchial administration) but also for topical (i.e., transdermal or intradermal) administration.

Preparations for parenteral administration may for example be sterile solutions, suspensions, dispersions or emulsions that are suitable for infusion or injection. Suitable carriers or diluents for such preparations for example include, without limitation, those mentioned on page 143 of WO 08/020079. Usually, aqueous solutions or suspensions will be preferred.

The compositions, constructs, polypeptides, and/or ISVDs of the invention can also be administered using methods of delivery known from gene therapy, see, e.g., U.S. Pat. No. 5,399,346, which is incorporated by reference for its gene therapy delivery methods. Using a gene therapy method of delivery, primary cells transfected with the gene encoding a construct, polypeptide, and/or ISVD of the invention can additionally be transfected with tissue specific promoters to target specific organs, tissue, grafts, tumors, or cells and can additionally be transfected with signal and stabilization sequences for subcellularly localized expression.

According to further aspects of the invention, the compositions, constructs and/or polypeptide of the invention may be used in additional applications in vivo and in vitro. For example, compositions, constructs and/or polypeptides of the invention may be employed for diagnostic purposes, e.g. in assays designed to detect and/or quantify the presence of ADAMTS5 and/or MMP13 and/or to purify ADAMTS5 and/or MMP13. The compositions, polypeptides and/or constructs may also be tested in animal models of particular diseases and for conducting toxicology, safety and dosage studies.

Finally, the invention relates to a kit comprising at least one composition, polypeptide or construct according to the invention, at least one nucleic acid sequence encoding said components, the vector or vector system of the invention, and/or a host cell according to the invention. It is contemplated that the kit may be offered in different forms, e.g. as a diagnostic kit.

The invention will now be further described by means of the following non-limiting preferred aspects, examples and figures.

The entire contents of all of the references (including literature references, issued patents, published patent applications, and co-pending patent applications) cited throughout this application are hereby expressly incorporated by reference, in particular for the teaching that is referenced hereinabove.

Sequences are disclosed in the main body of the description and in a separate sequence listing according to WIPO standard ST.25. A SEQ ID specified with a specific number should be the same in the main body of the description and in the separate sequence listing. By way of example SEQ ID no.: 1 should define the same sequence in both, the main body of the description and in the separate sequence listing.

Sequences are disclosed in the main body of the description and in a separate sequence listing according to WIPO standard ST.25. A SEQ ID specified with a specific number should be the same in the main body of the description and in the separate sequence listing. By way of example SEQ ID no.: 1 should define the same sequence in both, the main body of the description and in the separate sequence listing. Should there be a discrepancy between a sequence definition in the main body of the description and the separate sequence listing (if e.g. SEQ ID no.: 1 in the main body of the description erroneously corresponds to SEQ ID no.: 2 in the separate sequence listing) then a reference to a specific sequence in the application, in particular of specific embodiments, is to be understood as a reference to the sequence in the main body of the application and not to the separate sequence listing. In other words a discrepancy between a sequence definition/designation in the main body of the description and the separate sequence listing is to be resolved by correcting the separate sequence listing to the sequences and their designation disclosed in the main body of the application which includes the description, examples, figures and claims.

6 EXAMPLES

Without being bound by theory the inventors hypothesized that inhibiting both ADAMTS5 and MMP13 would potentially be more efficacious in that
(1) a broader range of OA-inducing and sustaining proteases would be inhibited;
(2) a broader range of patients can be targeted, e.g. without the need for separating patients in different groups; and
(3) a broader range of disease development can be treated.

For patient friendliness, the inhibitors are preferably retained and active in the joints for prolonged periods.

Accordingly, the inventors set out to isolate and characterize ISVDs specifically binding MMP13, ISVDs specifically binding ADAMTS5 as well as ISVDs specifically binding Aggrecan. Subsequently, ISVDs were combined in different formats and tested in various in vitro, ex vivo and in vivo models.

Example 1 MMP13 ISVDs 1.1 anti-MMP13 ISVD 62CO2

After screening more than 10E7 clones, the MMP13 specific ISVD 62CO2 was identified in fluorogenic peptide assays, collagenolytic assays and fluorogenic collagen assays.

In brief, the setup of human, cynomolgus, rat, dog and bovine MMP13 fluorogenic peptide assays, as well as human MMP1 and MMP14 fluorogenic peptide assays is as follows. Activated MMP was incubated with fluorogenic peptide substrate Mca-PLGL-Dpa-AR-NH2 (R&D Systems #ES001) and a ⅕ dilution of periplasmic extract or a dilution series of purified Nanobody/positive control (total volume=20 µl in assay buffer 50 mM Tris pH 7.5, 100 mM NaCl, 10 mM CaCl2, 0.01% Tween20), for 2 h at 37° C. The linear increase of fluorescence (v0-between 15 and 45 min incubation) was used as a measure for the enzymatic activity and % inhibition was calculated with the formula 100-100 (v0 in the presence of test Nanobody/v0 in the presence of negative control Nanobody (Cablys)).

The setup of the Collagenolytic assay is in brief as follows: 250 ng/ml immunization grade human Collagen II (Chondrex #20052) was incubated with 5 nM activated MMP13 in 100 µl assay buffer (50 mM Tris-Cl pH 7.5, 100 mM NaCl, 10 mM CaCl2, 0.01% Tween-20). After 1.5 h incubation at 35° C., the reaction was neutralized with EDTA (10 µl of 30 mM stock). MMP13 cleaved Collagen was further degraded with elastase for 20 min at 38° C. to avoid re-annealing of degraded Collagen II (10 µl of ⅓ diluted stock provided in Type II Collagen Detection kit (Chondrex #6009)). Remaining intact Collagen was detected via ELISA (reagents provided in Type II Collagen Detection kit (Chondrex #6009)).

The setup of the fluorogenic Collagen assay is in essence as follows: 100 µg/ml DQ™ Collagen, type I from Bovine skin (fluorescein conjugate; Molecular Probes #D-12060 lot 1149062) was incubated with 10 nM activated MMP13 and a dilution series of purified Nanobody/positive control, for 2 h at 37° C. in 40 µl assay buffer (50 mM Tris-Cl pH 7.5, 100 mM NaCl, 10 mM CaCl$_2$, 0.01% Tween-20). The linear increase of fluorescence (v0-between 15 and 45 min incubation) was used as a measure for the enzymatic activity and % inhibition was calculated with the formula 100-100 (v0 in the presence of test Nanobody/v0 in the presence of a negative control Nanobody (Cablys)).

In order to further characterize ISVD 62C02, this ISVD was recloned into the vector pAX129, transformed into E. coli and expressed and purified according to standard protocols (e.g. Maussang et al. 2013 J Biol Chem 288: 29562-72). Subsequently, this ISVD was subjected to various functional in vitro assays. TIMP-2, which is a non-selective MMP inhibitor, was used as positive control in these assays. As positive comparator, the small molecule drug MSC2392891A was used. An overview of the potencies in the enzymatic assays is given in Table 1.1.

TABLE 1.1

| | IC50 [nM] | | | | | | |
|---|---|---|---|---|---|---|---|
| clone | human fluorogenic peptide assay | rat fluorogenic peptide assay | dog fluorogenic peptide assay | bovine fluorogenic peptide assay | cyno fluorogenic peptide assay | human collagenolytic assay | human fluorogenic collagen assay |
| TIMP-2 | 0.5 | 0.4 | 0.9 | 1.1 | 0.4 | 0.4 | 2.4 |
| 62C02 | 1.4 | 1.1 | 1.0 | 3.1 | 1.4 | 1.4 | 8.3 |
| MSC2392891A | 3.7 | 0.7 | 0.7 | 8.5 | 3.0 | 4.7 | partial inhibition |

In conclusion, ISVD 62C02 performed better in all assays relative to the comparator drug MSC2392891A.

1.2 anti-MMP13 ISVD 62C02 is selective

In order to determine the selectivity of ISVD 62C02 for MMP13, fluorogenic peptide assays for MMP1 and MMP14 were used. MMP1 and MMP14 are two closely related MMP family members. TIMP-2 was used as positive control in these assays. A similar set up as described in Example 1.1 was used.

It was demonstrated that ISVD 62C02 was highly selective, showing no MMP1 or MMP14 inhibition (data not shown).

Example 2 ADAMTS5 ISVD 2.1 anti-ADAMTS5 ISVD 02F03

Also in this case, more than 10E7 clones were screened, in order to identify ISVD 02F03, which specifically binds ADAMTS5. ISVD 02F03 was further characterized for inhibiting ADAMTS5-mediated cleavage of Aggrecan via FRET-based and AlphaLISA assays.

In short, a periplasmic extract of ISVD 02F03 was tested for binding to recombinant human ADAMTS5 by binding ELISA. Next, it was confirmed that ISVD 02F03 was able to prevent ADAMTS5-mediated cleavage of Aggrecan in a FRET-based human ADAMTS5 enzymatic assay. Next to the FRET-based assay, an AlphaLISA (Perkin Elmer, Waltham, Mass., US) based human ADAMTS5 assay with a biotinylated 43-mer Aggrecan oligopeptide as substrate was performed. Upon ADAMTS5 cleavage of this substrate, a biotinylated ARGSV neo-epitope product is released and can be detected by streptavidin-AlphaScreen donor beads and an α-neo-epitope ("ARGSV") antibody captured on anti-mouse IgG-coated AlphaLISA acceptor beads, resulting in the generation of a luminescence AlphaScreen signal upon laser excitation.

To determine the ability of ISVD 02F03 to prevent ADAMTS5-mediated cleavage of the substrate, the decrease in signal was analysed in function of ISVD 02F03 concentration and $IC_{50}$ values were calculated. The small molecule MSC2310852A, which inhibits both ADAMTS4 activity and ADAMTS5 activity, was used as a positive control.

The results are summarized in Table 2.1.1.

TABLE 2.1.1

Potency ($IC_{50}$) and % inhibition of ADAMTS5 for ISVD 02F03 and reference compounds in human FRET and AlphaLISA enzymatic assays

| Compound ID | Human FRET | | Human AlphaLISA | |
|---|---|---|---|---|
| | IC50 [M] | % inhibition | IC50 [M] | % inhibition |
| mAb 12F4 H4L0 | 1.0E−09 | 75 | 6.5E−11 | 100 |
| 02F03 | 1.8E−09 | 89 | 7.5E−11 | 100 |
| MSC2310852A | 6.0E−08 | 100 | 1.4E−07 | 99 |

Results are summarized in Table 2.1.2.

TABLE 2.1.2

$IC_{50}$ value for ISVD 02F03 in the bovine explant assay.

| ID | IC50 [M] |
|---|---|
| mAb 12F4 H4L0 | 3.2E−06 |
| 02F03 | 1.4E−08 |

In this ex vivo assay, the ISVD 02F03 showed a better potency than the bivalent mAb 12F4, i.e. the $IC_{50}$ is about 50 times lower.

Species cross-reactivity was initially evaluated via SPR-based off-rate analysis on a Biacore T100 instrument. Polypeptides were tested for binding to human, cynomolgus monkey ("cyno"), guinea pig, mouse, and bovine ADAMTS5. To this end, recombinant ADAMTS5 was immobilized onto a CM5 chip via amine coupling using EDC and NHS. Purified ISVD 02F03 was injected for 2 minutes at a concentration of 100 nM and allowed to dissociate for 15 min at a flow rate of 45 μl/min. Off-rate for each individual ADAMTS5 was determined by fitting a 1:1 interaction model (Langmuir model) onto the individual dissociation curves using the BIA Evaluation software. As a reference, off-rates on human ADAMTS5 were determined in each experiment.

The results are summarized in Table 2.1.3.

TABLE 2.1.3

Overview of species cross-reactivity data of ISVD 02F03

| | SPR based off-rate, kd (1/s) on ADAMTS-5 | | | | | | |
|---|---|---|---|---|---|---|---|
| | Experiment 1 | | | Experiment 2 | | Experiment 3 | |
| Nanobody ID | Human | Cyno | Guinea pig | Human | Mouse | Human | Bovine |
| 02F03 | 3.3E−05 | 2.2E−05 | 3.4E−05 | 6.5E−05 | 2.9E−04 | 9.7E−05 | 4.3E−05 |

While being comparable to the bivalent mAb 12F4, the ISVD 02F03 showed a better potency than the small molecule MSC2310852A.

In addition, ISVD 02F03 was further evaluated for its ability to block cartilage degradation in an ex vivo assay, in which the substrate is presented in a condition closer to the physiological condition compared to biochemical assays. In brief, bovine cartilage explant chips (diameter 4 mm) were prepared freshly from cow knee joints and incubated in 96-well plates in presence of IL-1α to induce cartilage degradation. As a measure of cartilage/Aggrecan degradation, the release of glycosaminoglycan (GAG) was detected in the supernatant after 5 days of incubation (37° C., 7.5% CO2) via the metachromatic dye 1,9 dimethylmethylene blue (emission at 633 nm). Chondroitin sulphate was included as assay standard. Efficacy was defined by means of the IL-1α-induced controls without compound (0%) and in presence of MSC2310852A (100% effect).

The ISVD 02F03 showed comparable off-rates (cross-reactivity) with human, cynomolgus, guinea pig and bovine ADAMTS5.

2.2 Selectivity of ISVD 02F03

To confirm the selectivity of ISVD 02F03 for ADAMTS5, inhibition of the enzymatic activity of MMP1, MMP14 and ADAMTS4 was evaluated via FRET-based assays and a human ADAMTS4 AlphaLISA, with the respective enzymes.

Activated human MMP1 or MMP14 was incubated for 30 minutes at room temperature with 10 μl of dilution series of ISVD 02F03. After incubation, 20 μl of respectively 5 μM or 2.5 μM fluorogenic peptide substrate (Mca-PLGL-Dpa-AR-NH2 Fluorogenic MMP Substrate (R&D Systems cat #E5001)) was added. The ability of ISVD 02F03 to prevent MMP1- and MMP14-mediated cleavage was monitored every minute for 2 hours at 37° C. on a Tecan Infinite M1000 plate reader.

Whereas the natural inhibitors TIMP2 and TIMP3 inhibited MMP1 and MMP14 activity, ISVD 02F03 did not show any inhibition (data not shown).

To evaluate inhibition of human ADAMTS4, an assay similar to the human ADAMTS5 AlphaLISA was carried out, essentially as described in Example 2.1, but using human ADAMTS4 (R&D Systems, Minneapolis, US; cat #4307-AD). To determine the ability of ISVD 02F03 to prevent human ADAMTS4-mediated cleavage of the substrate, the decrease in signal was analysed in function of ISVD 02F03 concentration and $IC_{50}$ values were calculated.

Whereas the small molecule MSC2310852A inhibited human ADAMTS4 activity, ISVD 02F03 or mAb 12F4 did not show any inhibitory activity (data not shown). The monoclonal antibody mAb 12F4 (H4L0) was described to be selective over ADAMTS4 in WO 2011/002968.

Example 3 Aggrecan ISVDs 3.1 Anti-Aggrecan ISVD 114F08

The Aggrecan-specific ISVD 114F08 was isolated and characterized after extensive screening campaigns. Llamas were immunized with recombinant human Aggrecan (G1-IGD-G2 domains, R&D Systems #1220-PG) and gave specific and high serum titers. However, only a minute fraction of the isolated Nanobodies satisfied the two requirements of binding to the G1-domain of Aggrecan and showing broad species cross-reactivity. After arduous attempts, various family members were identified showing essentially similar characteristics (see Table 3.1A to Table 3.1C for sequence variation in the CDRs). Eventually, ISVD 114F08 ("C0101PMP114F08") was selected for further characterization.

An overview of the domain-mapping and species cross-reactivity data is provided in Table 3.1.1.

TABLE 3.1.1

| Mapping | Clone | Periplasmic extract ELISA. OD 450 nm | | | | |
| --- | --- | --- | --- | --- | --- | --- |
| | | Hu G1-IGD-G2 | Cy G1-IGD-G2 | Rat G1-IGD-G2 | Dog G1-IGD-G2 | Bov G1-IGD-G2 |
| G1 | 114F08 | 2.38 | 2.32 | 2.05 | 1.90 | 1.18 |

After the primary screening, initial assessment of binding via ELISA, determination of off-rate and species cross-reactivity, ISVD 114F08 was subjected to further characterization.

The sequence variability in the CDRs of the family members of ISVD 114F08 is depicted in Tables 3.1A, 3.1B and 3.1C below. The amino acid sequences of the CDRs of clone 114F08 were used as reference, against which the CDRs of all other family members were compared (CDR1 starts at Kabat position 26, CDR2 starts at Kabat position 50, and CDR3 starts at Kabat position 95).

TABLE 3.1A

| 114F08 | CDR1* | | | | | | | | | |
| --- | --- | --- | --- | --- | --- | --- | --- | --- | --- | --- |
| Kabat numbering | 26 | 27 | 28 | 29 | 30 | 31 | 32 | 33 | 34 | 35 |
| absolute numbering | 1 | 2 | 3 | 4 | 5 | 6 | 7 | 8 | 9 | 10 |
| wildtype sequence | G | S | T | F | I | I | N | V | V | R |
| mutations | | | | | | | S | | M | |

*Up to 2 CDR1 mutations in one clone

TABLE 3.1B

| 114F08 | CDR2* | | | | | | | | |
| --- | --- | --- | --- | --- | --- | --- | --- | --- | --- |
| Kabat numbering | 50 | 51 | 52 | 53 | 54 | 55 | 56 | 57 | 58 |
| absolute numbering | 1 | 2 | 3 | 4 | 5 | 6 | 7 | 8 | 9 |
| wildtype sequence | T | I | S | S | G | G | N | A | N |
| mutations | A | | R | T | | | | T | D |

*Up to 5 CDR2 mutations in one clone

TABLE 3.1C

| 114F08 | CDR3* | | | | | | | | | | | | |
| --- | --- | --- | --- | --- | --- | --- | --- | --- | --- | --- | --- | --- | --- |
| Kabat numbering | 95 | 96 | 97 | 98 | 99 | 100 | 100a | 100b | 100c | 100d | 100e | 100f | 100g |
| absolute numbering | 1 | 2 | 3 | 4 | 5 | 6 | 7 | 8 | 9 | 10 | 11 | 12 | 13 |

TABLE 3.1C-continued

| 114F08 | CDR3* | | | | | | | | | | | |
|---|---|---|---|---|---|---|---|---|---|---|---|---|
| wildtype sequence | P | T | T | H | Y | G | G | V | Y | Y | G | P | Y |
| mutations | . | . | . | R | . | . | . | D | . | . | . | . | . |

*Up to 2 CDR3 mutations in one clone 3.2 Ex Vivo Bovine Cartilage Retention

Since there is no established assay for assessing cartilage retention, the inventors developed an ex vivo cartilage retention assay using bovine cartilage.

The ability of a polypeptides comprising ISVD 114F08 to be retained in the cartilage for a prolonged period of time, following a relatively short exposure of a polypeptide to the cartilage (which can be expected upon intra-articular injection), was determined. The assay was typically performed with 4 cartilage discs per Nanobody sample; 2 discs were analysed right after the polypeptide incubation ($t_0$) to determine the initial amount of bound polypeptide; 2 discs were analysed after washing ($t_{1-5\ days}$). The degree of retention was defined as the ratio of the amount of polypeptide detected at $t_{1-5\ days}$ and $t_0$. The determination of this ratio was performed by visual inspection of the Western Blots giving a score from 0-6, where 0 is no retention and 6 is full retention. A dummy construct C0101030 ("30"), consisting of 2 inactive ISVDs ALB26, showed no binding.

A summary of the results is shown in Table 3.2.

TABLE 3.2

Cartilage retention of the ALB26-formatted anti-Aggrecan ISVD 114F08. *Scores are an average of 1 to 4 independent ex vivo bovine cartilage retention assays on a scale from 0-6: 0 is no retention and 6 is full retention.

| Target | Construct | Description | Cartilage retention * |
|---|---|---|---|
| G1 | 118 | ALB26-114F08-114F08 | 6.0 |
| G1 | 54 | 114F08-ALB26 | 5.0 |
| Dummy | 30 | ALB26-ALB26 | 0.0 |

It was found that polypeptides comprising ISVD 114F08 were retained very well (scores 5-6) in the cartilage. This included constructs comprising both one and two binding units of ISVD 114F08.

3.3 Binding Characteristics—ELISA

Based on the ex vivo bovine cartilage retention data, ISVD 114F08 was further characterized in ELISA on the recombinant G1-IGD-G2 region from human, cynomolgus, rat, dog and bovine Aggrecan to determine its species cross-reactivity (see also Example 3.1) and on recombinant human Neurocan and Brevican to determine its selectivity. The determined $EC_{50}$ values are listed in Table 3.3.

TABLE 3.3

Characterization of the ALB26-formatted anti-Aggrecan ISVD 114F08 by ELISA.

| | | EC50 (M) | | | | | | |
|---|---|---|---|---|---|---|---|---|
| Construct | Description | Human | Cyno | Rat | Dog | Bovine | Neurocan | Brevican |
| 54 | 114F08-ALB26 | 6.0E−09 | 4.4E−09 | 7.6E−09 | 3.0E−09 | 5.6E−09 | No bind | No bind |
| 118 | ALB26-114F08-114F08 | 1.1E−10 | 7.6E−11 | 1.9E−10 | 2.4E−10 | 3.7E−10 | No bind | No bind |
| Dummy | ALB26-ALB26 | No bind | No bind | No bind | No bind | No bind | No bind | No bind |

3.4 Tissue Specificity

It was demonstrated above that the polypeptides of the invention bind specifically to Aggrecan in vitro and to cartilage ex vivo. In addition, these polypeptides should also bind preferably to the cartilage of a joint, while not or less to other tissues in a joint.

Binding of polypeptides comprising ISVD 114F08 to synovial membrane, tendon and epimysium was assessed using the same set up as for the ex vivo cartilage binding assay. Polypeptide release and Western Blot analysis were performed following a brief wash of the tissues (30 min) after ON incubation with the polypeptides.

The results are summarized in Table 3.4.

TABLE 3.4

Tissue specificity. Binding of the ALB26-formatted anti-Aggrecan ISVD 114F08 to articular cartilage, synovial membrane, tendon and epimysium. Scores are on a scale from 0-6, in which 0 is no binding and 6 is maximum observed binding.

| Construct | Description | Cartilage | Synovial membrane | Tendon | Epimysium |
|---|---|---|---|---|---|
| 054 | 114F08-ALB26 | 6 | 1 | 1 | 1 |
| 118 | ALB26-114F08-114F08 | 6 | 1 | 1 | 1 |
| Dummy | ALB26-ALB26 | 1 | 1 | 1 | 0 |

The results show that polypeptides comprising either one or two binding units of ISVD 114F08 show preferential binding to cartilage, over the other tissues found in the joint.

3.5 Nanobody Stability in Bovine Synovial Fluid

For various reasons, including patient convenience and safety, it is preferred that the polypeptides remain stable for longer periods in the synovium.

Accordingly, the stability of polypeptides comprising ISVD 114F08 in Synovial Fluid (SF) was assessed by incubation of the polypeptides in bovine SF for up to 7 days at 37° C.

The results are summarized in Table 3.5.

TABLE 3.5

Stability of polypeptides comprising ISVD 114F08 in bovine SF.

| Construct | Description | Stability in bovine SF, 37° C. |
|---|---|---|
| 054 | 114F08-ALB26 | >7 days |
| 118 | ALB26-114F08-114F08 | >7 days |
| Dummy | ALB26-ALB26 | >7 days |

No degradation of any of the constructs could be detected.

Example 4 Polypeptides

Polypeptide 754 was engineered by genetically linking anti-MMP13 ISVD 62C02 and two anti-Aggrecan ISVDs 114F08, using 35GS linkers (M-C-C). Polypeptide 754-9 was similar to polypeptide 754, but now using 9GS linkers. The resulting amino acid sequences are shown in Table A-1 as SEQ ID NO: 5 and 63, respectively.

Polypeptide 954 was engineered by genetically linking anti-ADAMTS5 ISVD 2F03 and two anti-Aggrecan ISVDs 114F08, using 35GS linkers (A-C-C). Polypeptide 954-9 (cf. "973") was similar to polypeptide 954, but now using 9GS linkers. The resulting amino acid sequences are shown in Table A-1 as SEQ ID NO: 6 and 64, respectively.

Polypeptide 949 was engineered by genetically linking anti-MMP13 ISVD 62C02, anti-ADAMTS5 ISVD 2F03 and two anti-Aggrecan ISVDs 114F08, using 35GS linkers (M-A-C-C). Polypeptide 949-9 was similar to polypeptide 949, but now using 9GS linkers. The resulting amino acid sequences are shown in Table A-1 as SEQ ID NO: 1 and 62, respectively.

Example 5 Affinity of Polypeptides for ADAMTS5, MMP13 and Aggrecan of Different Species

5.1 Affinity of polypeptide 949 towards human, cynomolgus and rat ADAMTS5

The in solution affinity of polypeptide 949 for human, cynomolgus and rat ADAMTS5 was determined using KinExA. A fixed concentration of 20 pM (final concentration) polypeptide 949 was equilibrated for 24 hours with a 16-point 1/2.2 serially diluted dose response curve of human, cynomolgus or rat ADAMTS5, each time starting at 20 nM with the last point being a blank (=no ADAMTS5). All dilutions were prepared in sample buffer (PBS+0.1% BSA+0.02% $NaN_3$). To test for interference of Aggrecan, recombinant Aggrecan G1-IGD-G2 was added to this pre-incubation in selected experiments, at a concentration of 2 nM (=over 100× its $K_D$ for polypeptide 949, see below).

Subsequently, the pre-incubated mixtures (ADAMTS5 DRC+20 pM polypeptide 949±Aggrecan G1-IGD-G2) were injected via KinExA's auto-sampler over a column packed with human ADAMTS5-conjugated polymethylmethacrylate (PMMA) beads, to capture free Nanobody constructs on the beads. Captured Nanobody constructs were detected using an Alexa Fluor (AF) 647-labeled anti-Nanobody tool recognizing polypeptide 949. Percent free Nanobody construct was plotted as a function of ADAMTS5 concentration and fitted using the KinExA Pro Software v3.6.5 to determine the $K_D$.

The results, presented in Table 5.1, show that the affinity of polypeptide 949 towards human ADAMTS5 is 32.69 pM in absence of G1-IGD-G2 and 26.56 pM in presence of Aggrecan. Based on the overlap of the CI's on the $K_D$ values, the presence of Aggrecan does not interfere with the affinity of polypeptide 949 towards ADAMTS5. Affinities towards cynomolgus and rat ADAMTS5 were 24.35 pM and 25.17 pM, respectively, demonstrating binding cross-reactivity of polypeptide 949 towards both species as both $K_D$ values fall within the CI of the human $K_D$.

TABLE 5.1

Affinity of polypeptide 949 towards human ADAMTS5 in absence or presence of Aggrecan G1-IGD-G2, and towards cynomolgus and rat ADAMTS5

| | N | Average $K_D$ (pM) | 95% CI on $K_D$ (pM) |
|---|---|---|---|
| Human − Aggrecan | 3 | 32.69 | 16.35-65.38 |
| Human + Aggrecan | 3 | 26.56 | 16.38-58.46 |

TABLE 5.1-continued

Affinity of polypeptide 949 towards human ADAMTS5
in absence or presence of Aggrecan G1-IGD-G2,
and towards cynomolgus and rat ADAMTS5

|  | N | Average $K_D$ (pM) | 95% CI on $K_D$ (pM) |
|---|---|---|---|
| Cynomolgus | 1 | 24.35 | 9.25-66.27 |
| Rat | 1 | 25.17 | |

5.2 Functional Inhibition of Human, Cynomolgus and Rat ADAMTS5 by Polypeptide 949

Functional inhibition of human, cynomolgus and rat ADAMTS5 by C010100949 was studied using a FRET-based kinetic assay. This assay was performed using a FRET assay buffer (50 mM HEPES pH 7.5, 100 mM NaCl, 5 mM CaCl2*2H$_2$O, 5% glycerol, 0.1% CHAPS in MilliQ). A fixed concentration of 10 nM (final concentration) of the respective species ADAMTS5 was mixed and equilibrated with an 11-point (12$^{th}$=blank) 1/1.7 serially diluted DRC of polypeptide 949 starting at 50 nM (final concentration). Next, 30 µM (final concentration) of species-specific fluorogenic ADAMTS5 substrate was added. This substrate, an Aggrecan peptide labeled with a quencher (2,4-dinitrophenyl, Dnp) and a fluorochrome (aminobenzoic acid, Abz), was enzymatically cleaved by ADAMTS5 and the resulting fluorescence (excitation wavelength 340 nm/emission wavelength 430 nm) was kinetically measured every minute for 2 hours using a Tecan F200 microplate reader. The obtained progress curves (fluorescent signal in function of reaction time) were analyzed using GraphPad Prism software, by fitting the linear portion of each progress curve with a straight line (Y=slope*X+Y-intercept). The resulting slopes or reaction velocities ($v_i$) were normalized against the average slope of all blank samples (uninhibited reaction velocity, $v_0$), plotted as a function of the polypeptide 949 concentration and fitted with an asymmetric 5-parameter logistics (5PL) curve fit to obtain inhibition curves.

The results are summarized in FIG. 1, which is a representative graphical illustration of the results. The results show dose-dependent and complete inhibition of the enzymatic activity of ADAMTS5 from all tested species by polypeptide 949 ("C010100949"), demonstrating that they are all fully functionally inhibited by the Nanobody construct.

5.3 Affinity of Polypeptide 949 Towards Human, Cynomolgus and Rat MMP13

Functional activities as well as the enzyme inhibition constants ($K_i$) of polypeptide 949 towards MMP13 from different species were studied using a FRET-based kinetic assay. All dilutions were made in assay buffer (50 mM Tris (pH 7.5), 100 mM NaCl, 10 mM CaCl$_2$*2H$_2$O, 0.01% Tween20). A ⅓ serially diluted 11-point (12$^{th}$=blank) DRC of polypeptide 949 starting at 9 µM (final concentration) was equilibrated with a constant concentration of 0.2 nM species catalytic domain (cd) MMP-13 or to 0.2 to 20 nM activated pro-MMP13 (nominal concentration) of each species. Next, a constant concentration of 22 µM (final concentration) fluorogenic MMP substrate was added to all wells. This collagen-based substrate contains the generic MMP cleavage sequence Proline-Leucine-Glycine-Leucine (PLGL) and is labelled with a fluorochrome, Mca, and a quencher, Dpa. Active enzyme (not bound by the Nanobody construct) is able to cleave the substrate, leading to the release of the fluorochrome and resulting in a fluorescent signal (excitation wavelength 320 nm/emission wavelength 405 nm), while neutralized (Nanobody construct-bound) enzyme is not. Starting within one minute after addition of the substrate, fluorescence was measured kinetically every minute for a total of 120 cycles (2 hours) using a Tecan F200 plate reader.

The obtained progress curves (fluorescent signal in function of reaction time) were analyzed using GraphPad Prism software, by fitting the linear portion of each progress curve with a straight line (Y=slope*X+Y-intercept). The resulting slopes or reaction velocities ($v_i$) were normalized against the average slope of all blank samples (uninhibited reaction velocity, $v_0$), plotted as a function of polypeptide 949 concentration and fitted with an asymmetric 5-parameter logistics (5PL) curve fit to obtain inhibition curves.

In these assay conditions, the obtained IC$_{50}$ value equals the inhibition constant, $K_i$.

The results of the quantitative analysis are summarized in Table 5.3. Two to six independent experiments were repeated per interaction. Based on 6 independent repeated experiments, the inhibition constant of polypeptide 949 towards human cdMMP13 was determined to be 27.86 nM (95% CI: 25.67-30.23 nM). Based on 3 independently repeated experiments, the $K_i$ for activated human pro-MMP13 was determined to be 2.92 nM (95% CI: 0.61-14.02 nM). The $K_i$ values towards cynomolgus and rat MMP13 strongly corresponds to the human $K_i$'s for both catalytic domain as well as the activated pro-MMP13, indicative for cross-reactivity of polypeptide 949 for cynomolgus and rat MMP13.

TABLE 5.3

Overview of the results of the affinity determination of polypeptide 949 towards human, cynomolgus and rat MMP13 catalytic domain and activated pro-MMP13 Average $K_I$ values as well as the 95% confidence intervals (CI) were calculated via an estimation of global mean values. Cd: catalytic domain; pro: activated pro-MMP 13; CV: coefficient of variation.

|  | MMP13 form | N | Average $K_I$ (nM) | CV (%) | 95% CI on $K_I$ (nM) |
|---|---|---|---|---|---|
| Human | cd | 6 | 27.86 | 7.7 | 25.67-30.23 |
|  | pro | 3 | 2.92 | 52.7 | 0.61-14.02 |
| Cynomolgus | cd | 3 | 20.21 | 1.6 | 19.43-21.03 |
|  | pro | 2 | 3.72 | 5.5 | 2.27-6.11 |
| Rat | cd | 3 | 26.59 | 9.2 | 21.19-33.36 |
|  | pro | 2 | 13.02 | 31.9 | 0.70-241.59 |

Functional inhibition of human, cynomolgus and rat cdMMP13 as well as activated pro-MMP13 by polypeptide 949 was evaluated simultaneously in the experiments that were performed to measure the $K_I$ (see above). FIG. 2 is a representative graphical illustration of the results. These results demonstrate dose-dependent and complete functional inhibition of the enzymatic activity of all tested species cdMMP13 and pro-MMP13 forms by the Nanobody construct 949.

5.4 Affinity of Polypeptide 949 Towards Human, Cynomolgus and Rat Aggrecan G1-IGD-G2

Affinity determination of polypeptide 949 towards human, cynomolgus monkey and rat recombinant Aggrecan G1-IGD-G2 was performed using surface plasmon resonance (SPR) on a ProteOn XPR36 interaction array instrument (BioRad, serial n° 670BR6176). In brief, recombinant Aggrecan G1-IGD-G2 ('ligand') was immobilized to the ligand lanes of a GLC sensor chip (Biorad cat #176-5011) by amine coupling at a concentration of 10 μg/mL in 10 mM acetate pH 4.5 and a flow rate of 100 μL/min, aiming for an immobilization level of 400 resonance units (RU). Polypeptide 949 ("C010100949"; 'analyte') was injected along the analyte lanes of the sensor chip under a continuous flow of 45 μL/min for 2 minutes at various concentrations (0.5-1-2-4-6-10 nM) in 1× HBS-P+pH 7.4 as running buffer (GE Healthcare cat #R-1006-71). Dissociation time was 10 min. After each sample injection the surfaces were regenerated with 10 mM glycine pH 1.5. Interaction between the Aggrecan G1-IGD-G2 and polypeptide 949 was detected as increases in refractory index which occur as a result of mass changes on the chip due to binding of the polypeptide 949 to the Aggrecan. This change in refractive index causes a change in the intensity and angle of reflected light which is quantitatively measured in real-time and plotted as response units (RU) versus time on a sensorgram. The kinetic constants were calculated from the obtained sensorgrams using ProteOn Manager 3.1.0 version 3.1.0.6 software and the 'kinetic Langmuir $k_a/k_d$ simultaneous' model.

The results are summarized in Table 5.4. Based on 2 to 4 independently repeated experiments the mean binding affinities ($K_D$) of polypeptide 949 towards captured Aggrecan G1-IGD-G2 were determined to be 14.0 pM, 16.0 pM and 16.6 pM for human, cynomolgus and rat, respectively.

Since the mode of action (MoA) of the CAP building blocks of polypeptide 949 relies solely on Aggrecan binding, which is directly reflected by the SPR-based affinity determination, further functional analyses of the CAP building blocks are not relevant. From these SPR data it can be concluded that the polypeptide 949 demonstrates full cross-reactivity towards both cynomolgus and rat Aggrecan with no affinity difference compared to human.

TABLE 5.4

Overview of the results of the affinity determination of 949 towards human, cynomolgus and rat Aggrecan G1-IGD-G2. Average $K_D$ values as well as the 95% confidence intervals (CI) were calculated via an estimation of global mean values. N: number of independent experiments; $K_D$: dissociation constant; NC: not calculated. (*) For cynomolgus, 2 independent experiments both yielded the same result of 16.0 pM, hence no CI could be calculated as no standard error information on the $K_D$ is provided by the ProteOn software.

|  | N | Average $K_D$ (pM) | 95% CI on $K_D$ (pM) |
|---|---|---|---|
| Human | 4 | 14.0 | 5.9-33.7 |
| Cynomolgus | 2 | 16.0 | NC (*) |
| Rat | 3 | 16.6 | 7.0-39.5 |

Example 6 Inhibition of Ex Vivo Cartilage Degradation in a Bovine Explant Model

Polypeptide 949 (M-A-C-C: 62C02-2F03-114F08-114F08) was tested in bovine cartilage explant assays for inhibition of cartilage degradation.

In short, the polypeptide was incubated with bovine cartilage explants that were cultured 5 days with IL-1α to induce an OA-like cartilage degradation process. Within 5 days, degradation of primarily Aggrecan ensues, whereas Collagen degradation only occurs after about two weeks, i.e., after termination of the experiments described here. At the end of the experiment, the GAG (mainly derived from Aggrecan) which was released from the degrading cartilage into the culture supernatant was quantified. The efficacy of inhibition of GAG release by the polypeptide was calculated as compared to a reference small molecule inhibitor, which under these conditions fully inhibited the IL-1α stimulated GAG release.

The results are depicted in FIG. 3.

It can be seen that polypeptide 949 (NB949 in the figure) fully inhibits bovine cartilage degradation in a dose-dependent manner.

Example 7 Inhibition of Ex Vivo Cartilage Degradation in a Human Explant Model

Polypeptide 949 (M-A-C-C: 62CO2-2F03-114F08-114F08) was tested in human cartilage explant assays for inhibition of cartilage degradation. Briefly, the polypeptide was incubated with human cartilage explants that were cultured 7 days with IL-1β+Oncostatin M (OSM). Within 7 days, degradation of primarily Aggrecan ensues, whereas Collagen degradation only occurs after about two weeks, i.e., after termination of the experiments described here. At the end of the experiment, the GAG (mainly derived from Aggrecan) which was released from the degrading cartilage into the culture supernatant was quantified. The IC50 was calculated on the basis of the negative control level (=GAG release from explants without additional stimulus) and the IL-1β+OSM level, as measure for maximal GAG loss. GAG is shown as GAG release (in μg) per mg cartilage of each individual explant.

The results are depicted in FIG. 4.

The data show, that the Nanobody construct inhibits GAG release from human OA cartilage in a dose-dependent manner with a calculated $IC_{50}$ of 0.03724 μM.

Example 8 CAP Extends Ex Vivo the Efficacy of Polypeptides Inhibiting Cartilage Degradation In order to evaluate the effect of the CAP moiety, which functions to anchor the polypeptide to the cartilage, the bovine explant assay described above was modified to include wash steps following the incubation step (1 h) of the cartilage explant with the polypeptides (see FIG. 5, top panel). Following the wash steps, cartilage degradation was initiated by adding IL-1α. After 7 days of additional incubation, GAG release into the culture supernatant was quantified. As a control, the ADAMTS5 inhibiting polypeptide 581 was included, which does not contain a CAP-binding moiety (SEQ ID NO: 65).

The results are shown in FIG. 5.

The experiment shows that the control polypeptide 581, i.e. the polypeptide not containing a CAP-binding moiety, showed almost no efficacy in inhibiting ADAMTS5. This is in vast contrast to assays in which the wash steps were omitted. On the other hand, polypeptide 949 remained efficacious, even after extensive washing. Given that the GAG release is driven by ADAMTS5, rather than MMP13 under the present assay conditions, this result is a strong indication that the CAP-binding moiety indeed functions to anchor the polypeptides to the cartilage, and that the CAP-binding moiety does not affect the efficacy of the ADAMTS5 ISVD.

Example 9 Effect of Polypeptide 949 in a Bovine Cartilage Synovium Co-Culture System Knowing that OA does not only involve cartilage, polypeptide 949 was also tested in a bovine model comprised of synovial membrane (synovium) and explants from articular cartilage. Briefly, cartilage explants and synovium in a ratio 1/1 were co-cultured for 28 days with regular medium change. On a weekly basis, C2M (Col II degradation) and C3M (Col III degradation) were determined in the supernatant of the co-cultures.

Results (as AUC=area under the curve) are depicted in FIG. 6.

The data show, that co-incubation of cartilage explants with synovium induces release of C2M (left graph) and C3M (right graph). The polypeptide 949 was incubated in 3 different concentrations (1 nM, 10 nM, 100 nM). The effect of the polypetide 949 was evaluated in comparison to the reference molecule Wyeth (MSC2310852A-1). The data show that the exemplary polypeptide 949 as well as the reference compound strongly inhibit C2M and C3M release.

Example 10 Cartilage Retention Studies

In order to determine the retention of the Nanobody constructs in vivo, a rat cartilage retention study was designed using the exemplary polypeptide 949. Since polypeptide 949 has 4 building blocks, (M-A-C-C) it is assumed that the polypeptides 754 and 954, each with two Aggrecan binders and one target specific ISVD, behave essentially similarly.

An ELISA-based ligand binding assay was developed to quantify the local Nanobody construct concentrations in rat cartilage while a ligand binding assay (MSD platform) was developed to quantify the Nanobody construct in circulation.

The results are shown in FIG. 7.

In conclusion, the exemplary polypeptide 949 is retained in cartilage in vivo up to 112 days after IA administration while systemic concentrations (low µg/ml range) were only detectable at the first sampling time point (2 hours post IA injection) in healthy rats while no polypeptide could be detected at later time points (14 days and beyond).

Hence, constructs comprising anti-Aggrecan ISVDs 114F08 are stable and retained in in vivo models.

Example 11 Rat In Vivo MMT DMOAD Study 1

In order to demonstrate the in vivo efficacy of polypeptide 754 (M-C-C; "Nanobody 754"), polypeptide 954 (A-C-C; "Nanobody 954") and polypeptide 949 (M-A-C-C, "Nanobody 949") a surgically induced Medial Meniscal Tear (MMT) model in rats was used. In short, rats were operated in one knee to induce OA-like symptoms. Treatment started 3 days post-surgery by a single IA injection. The following doses were administered 3 days post-surgery to the animals: vehicle (buffer), polypeptide 754 (300 µg/rat), polypeptide 949 (4, 40 or 400 µg/rat) and polypeptide 954 (300 µg/rat).

Histopathology was performed at day 42 post surgery. The medial tibial cartilage degeneration width and medial tibial total cartilage degeneration width were determined, as well as the percentage reduction of cartilage degeneration. Per group, 20 animals were used.

The results of the medial tibial cartilage degeneration width are shown in FIG. 8.

The results demonstrate that the medial tibial cartilage width was substantially reduced by all Nanobody constructs after 42 days compared to the vehicle. These results further suggest that (a) the CAP-moiety has no negative impact on the activity of the constructs;
(b) the CAP-moiety enables the retention of the constructs;
(c) all constructs have a positive effect on the cartilage width; and
(d) the combination of an ADAMTS5 inhibitor and an MMP13 inhibitor demonstrates the largest effect overall as exemplified by polypeptide 949.

Example 12 Confirmatory Rat In Vivo MMT DMOAD Study 2

The in vivo efficacy studies described in Example 11 (DMOAD study 1) were essentially repeated with a different dosing regimen. Furthermore, in the DMOAD study 1, only mild OA was present 3 days post surgery. Therefore, the polypeptides were now evaluated at a more advanced stage of OA in the MMT model, while treatment was started 7 days post-surgery. In short, the medial tibial cartilage degeneration width in µm was measured at day 42 post surgery. Again, polypeptide 949 was used to exemplify the combined effect of ADAMTS5 and MMP13 inhibitors.

In a first series of experiments, consisting of 20 animals per group, each group received a single IA injection (400 µg, 800 µg, vehicle) 7 days post-surgery. At the end of the treatment, the group receiving 400 µg of polypeptide 949 showed a 21% decrease in medial tibial cartilage degeneration width, while the 800 µg group showed a 16% decrease (see FIG. 9). These results confirm the efficacy of the constructs.

In a second series of experiments, again consisting of 20 animals per group, each group received two IA injections at day 7 and day 10 post-surgery (200 µg, 400 µg, 800 µg, vehicle). At the end of the treatment, the group receiving 200 µg of polypeptide 949 showed a 14% decrease in tibial width, the 800 µg group showed a 31% decrease, while the 400 µg group showed a 35% decrease (FIG. 9).

Example 13 Symptomatic Benefit In Vivo

In order to evaluate the ability of the polypeptides to provide a symptomatic benefit, a rat surgical OA model was used. In short, rats were subjected to ACLt and tMx surgery to induce OA at day 0. In the ACLt and tMx surgical model (anterior cruciate ligament transection extended with a medial meniscectomy) constructs were administered IA in week 1 and week 8 at different concentrations (100 µg, 400 µg and 1000 µg). One group of rats was treated IA with Tanezumab (Pfizer), an anti-nerve growth factor (NGF) mAb, which was included as positive control for symptom alleviation in the study. In weeks 2, 5, 9 and 13, the symptomatic benefit via gait analysis (on a CatWalk) as well as decrease in joint diameter were determined.

The results are shown in FIG. 10.

Intra-articular treatment with the polypeptides resulted in a symptomatic benefit up to 43%.

Example 14 Retention of CAP Binders in Healthy and Osteoarthritic Rats is Similar In Vivo It was demonstrated in Example 10 in a cartilage retention study in healthy rats that the polypeptides of the invention were measurable in cartilage up to 112 days after intra-articular (I.A.) injection. Since the cartilage composition can have an influence on cartilage binding and absorption in systemic circulation, the pharmacokinetics of the polypeptides of the invention were compared in diseased osteoarthritis and healthy rats in vivo by following the serum level of the polypeptides in time.

In particular, the surgically induced Medial Meniscal Tear (MMT) model in rats was used as described in Example 10, but with some modifications. In short, the polypeptides of the invention were coupled to an anti-MMP13 ISV and an anti-ADAMTS5 ISV (designated as "949", "0949" or "C010100949" Nanobodies). Rats were operated in one knee to induce OA-like symptoms (OA-group). Each treatment group (healthy and OA) comprised of 15 animals, and received a single I.A. injection of 400 µg/30 µl Nanobody at day 7 (healthy) or 7 days post-surgery (MMT). Serum samples were collected from anesthetized rats at day 0, at day 7 (at 0 h=pre-dose sample) at day 8 (at different times post treatment up to 24 h), day 9 (48 h post-treatment), d10 (3 days post-treatment), d14 (7 days post-treatment), d21 (14 days post-treatment) and d42 (35 days post-treatment). Collected serum samples were used for the determination of the polypeptide concentrations in an electrochemoluminescence (ECL) based total PK assay format, followed by a non-compartmental analysis.

The retention of the polypeptides in the serum of healthy and OA rats is shown in FIG. 11.

The results demonstrate that no obvious differences can be seen in the serum concentrations of the polypeptides in healthy rats and OA rats. Hence, these results support that cartilage degradation has no influence on the pharmacokinetics of the polypeptides of the invention.

TABLE A-1

Name and short description ("ID"), SEQ ID NO: s ("SEQ") and amino acid sequences of polypeptides of the invention

| ID | SEQ | Sequence |
|---|---|---|
| ALX-1011 949 | 1 | EVQLVESGGGVVQPGGSLRLSCAASGFAFSAAYMSWVRQAPGKGLEWVSSISDDGSKTYYADSVKGRFTISRDNSKNTVYLQMNSLRPEDTALYYCNTGYGATTTRPGRYWGQGTLVTVSSGGGGSGGGGSGGGGSGGGGSGGGGSGGGGSGGGGSEVQLVESGGGVVQPGGSLRLSCAASGRTVSSYAMGWFRQAPGKEREFVAGISRSAERTYYVDSLKGRFTISRDNSKNTVYLQMNSLRPEDTALYYCAADLDPNRIFSREEYAYWGQGTLVTVSSGGGGSGGGGSGGGGSGGGGSGGGGSGGGGSGGGGSEVQLVESGGGVVQPGGSLRLSCAASGSTFIINVVRWYRRAPGKQRELVATISSGGNANYVDSVRGRFTISRDNSKNTVYLQMNSLRPEDTALYYCNVPTTHYGGVYYGPYWGQGTLVTVSSGGGGSGGGGSGGGGSGGGGSGGGGSGGGGSGGGGSEVQLVESGGGVVQPGGSLRLSCAASGSTFIINVVRWYRRAPGKQRELVATISSGGNANYVDSVRGRFTISRDNSKNTVYLQMNSLRPEDTALYYCNVPTTHYGGVYYGPYWGQGTLVTVSSA |
| 62C02 MMP13 | 2 | EVQLVESGGGVVQPGGSLRLSCAASGFAFSAAYMSWVRQAPGKGLEWVSSISDDGSKTYYADSVKGRFTISRDNSKNTVYLQMNSLRPEDTALYYCNTGYGATTTRPGRYWGQGTLVTVSS |
| 2F03 ATS5 | 3 | EVQLVESGGGVVQPGGSLRLSCAASGRTVSSYAMGWFRQAPGKEREFVAGISRSAERTYYVDSLKGRFTISRDNSKNTVYLQMNSLRPEDTALYYCAADLDPNRIFSREEYAYWGQGTLVTVSS |
| 114F08 CAP | 4 | EVQLVESGGGVVQPGGSLRLSCAASGSTFIINVVRWYRRAPGKQRELVATISSGGNANYVDSVRGRFTISRDNSKNTVYLQMNSLRPEDTALYYCNVPTTHYGGVYYGPYWGQGTLVTVSS |
| MCC 754 | 5 | EVQLVESGGGVVQPGGSLRLSCAASGFAFSAAYMSWVRQAPGKGLEWVSSISDDGSKTYYADSVKGRFTISRDNSKNTVYLQMNSLRPEDTALYYCNTGYGATTTRPGRYWGQGTLVTVSSGGGGSGGGGSGGGGSGGGGSGGGGSGGGGSGGGGSEVQLVESGGGVVQPGGSLRLSCAASGSTFIINVVRWYRRAPGKQRELVATISSGGNANYVDSVRGRFTISRDNSKNTVYLQMNSLRPEDTALYYCNVPTTHYGGVYYGPYWGQGTLVTVSSGGGGSGGGGSGGGGSGGGGSGGGGSGGGGSGGGGSEVQLVESGGGVVQPGGSLRLSCAASGSTFIINVVRWYRRAPGKQRELVATISSGGNANYVDSVRGRFTISRDNSKNTVYLQMNSLRPEDTALYYCNVPTTHYGGVYYGPYWGQGTLVTVSSA |
| ACC 954 | 6 | EVQLVESGGGVVQPGGSLRLSCAASGRTVSSYAMGWFRQAPGKEREFVAGISRSAERTYYVDSLKGRFTISRDNSKNTVYLQMNSLRPEDTALYYCAADLDPNRIFSREEYAYWGQGTLVTVSSGGGGSGGGGSGGGGSGGGGSEVQLVESGGGVVQPGGSLRLSCAASGSTFIINVVRWYRRAPGKQRELVATISSGGNANYVDSVRGRFTISRDNSKNTVYLQMNSLRPEDTALYYCNVPTTHYGGVYYGPYWGQGTLVTVSSGGGGSGGGGSGGGGSGGGGSGGGGSGGGGSGGGGSEVQLVESGGGVVQPGGSLRLSCAASGSTFIINVVRWYRRAPGKQRELVATISSGGNANYVDSVRGRFTISRDNSKNTVYLQMNSLRPEDTALYYCNVPTTHYGGVYYGPYWGQGTLVTVSSA |
| 114F08-Alb "054" | 41 | EVQLVESGGGLVQAGGSLRLSCAASGSTFIINVVRWYRRTPGKQRELVATISSGGNANYVDSVRGRFSISRDGAKNAVDLQMNGLKPEDTAVYYCNVPTTHYGGVYYGPYWGQGTLVTVSSGGGGSGGGGSGGGGSGGGGSGGGGSEVQLVESGGGLVQPGNSLRLSCAASGFTFSSAVMSWVRQAPGKGLEWVSSISGSGSDTLYADSVKGRFTISRDNAKTTLYLQMNSLRPEDTAVYYCTIGGSLSRSSQGTLVTVSS |
| Alb-114F08-114F08 "118" | 42 | EVQLVESGGGLVQPGNSLRLSCAASGFTFSSAVMSWVRQAPGKGLEWVSSISGSGSDTLYADSVKGRFTISRDNAKTTLYLQMNSLRPEDTAVYYCTIGGSLSRSSQGTLVTVSSGGGGSGGGGSEVQLVESGGGLVQAGGSLRLSCAASGSTFIINVVRWYRRTPGKQRELVATISSGGNANYVDSVRGRFSISRDGAKNAVDLQMNGLKPEDTAVYYCNVPTTHYGGVYYGPYWGQGTLVTVSSGGGGSGGGGSGGGGSGGGGSGGGGSGGGGSEVQLVESGGGLVQAGGSLRLSCAASGSTFIINVVRWYRRTPGKQRELVATISSGGNANYVDSVRGRFSISRDGAKNAVDLQMNGLKPEDTAVYYCNVPTTHYGGVYYGPYWGQGTLVTVSS |
| Alb-Alb "030" | 43 | EVQLVESGGGLVQPGNSLRLSCAASGFTFSSAVMSWVRQAPGKGLEWVSSISGSGSDTLYADSVKGRFTISRDNAKTTLYLQMNSLRPEDTAVYYCTIGGSLSRSSQGTLVTVSSGGGGSGGGGSGGGGSGGGGSGGGGSGGGGSEVQLVESGGGLVQPGNSLRLSCAASGFTFSSAVMSWVRQAPGKGLEWVSSISGSGSDTLYADSVKGRFTISRDNAKTTLYLQMNSLRPEDTAVYYCTIGGSLSRSSQGTLVTVSS |

TABLE A-1-continued

Name and short description ("ID"), SEQ ID NO: s ("SEQ") and amino acid sequences of polypeptides of the invention

| ID | SEQ | Sequence |
|---|---|---|
| 949-9GS "973" | 62 | EVQLVESGGGVVQPGGSLRLSCAASGFAFSAAYMSWVRQAPGKGLEWVSSISDDGSKTYYADSVKGRFTI SRDNSKNTVYLQMNSLRPEDTALYYCNTGYGATTTRPGRYWGQGTLVTVSSGGGGSGGGSEVQLVESGGG VVQPGGSLRLSCAASGRTVSSYAMGWFRQAPGKEREFVAGISRSAERTYYVDSLKGRFTISRDNSKNTVY LQMNSLRPEDTALYYCAADLDPNRIFSREEYAYWGQGTLVTVSSGGGGSGGGSEVQLVESGGGVVQPGGS LRLSCAASGSTFIINVVRWYRRAPGKQRELVATISSGGNANYVDSVRGRFTISRDNSKNTVYLQMNSLRP EDTALYYCNVPTTHYGGVYYGPYWGQGTLVTVSSGGGGSGGGSEVQLVESGGGVVQPGGSLRLSCAASGS TFIINVVRWYRRAPGKQRELVATISSGGNANYVDSVRGRFTISRDNSKNTVYLQMNSLRPEDTALYYCNV PTTHYGGVYYGPYWGQGTLVTVSSA |
| 754-9GS | 63 | EVQLVESGGGVVQPGGSLRLSCAASGFAFSAAYMSWVRQAPGKGLEWVSSISDDGSKTYYADSVKGRFTI SRDNSKNTVYLQMNSLRPEDTALYYCNTGYGATTTRPGRYWGQGTLVTVSSGGGGSGGGSEVQLVESGGG VVQPGGSLRLSCAASGSTFIINVVRWYRRAPGKQRELVATISSGGNANYVDSVRGRFTISRDNSKNTVYL QMNSLRPEDTALYYCNVPTTHYGGVYYGPYWGQGTLVTVSSGGGGSGGGSEVQLVESGGGVVQPGGSLRL SCAASGSTFIINVVRWYRRAPGKQRELVATISSGGNANYVDSVRGRFTISRDNSKNTVYLQMNSLRPEDT ALYYCNVPTTHYGGVYYGPYWGQGTLVTVSSA |
| 954-9GS | 64 | EVQLVESGGGVVQPGGSLRLSCAASGRTVSSYAMGWFRQAPGKEREFVAGISRSAERTYYVDSLKGRFTI SRDNSKNTVYLQMNSLRPEDTALYYCAADLDPNRIFSREEYAYWGQGTLVTVSSGGGGSGGGSEVQLVES GGGVVQPGGSLRLSCAASGSTFIINVVRWYRRAPGKQRELVATISSGGNANYVDSVRGRFTISRDNSKNT VYLQMNSLRPEDTALYYCNVPTTHYGGVYYGPYWGQGTLVTVSSGGGGSGGGSEVQLVESGGGVVQPGGS LRLSCAASGSTFIINVVRWYRRAPGKQRELVATISSGGNANYVDSVRGRFTISRDNSKNTVYLQMNSLRP EDTALYYCNVPTTHYGGVYYGPYWGQGTLVTVSSA |
| pp 581 | 65 | DVQLVESGGGVVQPGGSLRLSCAASGRTVSSYAMGWFRQAPGKEREFVAGISRSAERTYYVDSLKGRFTI SRDNSKNTVYLQMNSLRPEDTALYYCAADLDPNRIFSREEYAYWGQGTLVTVSSGGGGSGGGSGGGGSG GGGSGGGGSGGGGSEVQLVESGGGVVQPGNSLRLSCAASGFTFSSFGMSWVRQAPGKGLEWVSSI SGSGSDTLYADSVKGRFTISRDNAKTTLYLQMNSLRPEDTALYYCTIGGSLSRSSQGTLVTVSSA |

TABLE B

Miscellaneous Amino acid sequences: Name and short description ("ID"), SEQ ID NO: s ("SEQ") and amino acid sequences ("sequences")

| ID | SEQ | Sequence |
|---|---|---|
| human MMP13 | 66 | MHPGVLAAFLFLSWTHCRALPLPSGGDEDDLSEEDLQFAERYLRSYYHPTNLAGILKENAASSMTERLRE MQSFFGLEVTGKLDDNTLDVMKKPRCGVPDVGEYNVFPRTLKWSKMNLTYRIVNYTPDMTHSEVEKAFKK AFKVWSDVTPLNFTRLHDGIADIMISFGIKEHGDFYPFDGPSGLLAHAFPPGPNYGGDAHFDDDETWTSS SKGYNLFLVAAHEFGHSLGLDHSKDPGALMFPIYTYTGKSHFMLPDDDVQGIQSLYGPGDEDPNPKHPKT PDKCDPSLSLDAITSLRGETMIFKDRFFWRLHPQQVDAELFLTKSFWPELPNRIDAAYEHPSHDLIFIFR GRKFWALNGYDILEGYPKKISELGLPKEVKKISAAVHFEDTGKTLLFSGNQVWRYDDTNHIMDKDYPRLI EEDFPGIGDKVDAVYEKNGYIYFFNGPIQFEYSIWSNRIVRVMPANSILWC |
| human ADAMTS5 | 67 | MLLGWASLLLCAFRLPLAAVGPAATPAQDKAGQPPTAAAAAQPRRRQGEEVQERAEPPGHPHPLAQRRRS KGLVQNIDQLYSGGGKVGYLVYAGGRRFLLDLERDGSVGIAGFVPAGGGTSAPWRHRSHCFYRGTVDGSP RSLAVFDLCGGLDGFFAVKHARYTLKPLLRGPWAEEEKGRVYGDGSARILHVYTREGFSFEALPPRASCE TPASTPEAHEHAPAHSNPSGRAALASQLLDQSALSPAGGSGPQTWWRRRRRSISRARQVELLLVADASMA RLYGRGLQHYLLTLASIANRLYSHASIENHIRLAVVKVVVLGDKDKSLEVSKNAATTLKNFCKWQHQHNQ LGDDHEEHYDAAILFTREDLCGHHSCDTLGMADVGTICSPERSCAVIEDDGLHAAFTVAHEIGHLLGLSH DDSKFCEETFGSTEDKRLMSSILTSIDASKPWSKCTSATITEFLDDGHGNCLLDLPRKQILGPEELPGQT YDATQQCNLTFGPEYSVCPGMDVCARLWCAVVRQGQMVCLTKKLPAVEGTPCGKGRICLQGKCVDKIKKK YYSTSSHGNWGSWGSWGQCSRSCGGGVQFAYRHCNNPAPRNNGRYCTGKRAIYRSCSLMPCPPNGKSFRH EQCEAKNGYQSDAKGVKTFVEWVPKYAGVLPADVCKLTCRAKGTGYYVVFSPKVTDGTECRLYSNSVCVR GKCVRTGCDGIIGSKLQYDKCGVCGGDNSSCTKIVGTFNKKSKGYTDVVRIPEGATHIKVRQFKAKDQTR FTAYLALKKKNGEYLINGKYMISTSETIIDINGTVMNYSGWSHRDDFLHGMGYSATKEILIVQILATDPT KPLDVRYSFFVPKKSTPKVNSVTSHGSNKVGSHTSQPQWVTGPWLACSRTCDTGWHTRTVQCQDGNRKLA KGCPLSQRPSAFKQCLLKKC |
| human Aggrecan | 68 | MTTLLWVFVTLRVITAAVTVETSDHDNSLSVSIPQPSPLRVLLGTSLTIPCYFIDPMHPVTTAPSTAPLA PRIKWSRVSKEKEVVLLVATEGRVRVNSAYQDKVSLPNYPAIPSDATLEVQSLRSNDSGVYRCEVMHGIE DSEATLEVVKGIVFHYRAISTRYTLDFDRAQRACLQNSAIIATPEQLQAAYEDGFHQCDAGWLADQTVR YPIHTPREGCYGDKDEFPGVRTYGTRDTNETYDVYCFAEEMEGEVFYATSPEKFTFQEAANECRRLGARL ATTGHVYLAWQAGMDMCSAGWLADRSVRYPISKARPNCGGNLLGVRTVYHANQTGYPDPSSRYDAICYT GEDFVDIPENFFGVGGEEDITVQTVTWPDMELPLPRNITEGEARGSVILTVKPIFEVSPSPLEPEEPFTF APEIGATAFAEVENETGEATRPWGFPTPGLGPATAFTSEDLVVQVTAVPGQPHLPGGVVFHYRPGPTRYS LTFEEAQQACPGTGVAIASPEQLQAAYEAGYEQCDAGWLRDQTVRYPIVSPRTPCVGDKDSSPGVRTYGV RPSTETYDVYCFVDRLEGEVFFATRLEQFTFQEALEFCESHNATATTGQLYAAWSRGLDKCYAGWLADGS LRYPIVTPRPACGGDKPGVRTVELYPNQTGLPDPLSRHHAFCFRGISAVPSPGEEEGGTPTSPSGVEEWI VTQVVPGVAAVPVEEETTAVPSGETTAILEFTTEPENQTEWEPAYTPVGTSPLPGILPTWPPTGAETEES TEGPSATEVPSASEEPSPSEVPFPSEEPSPSEEPFPSVRPFPSVELFPSEEPFPSKEPSPSEEPSASEEP YTPSPPEPSWTELPSSGEESGAPDVSGDFTGSGDVSGHLDFSGQLSGDRASGLPSGDLDSSGLTSTVGSG LTVESGLPSGDEERIEWPSTPTVGELPSGAEILEGSASGVGDLSGLPSGEVLETSASGVGDLSGLPSGEV |

TABLE B-continued

Miscellaneous Amino acid sequences: Name and short description ("ID"), SEQ ID NO: s ("SEQ") and amino acid sequences ("sequences")

| ID | SEQ | Sequence |
|---|---|---|
| | | LETTAPGVEDISGLPSGEVLETTAPGVEDISGLPSGEVLETTAPGVEDISGLPSGEVLETTAPGVEDISG |
| | | LPSGEVLETTAPGVEDISGLPSGEVLETAAPGVEDISGLPSGEVLETAAPGVEDISGLPSGEVLETAAPG |
| | | VEDISGLPSGEVLETAAPGVEDISGLPSGEVLETAAPGVEDISGLPSGEVLETAAPGVEDISGLPSGEVL |
| | | ETAAPGVEDISGLPSGEVLETAAPGVEDISGLPSGEVLETAAPGVEDISGLPSGEVLETAAPGVEDISGL |
| | | PSGEVLETAAPGVEDISGLPSGEVLETTAPGVEEISGLPSGEVLETTAPGVEEISGLPSGEVLETTAPGV |
| | | EEISGLPSGEVLETSTSAVGDLSGLPSGGEVLEISVSGVEDISGLPSGEVVETSASGIEDVSELPSGEGL |
| | | ETSASGVEDLSRLPSGEEVLEISASGFGDLSGVPSGGEGLETSASEVGTDLSGLPSGREGLETSASGAED |
| | | LSGLPSGKEDLVGSASGDLDLGKLPSGTLGSSGQAPETSGLPSGFGEYSGVDLGSGPPSGLPDFSGLPSG |
| | | FPTVSLVDSTLVEVVTASTASELEGRGTIGISGAGEISGLPSSELDISGRASGLPSGTELSGQASGSPDV |
| | | SGEIPGLFGVSGQPSGFPDTSGETSGVTELSGLSSGQPGVSGEASGVLYGTSQPFGITDLSGETSGVPDL |
| | | SGQPSGLPGFSGATSGVPDLVSGTTSGSGESSGITFVDTSLVEVAPTTFKEEEGLGSVELSGLPSGEADL |
| | | SGKSGMVDVSGQFSGTVDSSGFTSQTPEFSGLPSGIAEVSGESSRAEIGSSLPSGAYYGSGTPSSFPTVS |
| | | LVDRTLVESVTQAPTAQEAGEGPSGILELSGAHSGAPDMSGEHSGFLDLSGLQSGLIEPSGEPPGTPYFS |
| | | GDFASTTNVSGESSVAMGTSGEASGLPEVTLITSEFVEGVTEPTISQELGQRPPVTHTPQLFESSGKVST |
| | | AGDISGATPVLPGSGVEVSSVPESSSETSAYPEAGFGASAAPEASREDSGSPDLSETTSAFHEANLERSS |
| | | GLGVSGSTLTFQEGEASAAPEVSGESTTTSDVGTEAPGLPSATPTASGDRTEISGDLSGHTSQLGVVIST |
| | | SIPESEWTQQTQRPAETHLEIESSSLLYSGEETHTVETATSPTDASTPASPEWKRESESTAAAPARSCAE |
| | | EPCGAGTCKETEGHVICLCPPGYTGEHCNIDQEVCEEGWNKYQGHCYRHFPDRETWVDAERRCREQQSHL |
| | | SSIVTPEEQEFVNNNAQDYQWIGLNDRTIEGDFRWSDHPMQFENWRPNQPDNEFAAGEDCVVMIWHEKG |
| | | EWNDVPCNYHLPFTCKKGTVACGEPPVVEHARTFGQKKDRYEINSLVRYQCTEGFVQRHMPTIRCQPSGH |
| | | WEEPRITCTDATTYKRRLQKRSSRHPRRSRPSTAH |

TABLE C

Various Linker sequences ("ID" refers to the SEQ ID NO as used herein)

| Name | ID | Amino acid sequence |
|---|---|---|
| A3 | 24 | AAA |
| 5GS linker | 25 | GGGGS |
| 7GS linker | 26 | SGSGGS |
| 8GS linker | 27 | GGGGGGS |
| 9GS linker | 28 | GGGGSGGGS |
| 10GS linker | 29 | GGGGSGGGGS |
| 15GS linker | 30 | GGGGSGGGGSGGGGS |
| 18GS linker | 31 | GGGGSGGGGSGGGGGGS |
| 20GS linker | 32 | GGGGSGGGGSGGGGSGGGGS |
| 25GS linker | 33 | GGGGSGGGGSGGGGSGGGGSGGGGS |
| 30GS linker | 34 | GGGGSGGGGSGGGGSGGGGSGGGGSGGGGS |
| 35GS linker | 35 | GGGGSGGGGSGGGGSGGGGSGGGGSGGGGSGGGS |
| 40GS linker | 36 | GGGGSGGGGSGGGGSGGGGSGGGGSGGGGSGGGGSGGGGS |
| G1 hinge | 37 | EPKSCDKTHTCPPCP |
| 9GS-G1 hinge | 38 | GGGGSGGGSEPKSCDKTHTCPPCP |
| Llama upper long hinge region | 39 | EPKTPKPQPAAA |
| G3 hinge | 40 | ELKTPLGDTTHTCPRCPEPKSCDTPPPCPRCPEPKSCDTPPPCPRCPEPKSCDTPPPCPRCP |

TABLE A-2

Sequences for CDRs and frameworks, plus preferred combinations as provided in formula I, namely FR1-CDR1-FR2-CDR2-FR3-CDR3-FR4 (the following terms: "ID" refers to the given SEQ ID NO)

| ID | Nanobody | ID | FR1 | ID | CDR1 | ID | FR2 | ID | CDR2 |
|---|---|---|---|---|---|---|---|---|---|
| 2 | 62C02 MMP13 | 7 | EVQLVESGG GVVQPGGSL RLSCAAS | 8 | GFAFSAAYMS | 9 | WVRQAPGKGLEWVS | 10 | SISDDGSKTY |
| 3 | 02F03 ATS5 | 7 | EVQLVESGG GVVQPGGSL RLSCAAS | 14 | GRTVSSYAMG | 15 | WFRQAPGKEREFVA | 16 | GISRSAERTY |
| 4 | 114F08 Aggrec an-CAP | 7 | EVQLVESGG GVVQPGGSL RLSCAAS | 19 | GSTFIINVVR | 20 | WYRRAPGKQRELVA | 21 | TISSGGNAN |

TABLE A-2-continued

Sequences for CDRs and frameworks, plus preferred combinations as
provided in formula I, namely FR1-CDR1-FR2-CDR2-FR3-CDR3-FR4 (the
following terms: "ID" refers to the given SEQ ID NO)

| ID | ID FR3 | ID CDR3 | ID FR4 |
|---|---|---|---|
| 2 | 11 YADSVKGRFTISRDNSKN TVYLQMNSLRPEDTALYY CNT | 12 GYGATTTRPGRY | 13 WGQGTLVTVSS |
| 3 | 17 YVDSLKGRFTISRDNSKN TVYLQMNSLRPEDTALYY CAA | 18 DLDPNRIFSREEYAY | 13 WGQGTLVTVSS |
| 4 | 22 YVDSVRGRFTISRDNSKN TVYLQMNSLRPEDTALYY CNV | 23 PTTHYGGVYYGPY | 13 WGQGTLVTVSS |

TABLE D

Serum albumin binding ISVD sequences ("ID" refers to
the SEQ ID NO as used herein), including the CDR sequences

| Name | ID | Amino acid sequence |
|---|---|---|
| Alb8 | 44 | EVQLVESGGGLVQPGNSLRLSCAASGFTFSSFGMSWVRQAPGKGLEWVSSISGSGSDT LYADSVKGRFTISRDNAKTTLYLQMNSLRPEDTAVYYCTIGGSLSRSSQGTLVTVSS |
| Alb23 | 45 | EVQLLESGGGLVQPGGSLRLSCAASGFTFRSFGMSWVRQAPGKGPEWVSSISGSGSDT LYADSVKGRFTISRDNSKNTLYLQMNSLRPEDTAVYYCTIGGSLSRSSQGTLVTVSS |
| Alb129 | 46 | EVQLVESGGGVVQPGNSLRLSCAASGFTFSSFGMSWVRQAPGKGLEWVSSISGSGSDT LYADSVKGRFTISRDNAKTTLYLQMNSLRPEDTATYYCTIGGSLSRSSQGTLVTVSSA |
| Alb132 | 47 | EVQLVESGGGVVQPGGSLRLSCAASGFTFRSFGMSWVRQAPGKGPEWVSSISGSGSDT LYADSVKGRFTISRDNSKNTLYLQMNSLRPEDTATYYCTIGGSLSRSSQGTLVTVSSA |
| Alb11 | 48 | EVQLVESGGGLVQPGNSLRLSCAASGFTFSSFGMSWVRQAPGKGLEWVSSISGSGSDT LYADSVKGRFTISRDNAKTTLYLQMNSLRPEDTAVYYCTIGGSLSRSSQGTLVTVSS |
| Alb11 (S112K)-A | 49 | EVQLVESGGGLVQPGNSLRLSCAASGFTFSSFGMSWVRQAPGKGLEWVSSISGSGSDT LYADSVKGRFTISRDNAKTTLYLQMNSLRPEDTAVYYCTIGGSLSRSSQGTLVKVSSA |
| Alb82 | 50 | EVQLVESGGGVVQPGNSLRLSCAASGFTFSSFGMSWVRQAPGKGLEWVSSISGSGSDT LYADSVKGRFTISRDNAKTTLYLQMNSLRPEDTALYYCTIGGSLSRSSQGTLVTVSS |
| Alb82-A | 51 | EVQLVESGGGVVQPGNSLRLSCAASGFTFSSFGMSWVRQAPGKGLEWVSSISGSGSDT LYADSVKGRFTISRDNAKTTLYLQMNSLRPEDTALYYCTIGGSLSRSSQGTLVTVSSA |
| Alb82-AA | 52 | EVQLVESGGGVVQPGNSLRLSCAASGFTFSSFGMSWVRQAPGKGLEWVSSISGSGSDT LYADSVKGRFTISRDNAKTTLYLQMNSLRPEDTALYYCTIGGSLSRSSQGTLVTVSSA A |
| Alb82-AAA | 53 | EVQLVESGGGVVQPGNSLRLSCAASGFTFSSFGMSWVRQAPGKGLEWVSSISGSGSDT LYADSVKGRFTISRDNAKTTLYLQMNSLRPEDTALYYCTIGGSLSRSSQGTLVTVSSA AA |
| Alb82-G | 54 | EVQLVESGGGVVQPGNSLRLSCAASGFTFSSFGMSWVRQAPGKGLEWVSSISGSGSDT LYADSVKGRFTISRDNAKTTLYLQMNSLRPEDTALYYCTIGGSLSRSSQGTLVTVSSG |
| Alb82-GG | 55 | EVQLVESGGGVVQPGNSLRLSCAASGFTFSSFGMSWVRQAPGKGLEWVSSISGSGSDT LYADSVKGRFTISRDNAKTTLYLQMNSLRPEDTALYYCTIGGSLSRSSQGTLVTVSSG G |
| Alb82-GGG | 56 | EVQLVESGGGVVQPGNSLRLSCAASGFTFSSFGMSWVRQAPGKGLEWVSSISGSGSDT LYADSVKGRFTISRDNAKTTLYLQMNSLRPEDTALYYCTIGGSLSRSSQGTLVTVSSG GG |
| Alb92 | 57 | EVQLVESGGGVVQPGGSLRLSCAASGFTFRSFGMSWVRQAPGKGPEWVSSISGSGSDT LYADSVKGRFTISRDNSKNTLYLQMNSLRPEDTALYYCTIGGSLSRSSQGTLVTVSS |
| Alb223 | 58 | EVQLVESGGGVVQPGGSLRLSCAASGFTFRSFGMSWVRQAPGKGPEWVSSISGSGSDT LYADSVKGRFTISRDNSKNTLYLQMNSLRPEDTALYYCTIGGSLSRSSQGTLVTVSSA |

TABLE D-continued

Serum albumin binding ISVD sequences ("ID" refers to the SEQ ID NO as used herein), including the CDR sequences

| Name | ID | Amino acid sequence |
|---|---|---|
| ALB CDR1 | 59 | SFGMS |
| ALB CDR2 | 60 | SISGSGSDTLYADSVKG |
| ALB CDR3 | 61 | GGSLSR |

The invention claimed is:

1. A polypeptide comprising at least 3 ISVDs, in which a first ISVD specifically binds matrix metalloproteinase 13 (MMP13), a second ISVD specifically binds ADAMTS5 and a third ISVD specifically binds Aggrecan;
   wherein said ISVD specifically binding MMP13 comprises 3 complementarity determining regions, wherein the complementarity determining regions are CDR1 to CDR3, in which
   (i) CDR1 comprises SEQ ID NO: 8;
   (ii) CDR2 comprises SEQ ID NO: 10; and
   (iii) CDR3 comprises SEQ ID NO: 12;
   wherein said ISVD specifically binding ADAMTS5 comprises 3 complementarity determining regions, wherein the complementarity determining regions are CDR1 to CDR3, in which
   (i) CDR1 comprises SEQ ID NO: 14;
   (ii) CDR2 comprises SEQ ID NO: 16; and
   (iii) CDR3 comprises SEQ ID NO: 18; and
   wherein said ISVD specifically binding Aggrecan comprises 3 complementarity determining regions, wherein the complementarity determining regions are CDR1 to CDR3, in which
   (i) CDR1 comprises (a) SEQ ID NO: 19, or (b) an amino acid sequence according to SEQ ID NO: 19 that has amino acid substitutions at positions 7 and/or 9, wherein the amino acid substitutions are:
   N at position 7 in SEQ ID NO: 19 changed to S; and/or
   V at position 9 changed to M;
   (ii) CDR2 comprises (a) SEQ ID NO: 21, or (b) an amino acid sequence according to SEQ ID NO: 21 that has amino acid substitutions at positions 1, 3, 4, 8, 9, and/or combinations thereof, wherein the amino acid substitutions are:

T at position 1 in SEQ ID NO: 21 changed to A;
   S at position 3 in SEQ ID NO: 21 changed to R;
   S at position 4 in SEQ ID NO: 21 changed to T;
   A at position 8 in SEQ ID NO: 21 changed to T; and/or
   N at position 9 in SEQ ID NO: 21 changed to D; and
   (iii) CDR3 comprises (a) SEQ ID NO: 23, or (b) an amino acid sequence according to SEQ ID NO: 23 that has amino acid substitutions at positions 4 and/or 8, wherein the amino acid substitutions are:
   H at position 4 in SEQ ID NO: 23 changed to R; and/or
   V at position 8 in SEQ ID NO: 23 changed to D.

2. The polypeptide according to claim 1, wherein said ISVD specifically binding MMP13 comprises or consists of SEQ ID NO: 2.

3. The polypeptide according to claim 1, wherein said ISVD specifically binding ADAMTS5 comprises or consists of SEQ ID NO: 3.

4. The polypeptide according to claim 1, wherein said ISVD specifically binding Aggrecan comprises or consists of SEQ ID NO: 4.

5. The polypeptide according to claim 1, wherein said ISVDs are linked to each other via a linker selected from the group consisting of SEQ ID NOs: 24 to 40.

6. The polypeptide according to claim 1, in which said polypeptide comprises a first ISVD specifically binding MMP13, a second ISVD specifically binding ADAMTS5, a third ISVD specifically binding Aggrecan and the polypeptide further comprises a fourth ISVD specifically binding Aggrecan, wherein the fourth ISVD has the same CDR1, CDR2 and CDR3 as defined in claim 1 for the third ISVD binding Aggrecan.

7. The polypeptide according to claim 6, wherein said polypeptide comprises or consists of SEQ ID NO: 1 or 62, or comprises or consists of a polypeptide that has at least 95% sequence identity to SEQ ID NO: 1 or 62.

8. A pharmaceutical composition comprising the polypeptide according to claim 1.

9. A nucleic acid encoding the polypeptide according to claim 1.

10. An expression vector comprising the nucleic acid according to claim 9.

11. A host or host cell comprising the nucleic acid according to claim 9.

12. A method for producing a, comprising the steps of:
a) expressing, in a suitable host cell, host organism or suitable expression system, the nucleic acid according to claim 9; optionally followed by
b) isolating and/or purifying the polypeptide.

13. A method of treating a disease or disorder in an individual, the method comprising administering the polypeptide according to claim 1 to said individual in an amount effective to treat the disease or disorder, wherein the disease or disorder is selected from the group consisting of arthropathies and chondrodystrophies, arthritic disease, osteoarthritis, rheumatoid arthritis, gouty arthritis, psoriatic arthritis, traumatic rupture or detachment, achondroplasia, costochondritis, Spondyloepimetaphyseal dysplasia, spinal disc herniation, lumbar disk degeneration disease, degenerative joint disease, relapsing polychondritis, osteochondritis dissecans, aggrecanopathies, NASH, chronic periodontitis and abdominal aortic aneurysms.

\* \* \* \* \*

UNITED STATES PATENT AND TRADEMARK OFFICE
CERTIFICATE OF CORRECTION

| | |
|---|---|
| PATENT NO. | : 11,813,307 B2 |
| APPLICATION NO. | : 16/617846 |
| DATED | : November 14, 2023 |
| INVENTOR(S) | : Soren Steffensen et al. |

It is certified that error appears in the above-identified patent and that said Letters Patent is hereby corrected as shown below:

In the Claims

Claim 12, Column 155, Line 13:
Please delete:
"A method for producing a, comprising the steps of:"
Please replace with:
"A method for producing a polypeptide according to claim 1, comprising the steps of:"

Signed and Sealed this
Ninth Day of April, 2024

Katherine Kelly Vidal
*Director of the United States Patent and Trademark Office*